United States Patent [19]

Potter et al.

[11] Patent Number: 5,723,129
[45] Date of Patent: *Mar. 3, 1998

[54] GNRH-LEUKOTOXIN CHIMERAS

[75] Inventors: Andrew A. Potter; John G. Manns, both of Saskatoon, Canada

[73] Assignee: University of Saskatchewan, Saskatoon, Canada

[*] Notice: The term of this patent shall not extend beyond the expiration date of Pat. No. 5,422,110.

[21] Appl. No.: 387,156

[22] Filed: Feb. 10, 1995

Related U.S. Application Data

[63] Continuation-in-part of Ser. No. 960,932, Oct. 14, 1992, Pat. No. 5,422,110, which is a continuation-in-part of Ser. No. 779,171, Oct. 16, 1991, abandoned.

[51] Int. Cl.$^6$ .................... A61K 39/02; A61K 38/00; C12N 15/00; C07K 2/00
[52] U.S. Cl. .................... 424/200.1; 424/255.1; 424/184.1; 424/198.1; 424/193.1; 424/192.1; 935/11; 935/12; 935/13; 514/2; 514/7; 514/12; 514/15; 530/300
[58] Field of Search .................... 424/184.1, 200.1, 424/198.1, 193.1, 192.1, 255.1; 935/11, 12, 13; 530/300; 514/2, 7, 12, 15

[56] References Cited

U.S. PATENT DOCUMENTS

| | | |
|---|---|---|
| 4,556,555 | 12/1985 | Esbenshade . |
| 4,608,251 | 8/1986 | Mia . |
| 5,028,423 | 7/1991 | Prickett . |
| 5,238,823 | 8/1993 | Potter et al. . |
| 5,273,889 | 12/1993 | Potter et al. . |
| 5,422,110 | 6/1995 | Potter et al. . |
| 5,594,107 | 1/1997 | Potter et al. . |

FOREIGN PATENT DOCUMENTS

| | | |
|---|---|---|
| 2081950 | 2/1993 | Canada . |
| 2099707 | 3/1994 | Canada . |
| 9115237 | 10/1991 | WIPO . |
| 9203558 | 3/1992 | WIPO . |

OTHER PUBLICATIONS

Lally et al. 1994. JBC. 269(49): 31289–295.
Hughes et al. 1992. Inf & Immun. 60(2): 565–570.
Sad et al. 1991. Immunology 74:223–227.
Forestier et al. 1991. Inf & Imm. 59(11): 4212–4220.
Houghten et al. 1986 Vaccines 86. pp. 21–25.
Welch. Mol. Microbiol. 5(3): 521–528.
Bowie et al. 1990. Science. 247: 1306–1310.
Que et al. 1988. Inf & Imm. 56(10): 2645–49.

*Primary Examiner*—N. M. Minnifield
*Attorney, Agent, or Firm*—Robins & Associates

[57] ABSTRACT

New immunological carrier systems, DNA encoding the same, and the use of these systems, are disclosed. The carrier systems include chimeric proteins which comprise a leukotoxin polypeptide fused to a selected GnRH multimer which consists essentially of at least one repeating GnRH decapeptide sequence, or at least one repeating unit of a sequence corresponding to at least one epitope of a selected GnRH molecule. Under the invention, the selected GnRH sequences may all be the same, or may correspond to different derivatives, analogues, variants or epitopes of GnRH so long as the GnRH sequences are capable of eliciting an immune response. The leukotoxin functions to increase the immunogenicity of the GnRH multimer fused thereto.

26 Claims, 25 Drawing Sheets

GnRH-1:
```
    Gln His Trp Ser Tyr Gly Leu Arg Pro Gly
...CAG CAT TGG AGC TAC GGC CTG CGC CCT GGC...
...GTC GTA ACC TCG ATG CCG GAC GCG GGA CCG...
```

FIG. 1A

GnRH-2:
```
       (1)                                              (2)
[Gln His Trp Ser Tyr Gly Leu Arg Pro Gly Ser Gly Ser Gln Asp Trp Ser
...CAG CAT TGG AGC TAC GGC CTG CGC CCT GGC AGC GGT TCT CAA GAT TGG AGC
...GTC GTA ACC TCG ATG CCG GAC GCG GGA CCG TCG CCA AGA GTT CTA ACC TCG
 1                   5                   10                  15
                               (3)
Tyr Gly Leu Arg Pro Gly Gly Ser Ser Gln His Trp Ser Tyr Gly Leu Arg
TAC GGC CTG CGT CCG GGT GGC TCT AGC CAG CAT TGG AGC TAC GGC CTG CGC
ATG CCG GAC GCA GGC CCA CCG AGA TCG GTC GTA ACC TCG ATG CCG GAC GCG
               20                  25                  30
                       (4)
Pro Gly Ser Gly Ser Gln Asp Trp Ser Tyr Gly Leu Arg Pro Gly
CCT GGC AGC GGT AGC CAA GAT TGG AGC TAC GGC CTG CGT CCG GGT...
GGA CCG TCG CCA TCG GTT CTA ACC TCG ATG CCG GAC GCA GGC CCA...
          35                  40                  45          49
```

```
            10          20          30          40
ATG GCT ACT GTT ATA GAT CTA AGC TTC CCA AAA ACT GGG GCA AAA
MET Ala Thr Val Ile Asp Leu Ser Phe Pro Lys Thr Gly Ala Lys 50          60          70          80          90
AAA ATT ATC CTC TAT ATT CCC CAA AAT TAC CAA TAT GAT ACT GAA
Lys Ile Ile Leu Tyr Ile Pro Gln Asn Tyr Gln Tyr Asp Thr Glu 100         110         120         130
CAA GGT AAT GGT TTA CAG GAT TTA GTC AAA GCG GCC GAA GAG TTG
Gln Gly Asn Gly Leu Gln Asp Leu Val Lys Ala Ala Glu Glu Leu 140         150         160         170         180
GGG ATT GAG GTA CAA AGA GAA GAA CGC AAT AAT ATT GCA ACA GCT
Gly Ile Glu Val Gln Arg Glu Glu Arg Asn Asn Ile Ala Thr Ala 190         200         210         220
CAA ACC AGT TTA GGC ACG ATT CAA ACC GCT ATT GGC TTA ACT GAG
Gln Thr Ser Leu Gly Thr Ile Gln Thr Ala Ile Gly Leu Thr Glu 230         240         250         260         270
CGT GGC ATT GTG TTA TCC GCT CCA CAA ATT GAT AAA TTG CTA CAG
Arg Gly Ile Val Leu Ser Ala Pro Gln Ile Asp Lys Leu Leu Gln 280         290         300         310

AAA ACT AAA GCA GGC CAA GCA TTA GGT TCT GCC GAA AGC ATT GTA
Lys Thr Lys Ala Gly Gln Ala Leu Gly Ser Ala Glu Ser Ile Val 320         330         340         350         360
CAA AAT GCA AAT AAA GCC AAA ACT GTA TTA TCT GGC ATT CAA TCT
Gln Asn Ala Asn Lys Ala Lys Thr Val Leu Ser Gly Ile Gln Ser 370         380         390         400
ATT TTA GGC TCA GTA TTG GCT GGA ATG GAT TTA GAT GAG GCC TTA
Ile Leu Gly Ser Val Leu Ala Gly MET Asp Leu Asp Glu Ala Leu
```

FIG. 5A

```
     410           420           430           440           450
      |             |             |             |             |
CAG AAT AAC AGC AAC CAA CAT GCT CTT GCT AAA GCT GGC TTG GAG
Gln Asn Asn Ser Asn Gln His Ala Leu Ala Lys Ala Gly Leu Glu 460           470           480           490
               |             |             |             |
CTA ACA AAT TCA TTA ATT GAA AAT ATT GCT AAT TCA GTA AAA ACA
Leu Thr Asn Ser Leu Ile Glu Asn Ile Ala Asn Ser Val Lys Thr 500           510           520           530           540
      |             |             |             |             |
CTT GAC GAA TTT GGT GAG CAA ATT AGT CAA TTT GGT TCA AAA CTA
Leu Asp Glu Phe Gly Glu Gln Ile Ser Gln Phe Gly Ser Lys Leu 550           560           570           580
               |             |             |             |
CAA AAT ATC AAA GGC TTA GGG ACT TTA GGA GAC AAA CTC AAA AAT
Gln Asn Ile Lys Gly Leu Gly Thr Leu Gly Asp Lys Leu Lys Asn 590           600           610           620           630
               |             |             |             |             |
ATC GGT GGA CTT GAT AAA GCT GGC CTT GGT TTA GAT GTT ATC TCA
Ile Gly Gly Leu Asp Lys Ala Gly Leu Gly Leu Asp Val Ile Ser 640           650           660           670
               |             |             |             |
GGG CTA TTA TCG GGC GCA ACA CCT GCA CTT GTA CTT GCA GAT AAA
Gly Leu Leu Ser Gly Ala Thr Ala Ala Leu Val Leu Ala Asp Lys 680           690           700           710           720
      |             |             |             |             |
AAT GCT TCA ACA GCT AAA AAA GTC GGT GCG GGT TTT GAA TTG GCA
Asn Ala Ser Thr Ala Lys Lys Val Gly Ala Gly Phe Glu Leu Ala 730           740           750           760
               |             |             |             |
AAC CAA GTT GTT GGT AAT ATT ACC AAA GCC GTT TCT TCT TAC ATT
Asn Gln Val Val Gly Asn Ile Thr Lys Ala Val Ser Ser Tyr Ile 770           780           790           800           810
      |             |             |             |             |
TTA GCC CAA CGT GTT GCA GCA GGT TTA TCT TCA ACT GGG CCT GTG
Leu Ala Gln Arg Val Ala Ala Gly Leu Ser Ser Thr Gly Pro Val
```

FIG. 5B

```
     820           830           840           850
GCT GCT TTA ATT GCT TCT ACT GTT TCT CTT GCG ATT AGC CCA TTA
Ala Ala Leu Ile Ala Ser Thr Val Ser Leu Ala Ile Ser Pro Leu 860           870           880           890           900
GCA TTT GCC GGT ATT GCC GAT AAA TTT AAT CAT GCA AAA AGT TTA
Ala Phe Ala Gly Ile Ala Asp Lys Phe Asn His Ala Lys Ser Leu 910           920           930           940
GAG AGT TAT GCC GAA CGC TTT AAA AAA TTA GGC TAT GAC GGA GAT
Glu Ser Tyr Ala Glu Arg Phe Lys Lys Leu Gly Tyr Asp Gly Asp 950           960           970           980           990
AAT TTA TTA GCA GAA TAT CAG CGG GGA ACA GGG ACT ATT GAT GCA
Asn Leu Leu Ala Glu Tyr Gln Arg Gly Thr Gly Thr Ile Asp Ala 1000          1010          1020          1030
TCG GTT ACT GCA ATT AAT ACC GCA TTG GCC GCT ATT GCT GGT GGT
Ser Val Thr Ala Ile Asn Thr Ala Leu Ala Ala Ile Ala Gly Gly 1040          1050          1060          1070          1080
GTG TCT GCT GCT GCA GCC GGC TCG GTT ATT GCT TCA CCG ATT GCC
Val Ser Ala Ala Ala Ala Gly Ser Val Ile Ala Ser Pro Ile Ala 1090          1100          1110          1120
TTA TTA GTA TCT GGG ATT ACC GGT GTA ATT TCT ACG ATT CTG CAA
Leu Leu Val Ser Gly Ile Thr Gly Val Ile Ser Thr Ile Leu Gln 1130          1140          1150          1160          1170
TAT TCT AAA CAA GCA ATG TTT GAG CAC GTT GCA AAT AAA ATT CAT
Tyr Ser Lys Gln Ala MET Phe Glu His Val Ala Asn Lys Ile His 1180          1190          1200          1210
AAC AAA ATT GTA GAA TGG GAA AAA AAT AAT CAC GGT AAG AAC TAC
Asn Lys Ile Val Glu Trp Glu Lys Asn Asn His Gly Lys Asn Tyr
```

FIG. 5C

```
      1220          1230          1240          1250          1260
TTT GAA AAT GGT TAC GAT CCC CGT TAT CTT GCG AAT TTA CAA GAT
Phe Glu Asn Gly Tyr Asp Ala Arg Tyr Leu Ala Asn Leu Gln Asp 1270          1280          1290          1300
AAT ATG AAA TTC TTA CTG AAC TTA AAC AAA GAG TTA CAG GCA GAA
Asn MET Lys Phe Leu Leu Asn Leu Asn Lys Glu Leu Gln Ala Glu 1310          1320          1330          1340          1350
CGT GTC ATC GCT ATT ACT CAG CAG CAA TGG GAT AAC AAC ATT GGT
Arg Val Ile Ala Ile Thr Gln Gln Gln Trp Asp Asn Asn Ile Gly 1360          1370          1380          1390
GAT TTA GCT GGT ATT AGC CGT TTA GGT GAA AAA GTC CTT AGT GGT
Asp Leu Ala Gly Ile Ser Arg Leu Gly Glu Lys Val Leu Ser Gly 1400          1410          1420          1430          1440
AAA GCC TAT GTG GAT GCG TTT GAA GAA GGC AAA CAC ATT AAA GCC
Lys Ala Tyr Val Asp Ala Phe Glu Glu Gly Lys His Ile Lys Ala 1450          1460          1470          1480
GAT AAA TTA GTA CAG TTG GAT TCG GCA AAC GGT ATT ATT GAT GTG
Asp Lys Leu Val Gln Leu Asp Ser Ala Asn Gly Ile Ile Asp Val 1490          1500          1510          1520          1530
AGT AAT TCG GGT AAA GCG AAA ACT CAG CAT ATC TTA TTC AGA ACG
Ser Asn Ser Gly Lys Ala Lys Thr Gln His Ile Leu Phe Arg Thr 1540          1550          1560          1570
CCA TTA TTG ACG CCG GGA ACA GAG CAT CGT GAA CGC GTA CAA ACA
Pro Leu Leu Thr Pro Gly Thr Glu His Arg Glu Arg Val Gln Thr 1580          1590          1600          1610          1620
GGT AAA TAT GAA TAT ATT ACC AAG CTC AAT ATT AAC CGT GTA GAT
Gly Lys Tyr Glu Tyr Ile Thr Lys Leu Asn Ile Asn Arg Val Asp
```

FIG. 5D

```
       1630              1640              1650              1660
         |                 |                 |                 |
AGC TGG AAA ATT ACA GAT GGT GCA GCA AGT TCT ACC TTT GAT TTA
Ser Trp Lys Ile Thr Asp Gly Ala Ala Ser Ser Thr Phe Asp Leu 1670              1680              1690              1700              1710
         |                 |                 |                 |                 |
ACT AAC GTT GTT CAG CGT ATT GGT ATT GAA TTA GAC AAT GCT GGA
Thr Asn Val Val Gln Arg Ile Gly Ile Glu Leu Asp Asn Ala Gly 1720              1730              1740              1750
         |                 |                 |                 |
AAT GTA ACT AAA ACC AAA GAA ACA AAA ATT ATT GCC AAA CTT GGT
Asn Val Thr Lys Thr Lys Glu Thr Lys Ile Ile Ala Lys Leu Gly 1760              1770              1780              1790              1800
         |                 |                 |                 |                 |
GAA GGT GAT GAC AAC GTA TTT GTT GGT TCT GGT ACG ACG GAA ATT
Glu Gly Asp Asp Asn Val Phe Val Gly Ser Gly Thr Thr Glu Ile 1810              1820              1830              1840
         |                 |                 |                 |
GAT GGC GGT GAA GGT TAC GAC CGA GTT CAC TAT AGC CGT GGA AAC
Asp Gly Gly Glu Gly Tyr Asp Arg Val His Tyr Ser Arg Gly Asn 1850              1860              1870              1880              1890
         |                 |                 |                 |                 |
TAT GGT GCT TTA ACT ATT GAT GCA ACC AAA GAG ACC GAG CAA GGT
Tyr Gly Ala Leu Thr Ile Asp Ala Thr Lys Glu Thr Glu Gln Gly 1900              1910              1920              1930
         |                 |                 |                 |
AGT TAT ACC GTA AAT CGT TTC GTA GAA ACC GGT AAA GCA CTA CAC
Ser Tyr Thr Val Asn Arg Phe Val Glu Thr Gly Lys Ala Leu His 1940              1950              1960              1970              1980
         |                 |                 |                 |                 |
GAA GTG ACT TCA ACC CAT ACC GCA TTA GTG GGC AAC CGT GAA GAA
Glu Val Thr Ser Thr His Thr Ala Leu Val Gly Asn Arg Glu Glu 1990              2000              2010              2020
         |                 |                 |                 |
AAA ATA GAA TAT CGT CAT AGC AAT AAC CAG CAC CAT GCC GGT TAT
Lys Ile Glu Tyr Arg His Ser Asn Asn Gln His His Ala Gly Tyr
```

FIG. 5E

```
        2030            2040            2050            2060            2070
         |               |               |               |               |
TAC ACC AAA GAT ACC TTG AAA GCT GTT GAA GAA ATT ATC GGT ACA
Tyr Thr Lys Asp Thr Leu Lys Ala Val Glu Glu Ile Ile Gly Thr 2080            2090            2100            2110
                 |               |               |               |
TCA CAT AAC GAT ATC TTT AAA GGT AGT AAG TTC AAT GAT GCC TTT
Ser His Asn Asp Ile Phe Lys Gly Ser Lys Phe Asn Asp Ala Phe 2120            2130            2140            2150            2160
         |               |               |               |               |
AAC GGT GGT GAT GGT GTC GAT ACT ATT GAC GGT AAC GAC GGC AAT
Asn Gly Gly Asp Gly Val Asp Thr Ile Asp Gly Asn Asp Gly Asn 2170            2180            2190            2200
                 |               |               |               |
GAC CGC TTA TTT GGT GGT AAA GGC GAT GAT ATT CTC GAT GGT GGA
Asp Arg Leu Phe Gly Gly Lys Gly Asp Asp Ile Leu Asp Gly Gly 2210            2220            2230            2240            2250
         |               |               |               |               |
AAT GGT GAT GAT TTT ATC GAT GGC GGT AAA GGC AAC GAC CTA TTA
Asn Gly Asp Asp Phe Ile Asp Gly Gly Lys Gly Asn Asp Leu Leu 2260            2270            2280            2290
                 |               |               |               |
CAC GGT GGC AAG GGC GAT GAT ATT TTC GTT CAC CGT AAA GGC GAT
His Gly Gly Lys Gly Asp Asp Ile Phe Val His Arg Lys Gly Asp 2300            2310            2320            2330            2340
         |               |               |               |               |
GGT AAT GAT ATT ATT ACC GAT TCT GAC GGC AAT GAT AAA TTA TCA
Gly Asn Asp Ile Ile Thr Asp Ser Asp Gly Asn Asp Lys Leu Ser 2350            2360            2370            2380
                 |               |               |               |
TTC TCT GAT TCG AAC TTA AAA GAT TTA ACA TTT GAA AAA GTT AAA
Phe Ser Asp Ser Asn Leu Lys Asp Leu Thr Phe Glu Lys Val Lys 2390            2400            2410            2420            2430
         |               |               |               |               |
CAT AAT CTT GTC ATC ACG AAT AGC AAA AAA GAG AAA GTG ACC ATT
His Asn Leu Val Ile Thr Asn Ser Lys Lys Glu Lys Val Thr Ile
```

FIG. 5F

```
      2440            2450            2460            2470
CAA AAC TGG TTC CGA GAG GCT GAT TTT GCT AAA GAA GTG CCT AAT
Gln Asn Trp Phe Arg Glu Ala Asp Phe Ala Lys Glu Val Pro Asn 2480            2490            2500            2510            2520
TAT AAA GCA ACT AAA GAT GAG AAA ATC GAA GAA ATC ATC GGT CAA
Tyr Lys Ala Thr Lys Asp Glu Lys Ile Glu Glu Ile Ile Gly Gln 2530            2540            2550            2560
AAT GGC GAG CGG ATC ACC TCA AAG CAA GTT GAT GAT CTT ATC GCA
Asn Gly Glu Arg Ile Thr Ser Lys Gln Val Asp Asp Leu Ile Ala 2570            2580            2590            2600            2610
AAA GGT AAC GGC AAA ATT ACC CAA GAT GAG CTA TCA AAA GTT GTT
Lys Gly Asn Gly Lys Ile Thr Gln Asp Glu Leu Ser Lys Val Val 2620            2630            2640            2650
GAT AAC TAT GAA TTG CTC AAA CAT AGC AAA AAT GTG ACA AAC AGC
Asp Asn Tyr Glu Leu Leu Lys His Ser Lys Asn Val Thr Asn Ser 2660            2670            2680            2690            2700
TTA GAT AAG TTA ATC TCA TCT GTA AGT GCA TTT ACC TCG TCT AAT
Leu Asp Lys Leu Ile Ser Ser Val Ser Ala Phe Thr Ser Ser Asn 2710            2720            2730            2740
GAT TCG AGA AAT GTA TTA GTG GCT CCA ACT TCA ATG TTG GAT CAA
Asp Ser Arg Asn Val Leu Val Ala Pro Thr Ser MET Leu Asp Gln 2750            2760            2770            2780            2790
AGT TTA TCT TCT CTT CAA TTT GCT AGG GGA TCT CAG CAT TGG AGC
Ser Leu Ser Ser Leu Gln Phe Ala Arg Gly Ser Gln His Trp Ser 2800            2810            2820            2830
TAC GGC CTG CGC CCT GGC AGC GGT TCT CAA GAT TGG AGC TAC GGC
Tyr Gly Leu Arg Pro Gly Ser Gly Ser Gln Asp Trp Ser Tyr Gly
```

FIG. 5G

```
       2840        2850         2860         2870         2880
        |           |            |            |            |
CTG CGT CCG GGT GGC TCT AGC CAG CAT TGG AGC TAC GGC CTG CGC
Leu Arg Pro Gly Gly Ser Ser Gln His Trp Ser Tyr Gly Leu Arg 2890         2900         2910         2920
         |            |            |            |
CCT GGC AGC GGT AGC CAA GAT TGG AGC TAC GGC CTG CGT CCG GGT
Pro Gly Ser Gly Ser Gln Asp Trp Ser Tyr Gly Leu Arg Pro Gly

2930
   |
GGA TCC TAG
Gly Ser ---
```

```
              10              20              30              40
              |               |               |               |
ATG GCT ACT GTT ATA GAT CTA AGC TTC CCA AAA ACT GGG GCA AAA
MET Ala Thr Val Ile Asp Leu Ser Phe Pro Lys Thr Gly Ala Lys 50              60              70              80              90
      |               |               |               |               |
AAA ATT ATC CTC TAT ATT CCC CAA AAT TAC CAA TAT GAT ACT GAA
Lys Ile Ile Leu Tyr Ile Pro Gln Asn Tyr Gln Tyr Asp Thr Glu 100             110             120             130
              |               |               |               |
CAA GGT AAT GGT TTA CAG GAT TTA GTC AAA GCG GCC GAA GAG TTG
Gln Gly Asn Gly Leu Gln Asp Leu Val Lys Ala Ala Glu Glu Leu 140             150             160             170             180
      |               |               |               |               |
GGG ATT GAG GTA CAA AGA GAA GAA CGC AAT AAT ATT GCA ACA GCT
Gly Ile Glu Val Gln Arg Glu Glu Arg Asn Asn Ile Ala Thr Ala 190             200             210             220
              |               |               |               |
CAA ACC AGT TTA GGC ACG ATT CAA ACC GCT ATT GGC TTA ACT GAG
Gln Thr Ser Leu Gly Thr Ile Gln Thr Ala Ile Gly Leu Thr Glu 230             240             250             260             270
      |               |               |               |               |
CGT GGC ATT GTG TTA TCC GCT CCA CAA ATT GAT AAA TTG CTA CAG
Arg Gly Ile Val Leu Ser Ala Pro Gln Ile Asp Lys Leu Leu Gln 280             290             300             310
              |               |               |               |
AAA ACT AAA GCA GGC CAA GCA TTA GGT TCT GCC GAA AGC ATT GTA
Lys Thr Lys Ala Gly Gln Ala Leu Gly Ser Ala Glu Ser Ile Val 320             330             340             350             360
      |               |               |               |               |
CAA AAT GCA AAT AAA GCC AAA ACT GTA TTA TCT GGC ATT CAA TCT
Gln Asn Ala Asn Lys Ala Lys Thr Val Leu Ser Gly Ile Gln Ser 370             380             390             400
              |               |               |               |
ATT TTA GGC TCA GTA TTG GCT GGA ATG GAT TTA GAT GAG GCC TTA
Ile Leu Gly Ser Val Leu Ala Gly MET Asp Leu Asp Glu Ala Leu
```

FIG. 7A

```
      410             420             430             440             450
CAG AAT AAC AGC AAC CAA CAT GCT CTT GCT AAA GCT GGC TTG GAG
Gln Asn Asn Ser Asn Gln His Ala Leu Ala Lys Ala Gly Leu Glu 460             470             480             490
CTA ACA AAT TCA TTA ATT GAA AAT ATT GCT AAT TCA GTA AAA ACA
Leu Thr Asn Ser Leu Ile Glu Asn Ile Ala Asn Ser Val Lys Thr 500             510             520             530             540
CTT GAC GAA TTT GGT GAG CAA ATT AGT CAA TTT GGT TCA AAA CTA
Leu Asp Glu Phe Gly Glu Gln Ile Ser Gln Phe Gly Ser Lys Leu 550             560             570             580
CAA AAT ATC AAA GGC TTA GGG ACT TTA GGA GAC AAA CTC AAA AAT
Gln Asn Ile Lys Gly Leu Gly Thr Leu Gly Asp Lys Leu Lys Asn 590             600             610             620             630
ATC GGT GGA CTT GAT AAA GCT GGC CTT GGT TTA GAT GTT ATC TCA
Ile Gly Gly Leu Asp Lys Ala Gly Leu Gly Leu Asp Val Ile Ser 640             650             660             670
GGG CTA TTA TCG GGC GCA ACA GCT GCA CTT GTA CTT GCA GAT AAA
Gly Leu Leu Ser Gly Ala Thr Ala Ala Leu Val Leu Ala Asp Lys 680             690             700             710             720
AAT GCT TCA ACA GCT AAA AAA GTG GGT GCG GGT TTT GAA TTG GCA
Asn Ala Ser Thr Ala Lys Lys Val Gly Ala Gly Phe Glu Leu Ala 730             740             750             760
AAC CAA GTT GTT GGT AAT ATT ACC AAA GCC GTT TCT TCT TAC ATT
Asn Gln Val Val Gly Asn Ile Thr Lys Ala Val Ser Ser Tyr Ile
```

FIG. 7B

```
        770             780             790             800             810
         |               |               |               |               |
TTA GCC CAA CGT GTT GCA GCA GGT TTA TCT TCA ACT GGG CCT GTG
Leu Ala Gln Arg Val Ala Ala Gly Leu Ser Ser Thr Gly Pro Val 820             830             840             850
                 |               |               |               |
GCT GCT TTA ATT GCT TCT ACT GTT TCT CTT GCG ATT AGC CCA TTA
Ala Ala Leu Ile Ala Ser Thr Val Ser Leu Ala Ile Ser Pro Leu 860             870             880             890             900
         |               |               |               |               |
GCA TTT GCC GGT ATT GCC GAT AAA TTT AAT CAT GCA AAA AGT TTA
Ala Phe Ala Gly Ile Ala Asp Lys Phe Asn His Ala Lys Ser Leu 910             920             930             940
                 |               |               |               |
GAG AGT TAT GCC GAA CGC TTT AAA AAA TTA GGC TAT GAC GGA GAT
Glu Ser Tyr Ala Glu Arg Phe Lys Lys Leu Gly Tyr Asp Gly Asp 950             960             970             980             990
         |               |               |               |               |
AAT TTA TTA GCA GAA TAT CAG CGC GGA ACA GGG ACT ATT GAT GCA
Asn Leu Leu Ala Glu Tyr Gln Arg Gly Thr Gly Thr Ile Asp Ala 1000            1010            1020            1030
                 |               |               |               |
TCG GTT ACT GCA ATT AAT ACC GCA TTG GCC GCT ATT GCT GGT GGT
Ser Val Thr Ala Ile Asn Thr Ala Leu Ala Ala Ile Ala Gly Gly 1040            1050            1060            1070            1080
         |               |               |               |               |
GTG TCT GCT GCT GCA GCC AAC TTA AAA GAT TTA ACA TTT GAA AAA
Val Ser Ala Ala Ala Ala Asn Leu Lys Asp Leu Thr Phe Glu Lys 1090            1100            1110            1120
                 |               |               |               |
GTT AAA CAT AAT CTT GTC ATC ACG AAT AGC AAA AAA GAG AAA GTG
Val Lys His Asn Leu Val Ile Thr Asn Ser Lys Lys Glu Lys Val 1130            1140            1150            1160            1170
         |               |               |               |               |
ACC ATT CAA AAC TGG TTC CGA GAG GCT GAT TTT GCT AAA GAA GTG
Thr Ile Gln Asn Trp Phe Arg Glu Ala Asp Phe Ala Lys Glu Val
```

FIG. 7C

```
      1180            1190            1200            1210
CCT AAT TAT AAA GCA ACT AAA GAT GAG AAA ATC GAA GAA ATC ATC
Pro Asn Tyr Lys Ala Thr Lys Asp Glu Lys Ile Glu Glu Ile Ile 1220            1230            1240            1250            1260
GGT CAA AAT GGC GAG CGG ATC ACC TCA AAG CAA GTT GAT GAT CTT
Gly Gln Asn Gly Glu Arg Ile Thr Ser Lys Gln Val Asp Asp Leu 1270            1280            1290            1300
ATC GCA AAA GGT AAC GGC AAA ATT ACC CAA GAT GAG CTA TCA AAA
Ile Ala Lys Gly Asn Gly Lys Ile Thr Gln Asp Glu Leu Ser Lys 1310            1320            1330            1340            1350
GTT GTT GAT AAC TAT GAA TTG CTC AAA CAT AGC AAA AAT GTG ACA
Val Val Asp Asn Tyr Glu Leu Leu Lys His Ser Lys Asn Val Thr 1360            1370            1380            1390
AAC AGC TTA GAT AAG TTA ATC TCA TCT GTA AGT GCA TTT ACC TCG
Asn Ser Leu Asp Lys Leu Ile Ser Ser Val Ser Ala Phe Thr Ser 1400            1410            1420            1430            1440
TCT AAT GAT TCG AGA AAT GTA TTA GTG GCT CCA ACT TCA ATG TTG
Ser Asn Asp Ser Arg Asn Val Leu Val Ala Pro Thr Ser MET Leu 1450            1460            1470            1480
GAT CAA AGT TTA TCT TCT CTT CAA TTT GCT AGG GGA TCT CAG CAT
Asp Gln Ser Leu Ser Ser Leu Gln Phe Ala Arg Gly Ser Gln His 1490            1500            1510            1520            1530
TGG AGC TAC GGC CTG CGC CCT GCC AGC GGT TCT CAA GAT TGG AGC
Trp Ser Tyr Gly Leu Arg Pro Gly Ser Gly Ser Gln Asp Trp Ser
```

FIG. 7D

```
      1540            1550            1560            1570
TAC GGC CTG CGT CCG GGT GGC TCT AGC CAG CAT TGG AGC TAC GGC
Tyr Gly Leu Arg Pro Gly Gly Ser Ser Gln His Trp Ser Tyr Gly 1580            1590            1600            1610            1620
CTG CGC CCT GGC AGC GGT AGC CAA GAT TGG AGC TAC GGC CTG CGT
Leu Arg Pro Gly Ser Gly Ser Gln Asp Trp Ser Tyr Gly Leu Arg

1630
CCG GGT GGA TCC TAG
Pro Gly Gly Ser ---
```

FIG. 7E

```
         [NaeI]                                   [BstB1]
..GCT GCA GCC|GGC TCG GTT ATT....TTC TCT GAT TCG|AAC TTA AAA..
..CGA CGT CGG|CCG AGC CAA TAA....AAG AGA CTA AGC|TTG AAT TTT...
..Ala Ala Ala|Gly Ser Val Ile....Phe Ser Asp Ser|Asn Leu Lys..
         351                                          785
```

FIG. 8A

```
...GCT GCA GCC   AAC TTA AAA..
...CGA CGT CGG   TTG AAT TTT...
..Ala Ala Ala    Asn Leu Lys...
         351    785
```

FIG. 8B

GNRH-LEUKOTOXIN CHIMERAS

CROSS-REFERENCE TO RELATED APPLICATION

This application is a continuation-in-part of U.S. patent application Ser. No. 07/960,932, filed 14 Oct. 1992 and issued as U.S. Pat. No. 5,422,110, which is a continuation-in-part of U.S. patent application Ser. No. 07/779,171, filed 16 Oct. 1991 now abandoned, which applications are incorporated by reference herein in their entireties and from which priority is claimed pursuant to 35 USC § 120.

TECHNICAL FIELD

The present invention relates generally to immunological carrier systems. More particularly, the invention pertains to leukotoxin-GnRH chimeras including more than one copy of a GnRH polypeptide, which demonstrate enhanced immunogenicity as compared to the immunogenicity of GnRH polypeptides alone.

BACKGROUND OF THE INVENTION

In vertebrates, synthesis and release of the two gonadotrophic hormones, luteinizing hormone (LH) and follicle stimulating hormone (FSH), are regulated by a polypeptide referred to as Gonadotropin releasing hormone (GnRH) (formerly designated LHRH). Accordingly, one approach to fertility control in an animal population is to reduce the levels of GnRH, such as by immunization against GnRH, which effects a reduction in the levels of LH and FSH and the concomitant disruption of estrous cycles and spermatogenesis. See e.g., Adams et al., *J. Anim. Sci.* (1990) 68:2793–2802.

In particular, early studies of the GnRH molecule have shown that it is possible to raise antisera in response to repeated injections of synthetic GnRH peptides (Arimura et al., *Endocrinology* (1973) 93(5):1092–1103). Further, antibodies to GnRH have been raised in a number of species by chemical conjugation of GnRH to a suitable carrier and administration of the conjugate in an appropriate adjuvant (Carelli et al., *Proc. Natl. Acad. Sci.* (1982) 79:5392–5395). Recombinant fusion proteins comprising GnRH or GnRH-analogues have also been described for use in peptide vaccines for the immunological castration or inhibition of reproductive function of various domesticated and farm animals (Meloen et al., *Vaccine* (1994) 12(8):741–746; Hoskinson et al., *Aust. J. Biotechnol.* (1990) 4:166–170; and International Publication Nos. WO 92/19746, published 12 Nov. 1992; WO 91/02799, published 7 Mar. 1991; WO 90/11298, published 4 Oct. 1990 and WO 86/07383, published 18 Dec. 1986).

However, attempts have fallen short of providing adequate immunological sterilization products due to the poor immunogenicity of GnRH peptides and due to the fact that chemical conjugation protocols are difficult to control, rendering substantially heterogenous and poorly-defined GnRH conjugates. Further, peptide vaccines based on GnRH have met with limited success in providing uniform effects on individual animal subjects even after repeated vaccination. In this regard, prior GnRH constructs have failed to provide a uniformly successful immunological sterilization vaccine product due to the fact that GnRH is a small, "self" molecule that is not normally recognized by a subject's immune system, rendering the molecule poorly immunogenic and inherently unable to induce a significant immune response against endogenous GnRH.

It is generally recognized that the immunogenicity of viral antigens, small proteins or endogenous substances may be significantly increased by producing immunogenic forms of those molecules comprising multiple copies of selected epitopes. In this regard, constructs based on two or four repeats of peptides 9–21 of herpes simplex virus type 1 glycoprotein D (Ploeg et al., *J. Immuno. Methods* (1989) 124:211–217), two to six repeats of the antigenic circumsporozoite tetrapeptide NPNA of *Plasmodium falciparum* (Lowell et al., *Science* (1988) 240:800–802), two or four copies of the major immunogenic site of VP1 of foot-and-mouth disease virus (Broekhuijsen et al., *J. gen. Virol.* (1987) 68:3137–3143) and tandem repeats of a GnRH-like polypeptide (Meloen et al., *Vaccine* (1994) 12(8):741–746), have been shown to be effective in increasing the immunogenicity of those molecules.

Furthermore, small proteins or endogenous substances may also be conjugated to a suitable carrier in order to elicit a significant immune response in a challenged host. Suitable carriers are generally polypeptides which include antigenic regions of a protein derived from an infectious material such as a viral surface protein, or a carrier peptide sequence. These carriers serve to non-specifically stimulate T helper cell activity and to help direct antigen to antigen presenting cells for processing and presentation of the peptide at the cell surface in association with molecules of the major histocompatibility complex (MHC).

Several carrier systems have been developed for this purpose. For example, small peptide antigens are often coupled to protein carriers such as keyhole limpet haemocyanin (Bittle et al., *Nature* (1982) 298:30–33), tetanus toxoid (Muller et al., *Proc. Natl. Acad. Sci. U.S.A.* (1982) 7.9:569–573), ovalbumin, and sperm whale myoglobin, to produce an immune response. These coupling reactions typically result in the incorporation of several moles of peptide antigen per mole of carrier protein. Although presentation of the peptide antigen in multiple copies generally enhances immunogenicity, carriers may elicit strong immunity not relevant to the peptide antigen and this may inhibit the immune response to the peptide vaccine on secondary immunization (Schutze et al, *J. Immun.* (1985) 135:2319–2322).

Antigen delivery systems have also been based on particulate carriers. For example, preformed particles have been used as platforms onto which antigens can be coupled and incorporated. Systems based on proteosomes (Lowell et al., *Science* (1988) 240:800–802), immune stimulatory complexes (Morein et al., *Nature* (1984) 308:457–460), and viral particles such as HBsAg (Neurath et al., *Mol. Immunol.* (1989) 26:53–62) and rotavirus inner capsid protein (Redmond et al., *Mol. Immunol.* (1991) 28:269–278) have been developed.

Carrier systems have also been devised using recombinantly produced chimeric proteins that self assemble into particles. For example, the yeast retrotransposon, Ty, encodes a series of proteins that assemble into virus like particles (Ty-VLPs; Kingsman, S. M., and A. J. Kingsman Vacc. (1988) 6:304–306). Foreign genes have been inserted into the TyA gene and expressed in yeast as a fusion protein. The fusion protein retains the capacity to self assemble into particles of uniform size.

Other chimeric protein particles have been examined such as HBsAg, (Valenzuela et al., *Bio/Technol.* (1985) 3:323–326; U.S. Pat. No. 4,722,840; Delpeyroux et al., *Science* (1986) 233:472–475), Hepatitis B core antigen (Clarke et al., *Vaccines* 88 (Ed. H. Ginsberg, et al., 1988) pp.

127–131), Poliovirus (Burke et al., *Nature* (1988) 332:81–82), and Tobacco Mosaic Virus (Haynes et al., *Bio/Technol.* (1986) 4:637–641). However, these carriers are restricted in their usefulness by virtue of the limited size of the active agent which may be inserted into the structural protein without interfering with particle assembly.

Finally, chimeric systems have been devised using a *Pasteurella haemolytica* leukotoxin (LKT) polypeptide fused to a selected antigen. See, e.g., International Publication Nos. WO 93/08290, published 29 Apr. 1993 and WO 92/03558, published 5 Mar. 1992, as well as U.S. Pat. Nos. 5,238,823 and 5,273,889. Inclusion of a LKT carrier portion in a peptide antigen chimera supplies enhanced immunogenicity to the chimera by providing T-cell epitopes having broad species reactivity, thereby eliciting a T-cell dependent immune response in immunized subjects. In this regard, inducement of adequate T-cell help is essential in the generation of an immune response to the peptide antigen portion of the chimera, particularly where the antigen is an endogenous molecule. However, the use of a leukotoxin polypeptide carrier in combination with multiple epitopes of the GnRH peptide has not heretofore been described.

DISCLOSURE OF THE INVENTION

The present invention is based on the construction of novel gene fusions between the *P. haemolytica* leukotoxin gene, variants thereof, and nucleotide sequences encoding multiple GnRH polypeptides. These constructs produce chimeric proteins that display surprisingly enhanced immunogenicity when compared to the immunologic reaction elicited by administration of GnRH alone.

Thus in one embodiment, the present invention is directed to a chimeric protein comprising a leukotoxin polypeptide fused to a multimer consisting essentially of more than one selected GnRH polypeptide, whereby the leukotoxin portion of the chimera acts to increase the immunogenicity of the GnRH polypeptide. More particularly, the GnRH multimer may correspond to more than one copy of a selected GnRH polypeptide or epitope, or multiple tandem repeats of a selected GnRH polypeptide or epitope. Further, the GnRH multimer may be located at the carboxyl or amino terminals, or at sites internal to the leukotoxin polypeptide. The GnRH multimer may also correspond to a molecule of the general formula GnRH-X-GnRH wherein X is selected from the group consisting of a peptide linkage, an amino acid spacer group and [GnRH]$_n$, where n is greater than or equal to 1, and further wherein "GnRH" may comprise any GnRH polypeptide.

Also disclosed are vaccine compositions comprising the chimeric proteins and a pharmaceutically acceptable vehicle, and methods for presenting a selected GnRH multimer to a host subject comprising administering an effective amount of the subject vaccine compositions.

In another embodiment, the subject invention is directed to DNA constructs encoding the chimeric proteins. The DNA constructs comprise a first nucleotide sequence encoding a leukotoxin polypeptide operably linked to a second nucleotide sequence encoding more than one copy of a GnRH epitope.

In yet another embodiment, the subject invention is directed to expression cassettes comprised of (a) the DNA constructs above and (b) control sequences that direct the transcription of the construct whereby the constructs can be transcribed and translated in a host cell.

In another embodiment, the invention is directed to host cells transformed with these expression cassettes.

Another embodiment of the invention provides a method of producing a recombinant polypeptide. The method comprises (a) providing a population of host cells described above and (b) culturing the population of cells under conditions whereby the polypeptide encoded by the expression cassette is expressed.

These and other embodiments of the present invention will readily occur to those of ordinary skill in the art in view of the disclosure herein.

BRIEF DESCRIPTION OF THE FIGURES

FIGS. 1A SEQ ID NOS:1–2 and 1B SEQ ID NOS:3–4 show the nucleotide sequences and amino acid sequences of the GnRH constructs used in the chimeric leukotoxin-GnRH polypeptide gene fusions. FIG. 1A SEQ ID NOS:1–2 depicts GnRH-1 which includes a single copy of a GnRH decapeptide; FIG. 1B SEQ ID NOS:3–4 depicts GnRH-2 which includes four copies of a GnRH decapeptide when n=1, and eight copies of GnRH when n=2, etc.

Figure 3A:
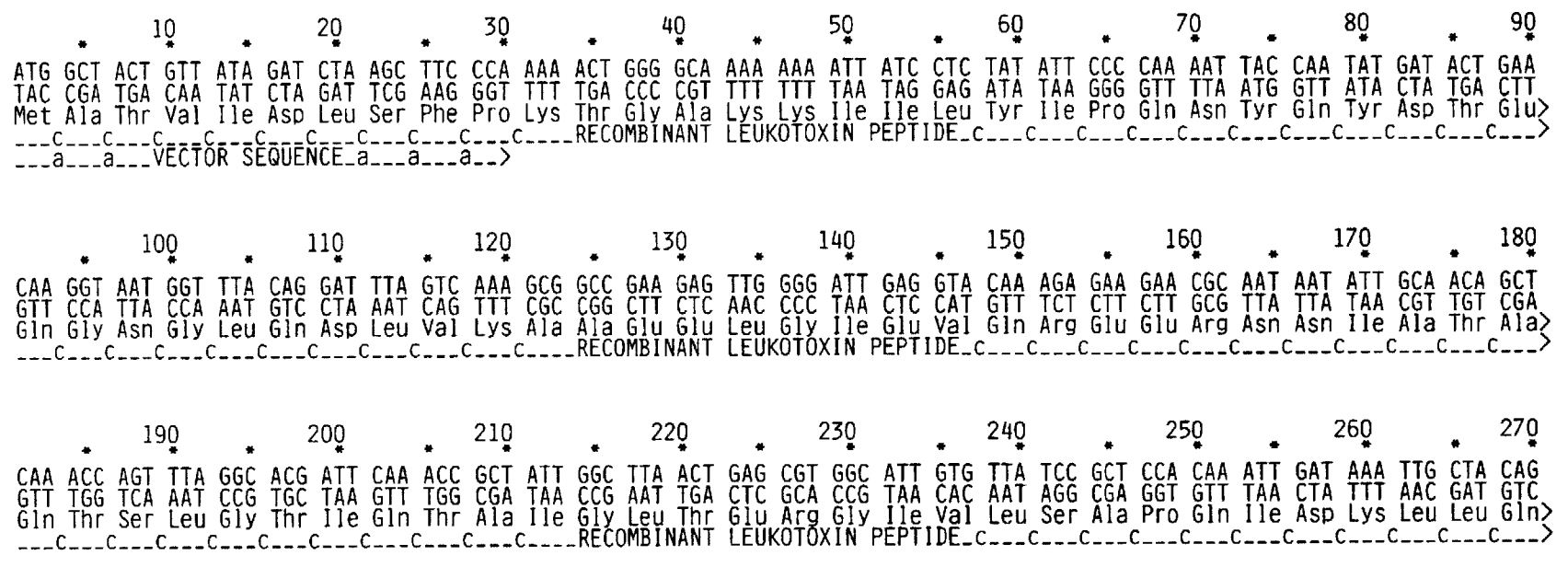
Figure 3B:
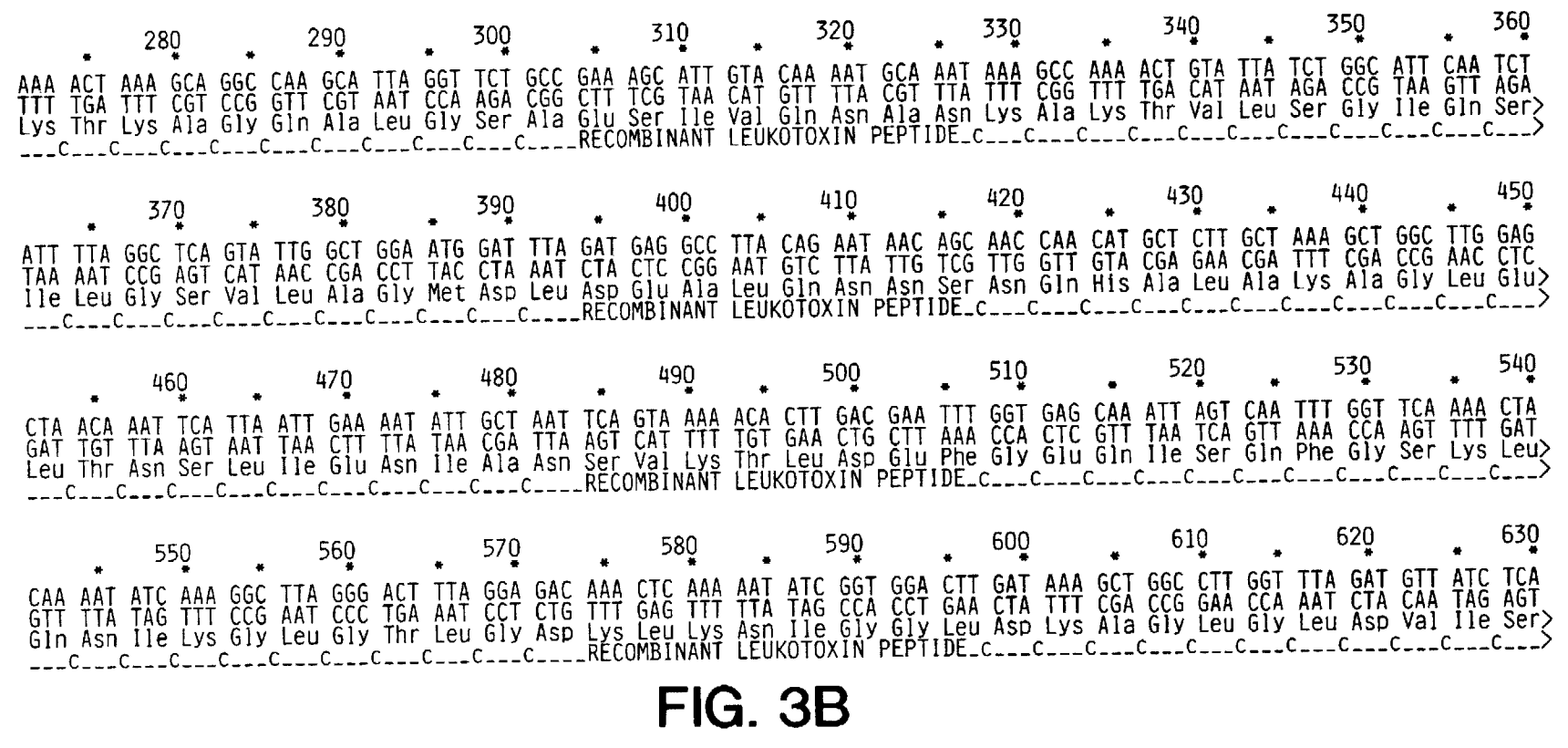
Figure 3C:
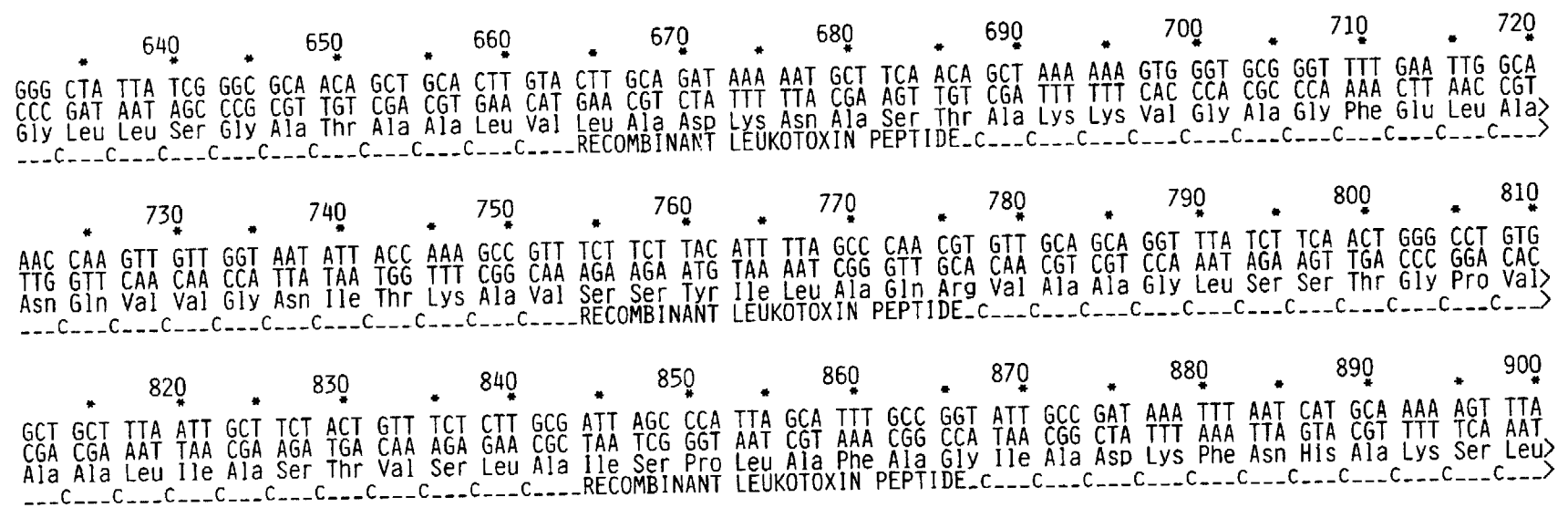
Figure 3D:
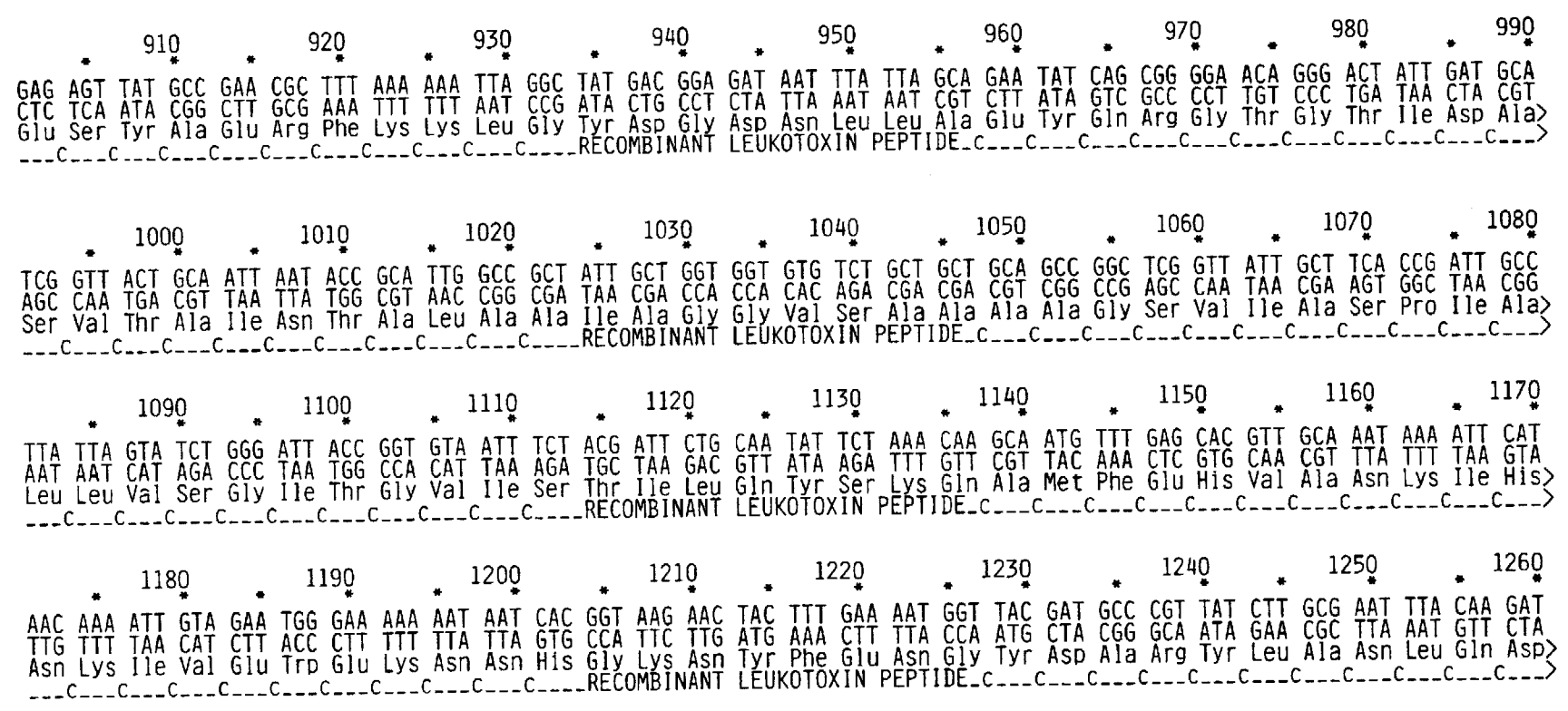
Figure 3E:
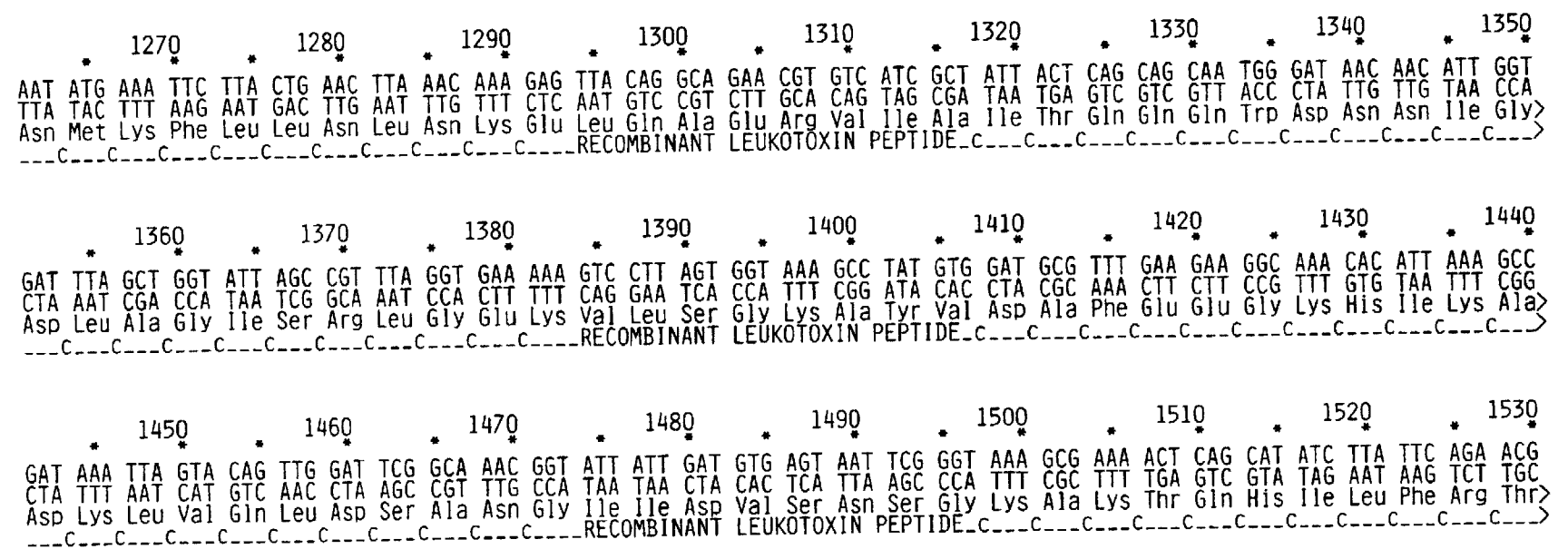
Figure 3F:
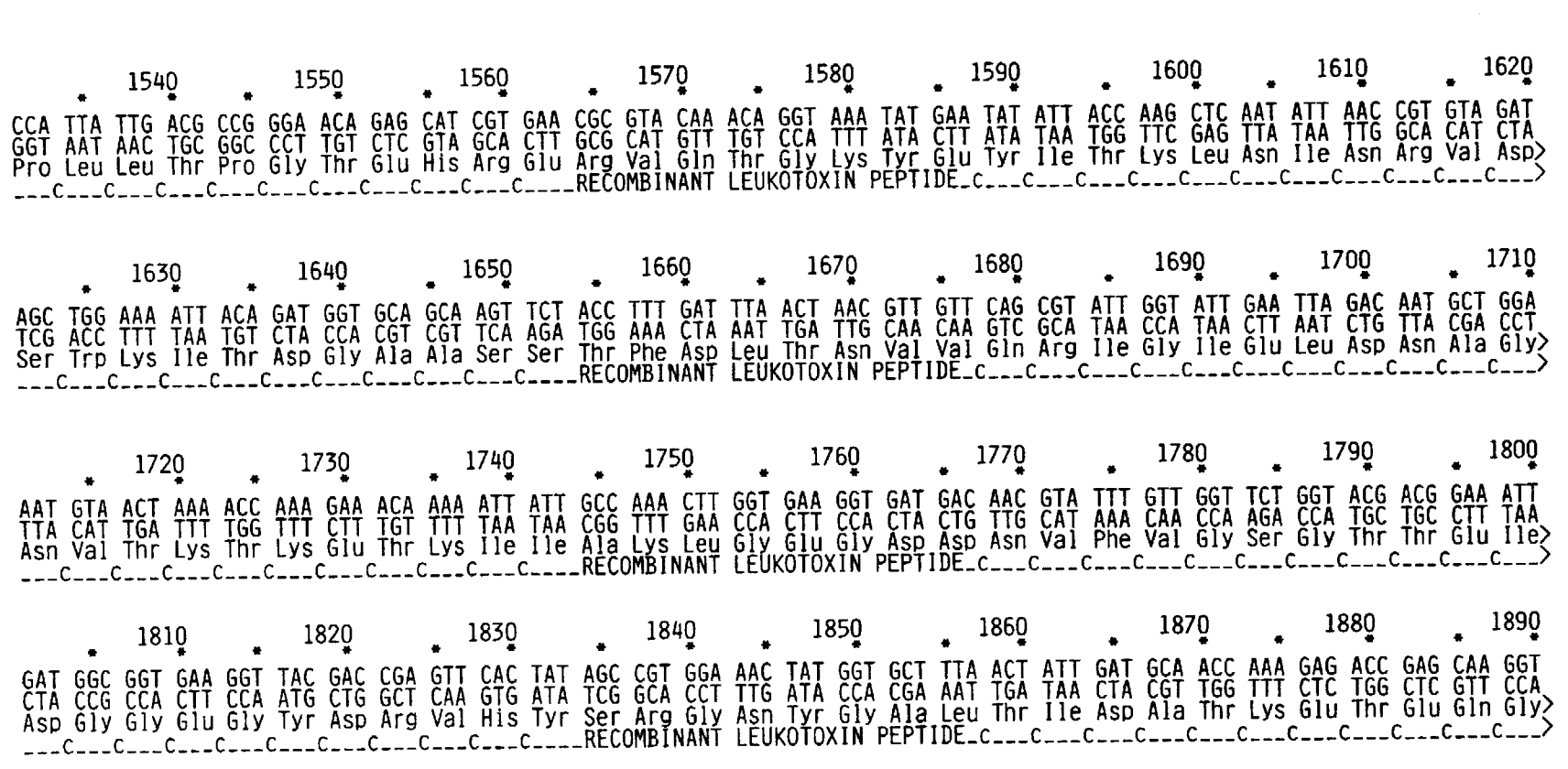
Figure 3G:
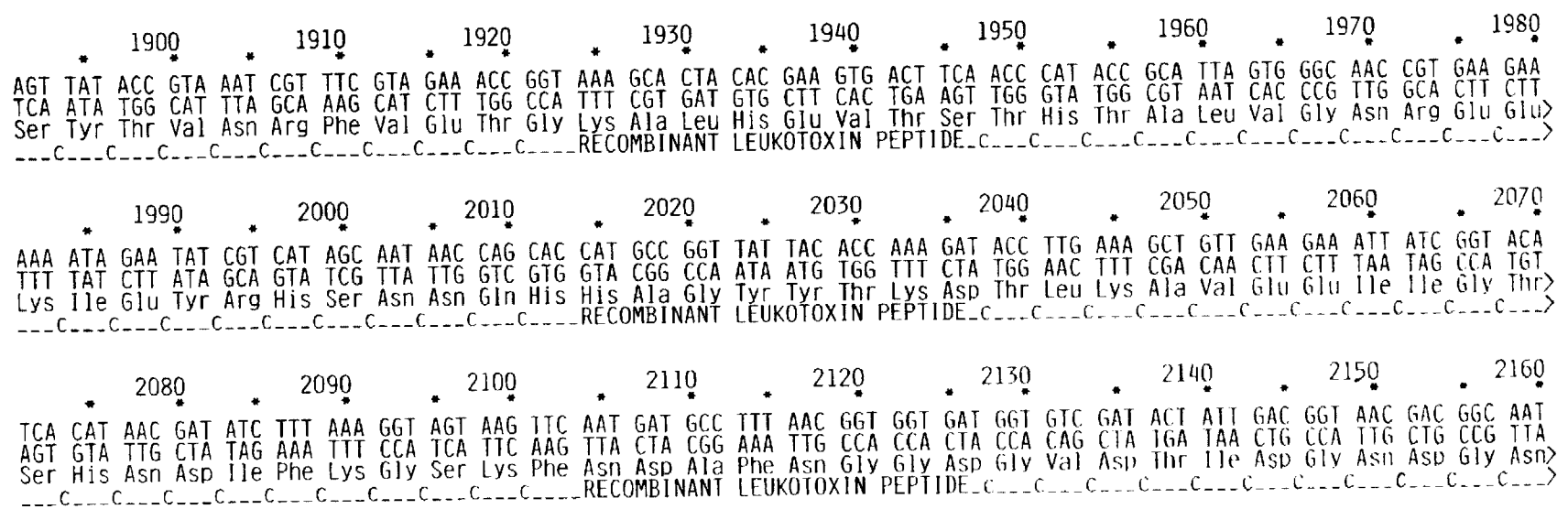
Figure 3H:
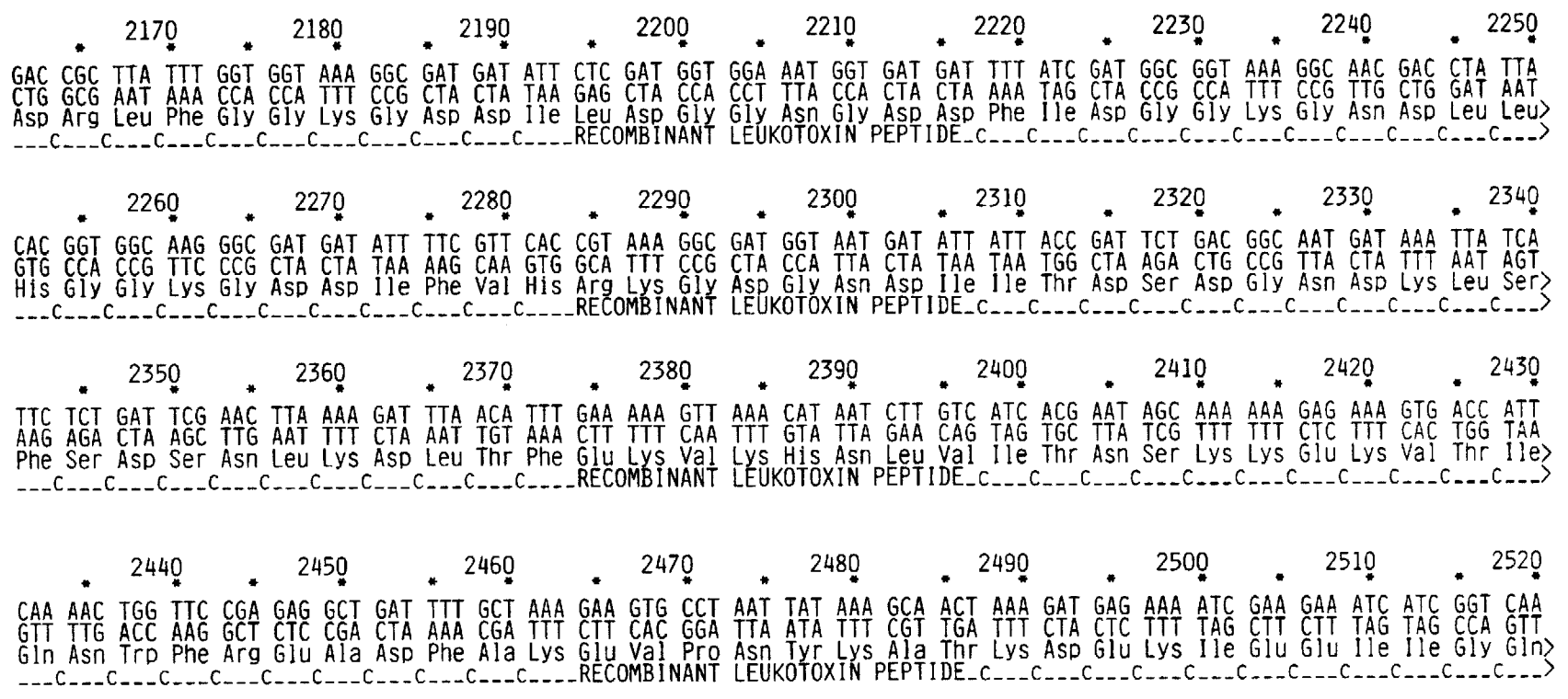
Figure 3I:
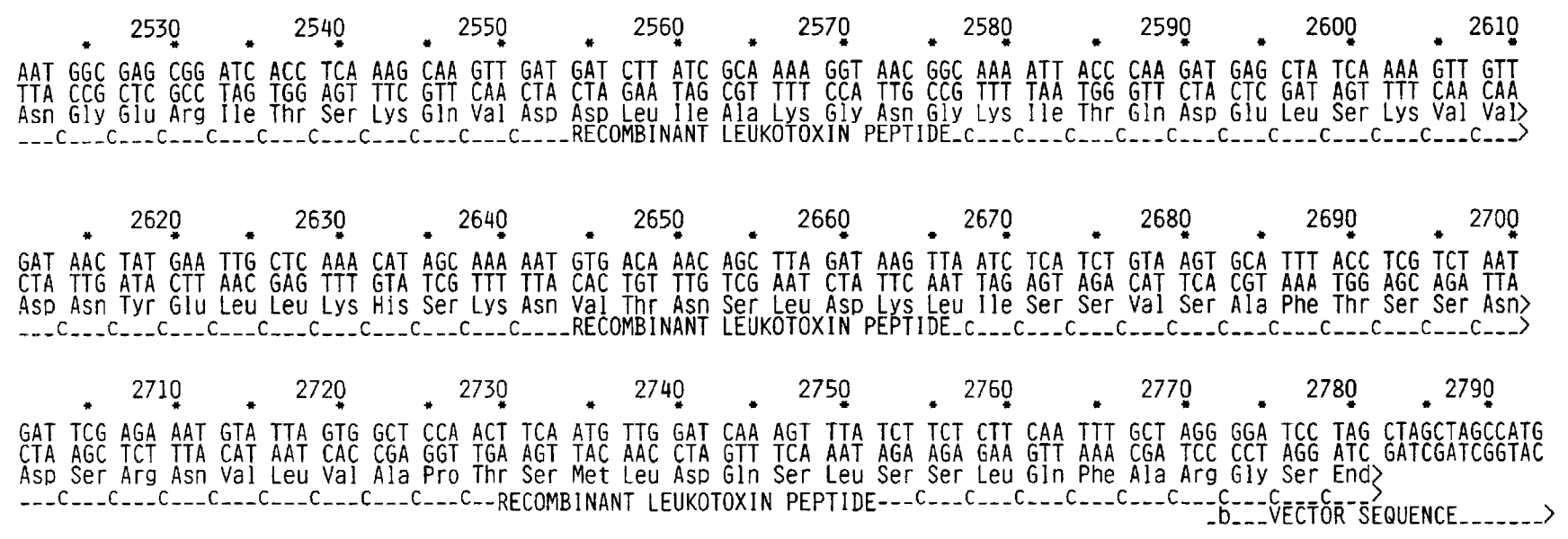

FIGS. 3A through 3I SEQ ID NOS:5–6 show the nucleotide sequence and predicted amino acid sequence of leukotoxin 352 (LKT 352). Both the structural gene for LKT 352 and the sequences of the flanking vector regions are shown.

FIGS. 5A through 5H SEQ ID NOS:7–8 show the nucleotide sequence and predicted amino acid sequence of the LKT-GnRH chimeric protein from pCB113. The nucleotide sequence and predicted amino acid sequence of the LKT-GnRH chimeric protein from pCB112 are identical to the sequences of the chimeric protein derived from pCB113 except that the sequence for multiple copy GnRH was inserted twice as described above in regard to FIG. 4.

FIG. 6 shows the structure of Plasmid pCB111 carrying a leukotoxin-GnRH (LKT-GnRH) gene fusion.

FIGS. 7A through 7E SEQ ID NOS:9–10 show the nucleotide sequence and predicted amino acid sequence of the LKT-GnRH chimeric protein from pCB111. The nucleotide sequence and predicted amino acid sequence of the LKT-GnRH chimeric protein from pCB114 are identical to the sequences of the chimeric protein derived from pCB111 except that the sequence for multiple copy GnRH was inserted twice as described above in regard to FIG. 6.

FIGS. 8A and 8B shows the nucleotide sequence and predicted amino acid sequence of the blunt end fusion point of the truncated leukotoxin gene of plasmid pCB111 (FIG. 8B ) SEQ ID NOS:13–14, where an internal DNA fragment (of approximately 1300 bp in length) was removed from LKT 352 by digestion with the restriction enzymes BstB1 and Nae1 (FIG. 8A) SEQ ID NOS:11–12.

DETAILED DESCRIPTION

Figure 2:
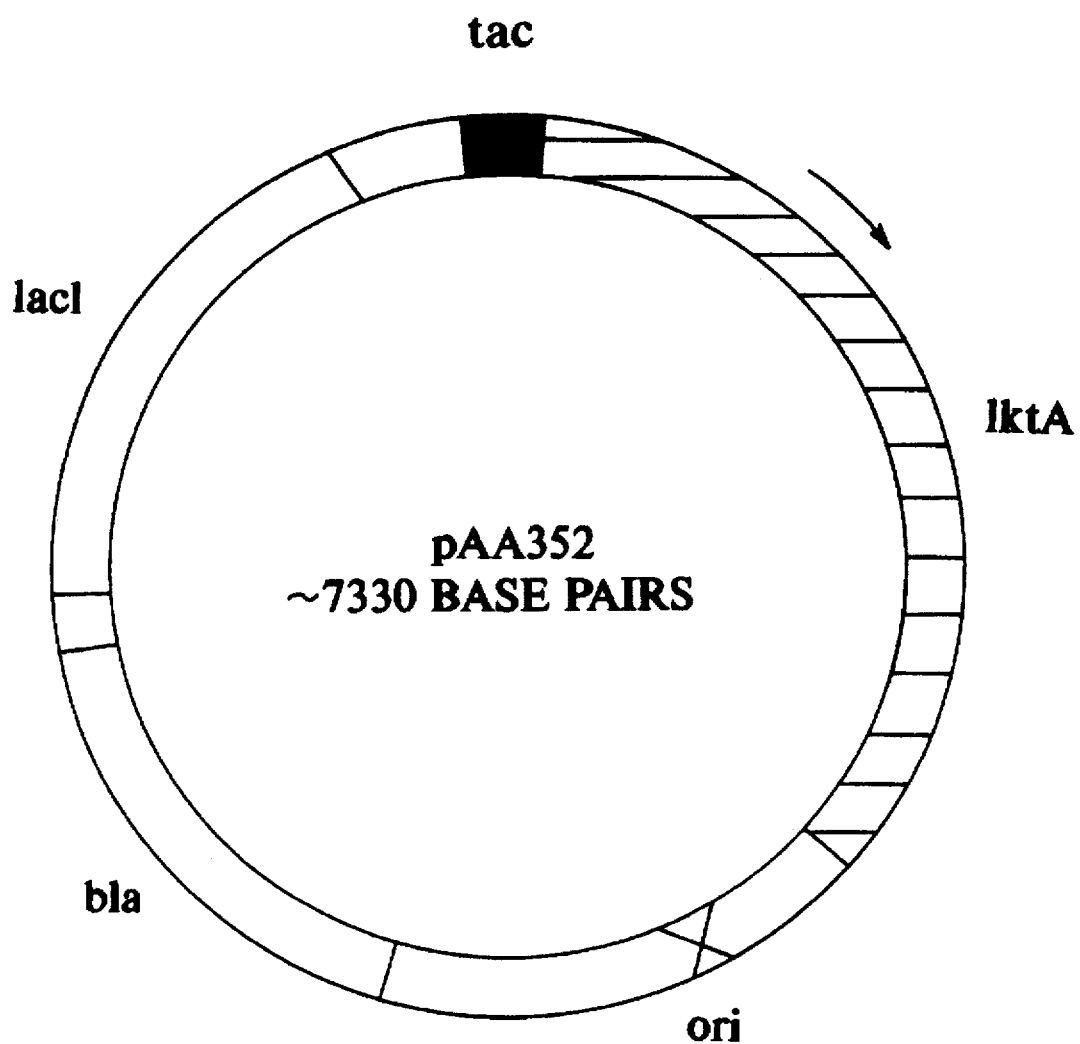
FIG. 2 depicts the structure of Plasmid pAA352 wherein tac is the hybrid trp::lac promoter from *E. coli*; bla represents the β-lactamase gene (ampicillin resistance); ori is the ColE1-based plasmid origin of replication; lktA is the *P. haemolytica* leukotoxin structural gene; and lacI is the *E. coli* lac operon repressor. The direction of transcription/translation of the leukotoxin gene is indicated by the arrow. The size of each component is not drawn to scale.
Figure 4:
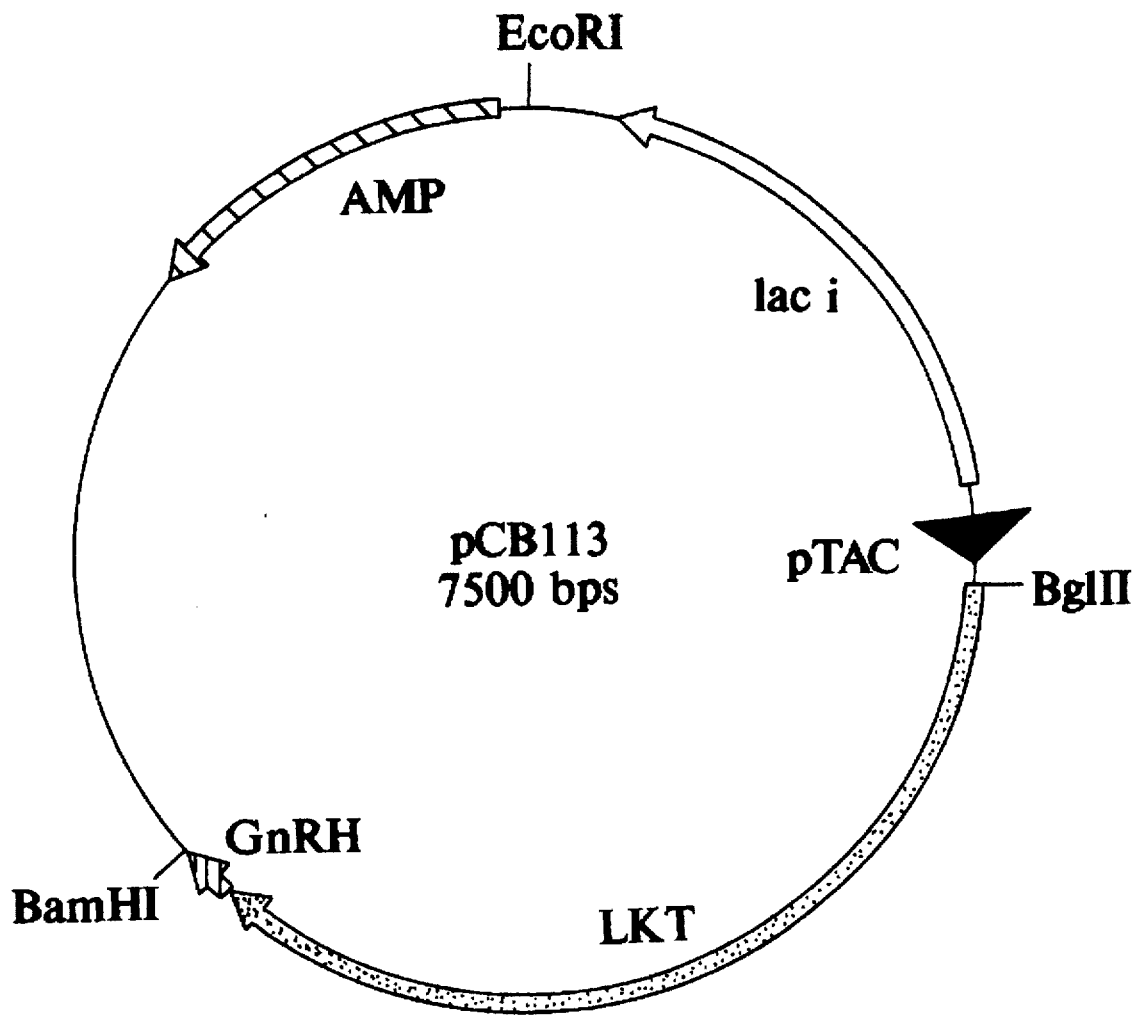
FIG. 4 shows the structure of Plasmid pCB113 carrying a leukotoxin-GnRH (LKT-GnRH) gene fusion.

The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Sambrook, Fritsch & Maniatis, *Molecular Cloning: A Laboratory Manual; DNA Cloning*, Vols. I and II (D. N. Glover ed.) ; *Oligonucleotide Synthesis* (M. J. Gait ed.); *Nucleic Acid Hybridization* (B. D. Hames & S. J. Higgins eds.); *Animal Cell Culture* (R. K. Freshney ed.); *Immobilized Cells and Enzymes* (IRL press); B. Perbal, *A Practical Guide to Molecular Cloning*; the series, *Methods In Enzymology* (S. Colowick and N. Kaplan eds., Academic Press, Inc.); and *Handbook of Experimental Immunology*, Vols. I–IV (D. M. Weir and C. C. Blackwell eds., Blackwell Scientific Publications).

All patents, patent applications, and publications mentioned herein, whether supra or infra, are hereby incorporated by reference in their entirety.

A. Definitions

In describing the present invention, the following terms will be employed, and are intended to be defined as indicated below.

The term "Gonadotropin releasing hormone" or "GnRH" refers to a decapeptide secreted by the hypothalamus which controls release of both luteinizing hormone (LH) and follicle stimulating hormone (FSH) in vertebrates (Fink, G., *British Medical Bulletin* (1979) 35:155–160). The amino acid sequence of GnRH is highly conserved among vertebrates, and especially in mammals. In this regard, GnRH derived from most mammals including human, bovine, porcine and ovine GnRH (formerly designated LHRH) has the amino acid sequence pyroGlu-His-Trp-Ser-Tyr-Gly-Leu-Arg-Pro-Gly-NH$_2$ (Murad et al., *Hormones and Hormone Antagonists*, in *The Pharmacological Basis of Therapeutics*, Sixth Edition (1980) and Seeburg et al., *Nature* (1984) 311:666–668).

As used herein a "GnRH polypeptide" includes a molecule derived from a native GnRH sequence, as well as recombinantly produced or chemically synthesized GnRH polypeptides having amino acid sequences which are substantially homologous to native GnRH and which remain immunogenic, as described below. Thus, the term encompasses derivatives and analogues of GnRH including any single or multiple amino acid additions, substitutions and/or deletions occurring internally or at the amino or carboxy terminuses of the peptide. Accordingly, under the invention, a "GnRH polypeptide" includes molecules having the native sequence, molecules such as that depicted in FIG. 1A (having an N-terminal Gln residue rather than a pyroGlu residue), and molecules with other amino acid additions, substitutions and/or deletions which retain the ability to elicit formation of antibodies that cross react with naturally occurring GnRH. Particularly contemplated herein are repeated sequences of GnRH polypeptides such as in the oligomer depicted in FIG. 1B SEQ ID NOS:4–4 (wherein each of the selected GnRH polypeptides comprises a N-terminal Gln substitution, and further wherein every other GnRH polypeptide comprises an Asp residue substitution at position 2). Epitopes of GnRH are also captured by the definition.

The term "epitope" refers to the site on an antigen or hapten to which a specific antibody molecule binds. Since GnRH is a very small molecule, the identification of epitopes thereof which are able to elicit an antibody response is readily accomplished using techniques well known in the art. See, e.g., Geysen et al. *Proc. Natl. Acad. Sci. USA* (1984) 81:3998–4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al., *Molecular Immunology* (1986) 23:709–715 (technique for identifying peptides with high affinity for a given antibody).

As used herein the term "T-cell epitope" refers to a feature of a peptide structure which is capable of inducing T-cell immunity towards the peptide structure or an associated hapten. In this regard, it is accepted in the art that T-cell epitopes comprise linear peptide determinants that assume extended conformations within the peptide-binding cleft of MHC molecules, (Unanue et al., *Science* (1987) 236:551–557). Conversion of polypeptides to MHC class II-associated linear peptide determinants (generally between 5–14 amino acids in length) is termed "antigen processing" which is carried out by antigen presenting cells (APCs). More particularly, a T-cell epitope is defined by local features of a short peptide structure, such as primary amino acid sequence properties involving charge and hydrophobicity, and certain types of secondary structure, such as helicity, that do not depend on the folding of the entire polypeptide. Further, it is believed that short peptides capable of recognition by helper T-cells are generally amphipathic structures comprising a hydrophobic side (for interaction with the MHC molecule) and a hydrophilic side (for interacting with the T-cell receptor), (Margalit et al., *Computer Prediction of T-cell Epitopes, New Generation Vaccines* Marcel-Dekker, Inc. ed. G. C. Woodrow et al., (1990) pp. 109–116) and further that the amphipathic structures have an α-helical configuration (see, e.g., Spouge et al., *J. Immunol.* (1987) 138:204–212; Berkower et al., *J. Immunol.*(1986) 136:2498–2503).

Hence, segments of proteins which include T-cell epitopes can be readily predicted using numerous computer programs. (See e.g., Margalit et al., *Computer Prediction of T-cell Epitopes, New Generation Vaccines* Marcel-Dekker, Inc. ed. G. C. Woodrow et al., (1990) pp. 109–116). Such programs generally compare the amino acid sequence of a peptide to sequences known to induce a T-cell response, and search for patterns of amino acids which are believed to be required for a T-cell epitope.

An "immunogenic protein" or "immunogenic amino acid sequence" is a protein or amino acid sequence, respectively, which elicits an immunological response in a subject to which it is administered. Under the invention, a "GnRH immunogen" refers to a GnRH molecule which, when introduced into a host subject, stimulates an immune response. In this regard, a GnRH immunogen includes a multimer corresponding to more than one selected GnRH polypeptide sequence; and, more, particularly, to a multimer having either multiple or tandem repeats of selected GnRH polypeptide sequences, multiple or tandem repeats of selected GnRH epitopes, or any conceivable combination thereof.

An "immunological response" to an antigen or vaccine is the development in the host of a cellular and/or antibody-mediated immune response to the composition or vaccine of interest. Usually, such a response includes but is not limited to one or more of the following effects; the production of antibodies, B cells, helper T cells, suppressor T cells, and/or cytotoxic T cells and/or γδ T cells, directed specifically to an antigen or antigens included in the composition or vaccine of interest. An immunological response can be detected using any of several immunoassays well known in the art.

The term "leukotoxin polypeptide" or "LKT polypeptide" intends a polypeptide which includes at least one T-cell epitope and is derived from a protein belonging to the family of molecules characterized by the carboxy-terminus consensus amino acid sequence Gly-Gly-X-Gly-X-Asp SEQ ID NO:15 (Highlander et al., *DNA* (1989) 8:15–28), where X is Lys, Asp, Val or Asn. Such proteins include, among others, leukotoxins derived from *P. haemolytica* and *Actinobacillus pleuropneumoniae*, as well as *E. coli* alpha hemolysin (Strathdee et al., *Infect. Immun.* (1987) 55:3233–3236; Lo, *Can. J. Vet. Res.* (1990) 54:S33–S35; Welch, *Mol. Microbiol.* (1991) 5:521–528). This family of toxins is known as the "RTX" family of toxins (Lo, *Can. J. Vet. Res.* (1990) 54:S33–S35). In addition, the term "leukotoxin polypeptide" refers to a leukotoxin polypeptide which is chemically synthesized, isolated from an organism expressing the same, or recombinantly produced. Furthermore, the term intends an immunogenic protein having an amino acid sequence substantially homologous to a contiguous amino acid sequence found in the particular native leukotoxin molecule. Thus, the term includes both full-length and partial sequences, as well as analogues. Although native full-length leukotoxins display leukotoxic activity, the term "leukotoxin" also intends molecules which remain immunogenic yet lack the cytotoxic character of native leukotoxins. The nucleotide sequences and corresponding amino acid sequences for several leukotoxins are known. See, e.g., U.S. Pat. Nos. 4,957,739 and 5,055,400; Lo et al., *Infect. Immun.* (1985) 50:667–67; Lo et al., *Infect. Immun.* (1987) 55:1987–1996; Strathdee et al., *Infect. Immun.* (1987) 55:3233–3236; Highlander et al., *DNA* (1989) 8:15–28; Welch, *Mol. Microbiol.* (1991) 5:521–528. In the chimeras produced according to the present invention, a selected Leukotoxin polypeptide sequence imparts enhanced immunogenicity to a fused GnRH multimer by providing, among other things, T-cell epitopes comprising small peptide segments in the range of five to fourteen amino acids in length which are capable of complexing with MHC class II molecules for presentation to, and activation of, T-helper cells. As discussed further below, these T-cell epitopes occur throughout the leukotoxin molecule and are thought to be concentrated in the N-terminus portions of leukotoxin, i.e., between amino acid residues 1 to 199.

As used herein, a leukotoxin polypeptide "which lacks leukotoxic activity" refers to a leukotoxin polypeptide as described above which lacks significant cytotoxicity as compared to a native, full-length leukotoxin (such as the full-length *P. haemolytica* leukotoxin described in U.S. Pat. Nos. 5,055,400 and 4,957,739) yet still retains immunogenicity and at least one T-cell epitope. Leukotoxin polypeptides can be tested for leukotoxic activity using any of several known assays such as the lactate dehydrogenase release assay, described by Korzeniewski et al., *Journal of Immunological Methods* 64:313–320, wherein cytotoxicity is measured by the release of lactate dehydrogenase from bovine neutrophils. A molecule is identified as leukotoxic if it causes a statistically significant release of lactate dehydrogenase when compared to a control non-leukotoxic molecule.

Under the invention, construction of LKT-GnRH chimeras comprising leukotoxin polypeptides which lack leukotoxic activity provides several important benefits. Initially, a leukotoxin polypeptide which lacks leukotoxic activity is desirable since the injection of an active toxin into a subject can result in localized cell death (PMNs and macrophages) and, in turn, cause a severe inflammatory response and abscess at the injection site. In this regard, leukotoxic activity resulting in the killing of macrophages may lead to reduced antigen presentation and hence a suboptimal immune response. The removal of the cytotoxic portion as found in the non-leukotoxic LKT polypeptides used in producing the fusion proteins of the invention also results in a truncated LKT gene which is capable of being expressed at much higher levels than full-length LKT. Further, the use of non-leukotoxic LKT polypeptides in the fusions constructed under the present invention which retain sufficient T-cell antigenicity reduces the overall amount of leukotoxin-GnRH antigen which needs to be administered to a host subject to yield a sufficient B-cell response to the selected GnRH polypeptides. Particular examples of immunogenic leukotoxin polypeptides which lack leukotoxic activity include LKT 352 and LKT 111 which are described in greater detail below.

By "LKT 352" is meant a protein which is derived from the lktA gene present in plasmid pAA352 (FIG. 2, ATCC Accession No. 68283). The nucleotide sequence and corresponding amino acid sequence of this gene are described in International Publication No. WO91/15237 and are shown in FIGS. 3A–3I SEQ ID NOS:5–6. The gene encodes a truncated leukotoxin, having 931 amino acids and an estimated molecular weight of around 99 kDa, which lacks the cytotoxic portion of the molecule. The truncated gene thus produced is expressed at much higher levels than the full-length molecule (more than 40% of total cell protein versus less than 1% of total cell protein for the full-length form) and is more easily purified. Under the invention, the derived LKT 352 is not necessarily physically derived from the sequence present in plasmid pAA352. Rather, it may be generated in any manner, including for example, by chemical synthesis or recombinant production. In addition, the amino acid sequence of the protein need only be substantially homologous to the depicted sequence. Thus, sequence variations may be present so long as the LKT polypeptide functions to enhance the immunogenicity of antigen with which it is associated yet also lacks leukotoxic activity.

Figures 5H, 6:
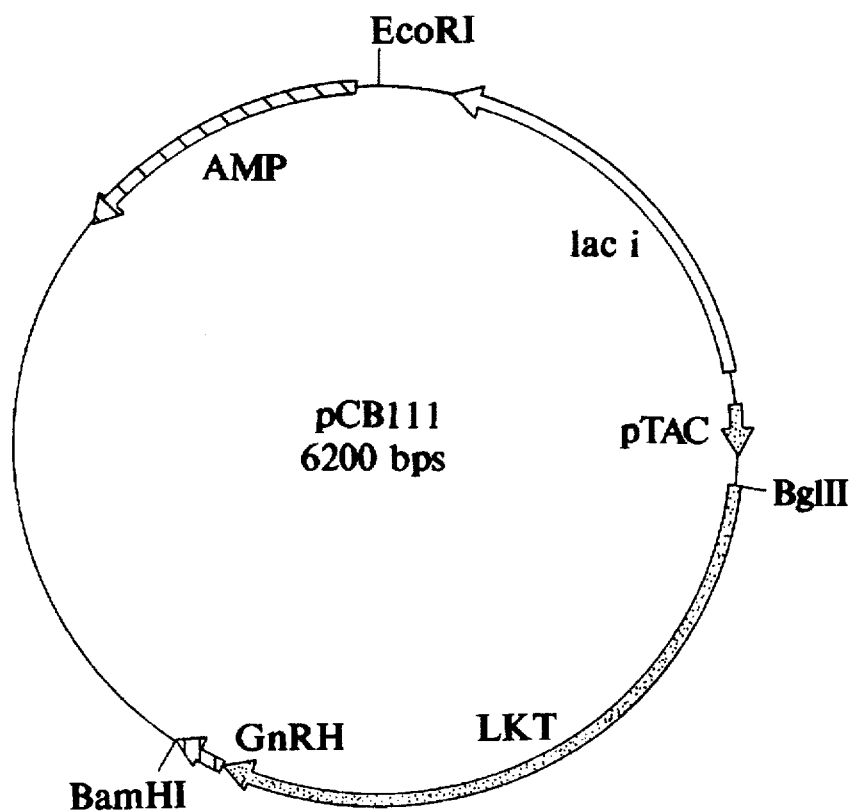

By "LKT 111" is meant a leukotoxin polypeptide which is derived from gene present in plasmid pCB111 (FIG. 6, ATCC Accession No. 69748). The nucleotide sequence of this gene and the corresponding amino acid sequence are shown in FIGS. 7A–7E SEQ ID NOS:9–10. The gene encodes a shortened version of leukotoxin which was developed from the recombinant leukotoxin gene present in plasmid pAA352 (FIG. 2, ATCC Accession No. 68283) by removal of an internal DNA fragment of approximately 1300 bp in length. The LKT 111 polypeptide has an estimated molecular weight of 52 kDa (as compared to the 99 kDa LKT 352 polypeptide), but retains portions of the N-terminus from LKT 352 containing T-cell epitopes which are necessary for sufficient T-cell immunogenicity and portions from the C-terminus from LKT 352 containing convenient restriction sites for use in producing the fusion proteins of the present invention. Under the invention, the LKT 111 leukotoxin peptide is not necessarily physically derived from the sequence present in plasmid pCB111. Rather, it may be generated in any manner, including for example, by chemical synthesis or recombinant production. In addition, the amino acid sequence of the protein need only be substantially homologous to the depicted sequence. Thus, sequence variations may be present so long as the protein functions to enhance the immunogenicity of antigen with which it is associated and lacks leukotoxicity.

A leukotoxin-GnRH polypeptide chimera displays "increased immunogenicity" when it possesses a greater capacity to elicit an immune response than the corresponding GnRH multimer alone. Such increased immunogenicity can be determined by administering the particular leukotoxin-GnRH polypeptide and GnRH multimer controls to animals and comparing antibody titres against the two using standard assays such as radioimmunoassays and ELISAs, well known in the art.

"Recombinant" proteins or polypeptides refer to polypeptides produced by recombinant DNA techniques; i.e., produced from cells transformed by an exogenous DNA construct encoding the desired polypeptide. "Synthetic" proteins or polypeptides are those prepared by chemical synthesis.

A DNA "coding sequence" or a "nucleotide sequence encoding" a particular protein, is a DNA sequence which is transcribed and translated into a polypeptide in vivo or in vitro when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

DNA "control sequences" refer collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence is "operably linked to" another coding sequence when RNA polymerase will transcribe the two coding sequences into mRNA, which is then translated into a chimeric polypeptide encoded by the two coding sequences. The coding sequences need not be contiguous to one another so long as the transcribed sequence is ultimately processed to produce the desired chimeric protein. A control sequence is "operably linked to" a coding sequence when it controls the transcription of the coding sequence.

A control sequence "directs the transcription" of a coding sequence in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) to chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cell containing the exogenous DNA.

Two DNA or polypeptide sequences are "substantially homologous" when at least about 80% (preferably at least about 90%, and most preferably at least about 95%) of the nucleotides or amino acids match over a defined length of the molecule. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, vols I & II, supra; *Nucleic Acid Hybridization*, supra.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

By "vertebrate subject" is meant any member of the subphylum chordata, including, without limitation, mammals such as rodents, cattle, pigs, sheep, goats, horses and man; domestic animals such as dogs and cats; birds, including domestic, wild and game birds such as cocks and hens including chickens, turkeys and other gallinaceous birds. The term does not denote a particular age. Thus, both adult and newborn animals are intended to be covered.

B. General Methods

Central to the instant invention is the discovery that leukotoxin polypeptides, when coupled to selected GnRH polypeptide repeats (or multimers), are able to confer superior immunogenicity to the associated GnRH moieties. In this regard, leukotoxin polypeptides act as carrier proteins which present selected GnRH multimers to a subject's immune system in a highly immunogenic form. Thus, chimeric proteins constructed under the invention may be formulated into vaccine compositions which provide enhanced immunogenicity to GnRH polypeptides presented therewith. Fusion of the leukotoxin gene to selected GnRH polypeptides also facilitates purification of the chimeric protein from cells expressing the same.

Accordingly, exemplified herein are leukotoxin chimeras which include leukotoxin fused to more than one GnRH peptide sequence. Particularly contemplated embodiments of the present invention include chimeras comprising a leukotoxin polypeptide fused to a GnRH multimer, wherein said multimer consists essentially of at least one repeating GnRH decapeptide sequence, or at least one repeating unit of a sequence corresponding to at least one epitope of a selected GnRH molecule. Further, the selected GnRH peptide sequences may all be the same, or may correspond to different derivatives, analogues, variants or epitopes of GnRH so long as they retain the ability to elicit an immune response. A representative nucleotide sequence of a GnRH decapeptide is depicted in FIG. 1A SEQ ID NOS:1–2. The subject GnRH sequence is modified by the substitution of a glutamine residue at the N-terminal in place of pyroglutamic acid which is found in the native sequence. This particular substitution renders a molecule that retains the native glutamic acid structure but also preserves the uncharged structure of pyroglutamate. Accordingly, the resulting peptide does not require cyclization of the glutamic acid residue and may be produced in the absence of conditions necessary to effect cyclization.

Because the GnRH sequence is relatively short, it can easily be generated using synthetic techniques, as described in detail below. Under the invention, a leukotoxin polypeptide sequence is used to confer immunogenicity upon associated GnRH polypeptides (as a carrier protein) in order to help elicit an adequate immune response toward endogenous GnRH in a vertebrate subject. In this manner, immunization with GnRH can regulate fertility in a vaccinated subject by disruption of estrous cycles or spermatogenesis. A detailed discussion of GnRH can be found in U.S. Pat. No. 4,975,420, which is incorporated herein by reference in its entirety.

Further, it is particularly contemplated herein to provide a reliable and effective alternative to invasive sterilization procedures currently practiced in domestic and farm animal husbandry, such as surgical castration, surgical ovariohysterectomy and the like. Immunosuppression of reproductive activity in vertebrate subjects using leukotoxin-GnRH chimeras constructed according to the present invention provides an effective alternative in that the constructs effect uniform inactivation of reproductive activity in immunized animals. In this regard, a suitable sterilization vaccine product must serve to uniformly inactivate reproductive capabilities in individual animals in response to a minimum of vaccinations in order to provide a successful alternative to surgical procedures. This feature is particularly important for immunosterilization of herd animals, and particularly where it is desired to immunocastrate male piglets to prevent "boar taint" which is produced by the synthesis of sex steroids in normally functioning testicles of male piglets. See e.g. Meloen et al., *Vaccine* (1994) 12(8):741–746. Prior attempts at developing such a product have not produced uniform results due to the insufficient immunogenicity of GnRH peptides and/or related carrier systems, and the resultant inability of various prior GnRH-based vaccines to induce sufficient immune responses toward endogenous GnRH.

Accordingly, leukotoxin-GnRH polypeptide chimeras contemplated herein comprise a GnRH portion that corresponds to more than one selected GnRH polypeptide sequence in order to render a more immunogenic GnRH peptide antigen. This feature is based on the recognition that endogenous proteins in general may be rendered effective autoantigens by multimerization of their epitopes as described in detail above. More particularly, the GnRH portion of the novel chimeras contemplated herein may comprise either multiple or tandem repeats of selected GnRH sequences, multiple or tandem repeats of selected GnRH epitopes, or any conceivable combination thereof. In this regard, GnRH epitopes may be identified using techniques as described in detail above, or fragments of GnRH proteins may be tested for immunogenicity and active fragments used in compositions in lieu of the entire polypeptide. The sequence of a particularly contemplated GnRH portion under the present invention is depicted in FIG. 1B SEQ ID NOS:3–4 wherein four GnRH sequences, indicated at (1), (2), (3) and (4) respectively, are separated by triplet amino acid spacer sequences comprising various combinations of serine and glycine residues. In the subject oligomer, every other GnRH sequence (those indicated at (2) and (4), respectively) contains a non-conservative amino acid substitution at the second position of the GnRH decapeptide comprising an Asp residue in place of the His residue found in the native GnRH sequence. The alternating GnRH multimeric sequence thus produced renders a highly immunogenic GnRH antigen peptide for use in the fusion proteins of the invention. Other GnRH analogues corresponding to any single or multiple amino acid additions, substitutions and/or deletions are also particularly contemplated herein for use in either repetitive or alternating multimeric sequences.

Furthermore, the particular GnRH portion depicted in FIG. 1B SEQ ID NOS:3–4 contains spacer sequences between the GnRH moieties. The present invention particularly contemplates the strategic use of various spacer sequences between selected GnRH polypeptides in order to confer increased immunogenicity on the subject constructs. Accordingly, under the invention, a selected spacer sequence may encode a wide variety of moieties of one or more amino acids in length. Selected spacer groups may preferably provide enzyme cleavage sites so that the expressed chimera can be processed by proteolytic enzymes in vivo (by APC's or the like) to yield a number of peptides-each of which contain at least one T-cell epitope derived from the carrier portion (leukotoxin portion)—and which are preferably fused to a substantially complete GnRH polypeptide sequence. Further, spacer groups may be constructed so that the junction region between selected GnRH moieties comprises a clearly foreign sequence to the immunized subject, thereby conferring enhanced immunogenicity upon the associated GnRH peptides. Additionally, spacer sequences may be constructed so as to provide T-cell antigenicity, such as sequences which encode amphipathic and/or α-helical peptide sequences which are generally regarded in the art as providing immunogenic helper T-cell epitopes. In this regard, the choice of particular T-cell epitopes to be provided by such spacer sequences may vary depending on the particular vertebrate species to be vaccinated. Although, particular GnRH portions are exemplified which include spacer sequences, it is also contemplated herein to provide a GnRH multimer comprising directly adjacent GnRH sequences (without intervening spacer sequences).

The leukotoxin-GnRH polypeptide complex can be conveniently produced recombinantly as a chimeric protein. The GnRH portion of the chimera can be fused either 5' or 3' to the leukotoxin portion of the molecule, or the GnRH portion may be located at sites internal to the leukotoxin molecule. The nucleotide sequence coding for full-length *P. haemolytica* A1 leukotoxin has been determined. See, e.g., Lo, *Infect. Immun.* (1987) 55:1987–1996; U.S. Pat. No. 5,055,400, incorporated herein by reference in its entirety. Additionally, several variant leukotoxin gene sequences are disclosed herein.

Similarly, the coding sequences for porcine, bovine and ovine GnRH have been determined. (Murad et al., *Hormones and Hormone Antagonists*, in *The Pharmacological Basis of Therapeutics*, Sixth Edition (1980)), and the cDNA for human GnRH has been cloned so that its sequence has been well established (Seeburg et al., *Nature* (1984) 311:666–668). Additional GnRH polypeptides of known sequences have been disclosed, such as the GnRH molecule occurring in salmon and chickens (International Publication No. WO 86/07383, published 18 Dec. 1986). In this regard, it is noted that GnRH is highly conserved in vertebrates, particularly in mammals; and further that porcine, bovine, ovine and human GnRH sequences are identical to one another. The desired leukotoxin and GnRH genes can be cloned, isolated and ligated together using recombinant techniques generally known in the art. See, e.g., Sambrook et al., supra.

Alternatively, DNA sequences encoding the chimeric proteins can be prepared synthetically rather than cloned. The DNA sequence can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature* (1981) 292:756; Nambair et al. *Science* (1984) 223:1299; Jay et al. *J. Biol. Chem.* (1984) 259:6311.

Once coding sequences for the chimeric proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage lambda (*E. coli*), pBR322 (*E. coli*), pACYC177 (*E. coli*), pKT230

(gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) and bovine papilloma virus (mammalian cells). See, generally, *DNA Cloning*: Vols. I & II, supra; T. Maniatis et al., supra; B. Perbal, supra.

The fusion gene can be placed under the control of a promoter, ribosome binding site (for bacterial expression) and, optionally, an operator (collectively referred to herein as "control" elements), so that the DNA sequence encoding the chimeric protein is transcribed into RNA in the host cell transformed by a vector containing this expression construction. The coding sequence may or may not contain a signal peptide or leader sequence. The chimeric proteins of the present invention can be expressed using, for example, native *P. haemolytica* promoter, the *E. coli* tac promoter or the protein A gene (spa) promoter and signal sequence. Leader sequences can be removed by the bacterial host in post-translational processing. See, e.g., U.S. Pat. Nos. 4,431,739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular fusion coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular chimeric protein of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to add sequences which cause the secretion of the polypeptide from the host organism, with subsequent cleavage of the secretory signal. It may also be desirable to produce mutants or analogues of the chimeric proteins of interest. Mutants or analogues may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., T. Maniatis et al., supra; *DNA Cloning*, Vols. I and II, supra; *Nucleic Acid Hybridization*, supra.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; 96,491.

Depending on the expression system and host selected, the proteins of the present invention are produced by growing host cells transformed by an expression vector described above under conditions whereby the protein of interest is expressed. The chimeric protein is then isolated from the host cells and purified. If the expression system secretes the protein into growth media, the protein can be purified directly from the media. If the protein is not secreted, it is isolated from cell lysates. The selection of the appropriate growth conditions and recovery methods are within the skill of the art.

The chimeric proteins of the present invention may also be produced by chemical synthesis such as solid phase peptide synthesis, based on the determined amino acid sequences. Such methods are known to those skilled in the art. See, e.g., J. M. Stewart and J. D. Young, *Solid Phase Peptide Synthesis*, 2nd Ed., Pierce Chemical Co., Rockford, Ill. (1984) and G. Barany and R. B. Merrifield, *The Peptides: Analysis, Synthesis, Biology*, editors E. Gross and J. Meienhofer, Vol. 2, Academic Press, New York, (1980), pp. 3–254, for solid phase peptide synthesis techniques; and M. Bodansky, *Principles of Peptide Synthesis*, Springer-Verlag, Berlin (1984) and E. Gross and J. Meienhofer, Eds., *The Peptides: Analysis, Synthesis, Biology*, supra, Vol. 1, for classical solution synthesis.

Subjects can be immunized with chimeric proteins constructed according to the present invention by administration of vaccine compositions which include said proteins. Prior to immunization, it may be desirable to further increase the immunogenicity of the particular chimeric protein. This can be accomplished in any one of several ways known to those of skill in the art. For example, the leukotoxin-GnRH polypeptide fusion protein may be administered linked to a secondary carrier. For example, a fragment may be conjugated with a macromolecular carrier. Suitable carriers are typically large, slowly metabolized macromolecule such as: proteins; polysaccharides, such as sepharose, agarose, cellulose, cellulose beads and the like; polymeric amino acids such as polyglutamic acid, polylysine, and the like; amino acid copolymers; and in-active virus particles. Especially useful protein substrates are serum albumins, keyhole limpet hemocyanin, immunoglobulin molecules, thyroglobulin, ovalbumin, and other proteins well known to those skilled in the art.

The protein substrates may be used in their native form or their functional group content may be modified by, for example, succinylation of lysine residues or reaction with Cys-thiolactone. A sulfhydryl group may also be incorporated into the carrier (or selected GnRH polypeptides) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

Other suitable carriers for the chimeric proteins of the present invention include VP6 polypeptides of rotaviruses, or functional fragments thereof, as disclosed in U.S. Pat. No. 5,071,651, and incorporated herein by reference. Also useful is a fusion product of a viral protein and a leukotoxin-GnRH immunogen, where that fusion product is made by methods disclosed in U.S. Pat. No. 4,722,840. Still other suitable carriers include cells, such as lymphocytes, since presentation in this form mimics the natural mode of presentation in the subject, which gives rise to the immunized state. Alternatively, the fusion proteins of the present invention may be coupled to erythrocytes, preferably the subject's own erythrocytes. Methods of coupling peptides to proteins or cells are known to those of skill in the art.

The novel chimeric proteins of the instant invention can also be administered via a carrier virus which expresses the same. Carrier viruses which will find use with the instant invention include but are not limited to the vaccinia and other pox viruses, adenovirus, and herpes virus. By way of example, vaccinia virus recombinants expressing the novel chimeric proteins can be constructed as follows. The DNA encoding the particular leukotoxin-GnRH chimeric protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant chimeric protein into the viral genome. The resulting TK-recombinant can be selected by culturing the cells in the presence of 5-bromodeoxyuridine and picking viral plaques resistant thereto.

It is also possible to immunize a subject with chimeric proteins produced according to the present invention, either administered alone, or mixed with a pharmaceutically acceptable vehicle or excipient. Typically, vaccines are prepared as injectables, either as liquid solutions or suspensions; solid forms suitable for solution in, or suspension in, liquid vehicles prior to injection may also be prepared. The preparation may also be emulsified or the active ingredient encapsulated in liposome vehicles. The active immunogenic ingredient is often mixed with vehicles containing excipients which are pharmaceutically acceptable and compatible with the active ingredient. Suitable vehicles are, for example, water, saline, dextrose, glycerol, ethanol, or the like, and combinations thereof. In addition, if desired, the vehicle may contain minor amounts of auxiliary substances such as wetting or emulsifying agents, pH buffering agents, or adjuvants which enhance the effectiveness of the vaccine. Adjuvants may include for example, muramyl dipeptides, avridine, aluminum hydroxide, oils, saponins and other substances known in the art. Actual methods of preparing such dosage forms are known, or will be apparent, to those skilled in the art. See, e.g., *Remington's Pharmaceutical Sciences*, Mack Publishing Company, Easton, Pa., 18th edition, 1990. The composition or formulation to be administered will, in any event, contain a quantity of the protein adequate to achieve the desired immunized state in the subject being treated.

Additional vaccine formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 1% to about 30% of the active ingredient, preferably about 2% to about 20%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the chimeric proteins into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. The chimeric proteins can also be presented using implanted mini-pumps, well known in the art.

Furthermore, the chimeric proteins (or complexes thereof) may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

To immunize a subject, a selected GnRH-leukotoxin chimera is administered parenterally, usually by intramuscular injection in an appropriate vehicle. Other modes of administration, however, such as subcutaneous, intravenous injection and intranasal delivery, are also acceptable. Injectable vaccine formulations will contain an effective amount of the active ingredient in a vehicle, the exact amount being readily determined by one skilled in the art. The active ingredient may typically range from about 1% to about 95% (w/w) of the composition, or even higher or lower if appropriate. The quantity to be administered depends on the animal to be treated, the capacity of the animal's immune system to synthesize antibodies, and the degree of protection desired.

With the present vaccine formulations, approximately 1 μg to 1 mg, more generally 5 μg to 200 μg of GnRH polypeptide per ml of injected solution, should be adequate to raise an immunological response when administered. In this regard, the ratio of GnRH to leukotoxin in the Leukotoxin-GnRH antigens of the subject vaccine formulations will vary based on the particular leukotoxin and GnRH polypeptide moieties selected to construct those molecules. More particularly, in the leukotoxin-GnRH polypeptides used in producing the vaccine formulations under the invention, there will be about 1 to 25% GnRH, preferably about 3 to 20% and most preferably about 7 to 17% GnRH polypeptide per fusion molecule. Increases in the percentage of GnRH present in the LKT-GnRH antigens reduces the amount of total antigen which must be administered to a subject in order to elicit an effective B-cell response to GnRH. Effective dosages can be readily established by one of ordinary skill in the art through routine trials establishing dose response curves. The subject is immunized by administration of the particular leukotoxin-GnRH polypeptide in at least one dose, and preferably two doses. Moreover, the animal may be administered as many doses as is required to maintain a state of immunity.

Below are examples of specific embodiments for carrying out the present invention. The examples are offered for illustrative purposes only, and are not intended to limit the scope of the present invention in any way.

C. Experimental

Materials and Methods

Enzymes were purchased from commercial sources, and used according to the manufacturers' directions. Radionucleotides and nitrocellulose filters were also purchased from commercial sources.

In the cloning of DNA fragments, except where noted, all DNA manipulations were done according to standard procedures. See Sambrook et al., supra. Restriction enzymes, $T_4$ DNA ligase, E. coli, DNA polymerase I, Klenow fragment, and other biological reagents were purchased from commercial suppliers and used according to the manufacturers' directions. Double-stranded DNA fragments were separated on agarose gels.

cDNA and genomic libraries were prepared by standard techniques in pUC13 and the bacteriophage lambda gt11, respectively. See DNA CLONING: Vols I and II, supra.

P. haemolytica biotype A, serotype 1 ("A1") strain B122 was isolated from the lung of a calf which died of pneumonic pasteurellosis and was stored at −70° C. in defibrinated blood. Routine propagation was carried out on blood agar plates or in brain heart infusion broth (Difco Laboratories, Detroit, Mich.) supplemented with 5% (v/v) horse serum (Gibco Canada Ltd., Burlington, Canada). All cultures were incubated at 37° C.

EXAMPLE 1

Isolation of P. haemolytica Leukotoxin Gene

To isolate the leukotoxin gene, gene libraries of P. haemolytica A1 (strain B122) were constructed using standard techniques. See, Lo et al., Infect. Immun., supra; DNA CLONING: Vols. I and II, supra; and Sambrook et al., supra. A genomic library was constructed in the plasmid vector pUC13 and a DNA library constructed in the bacteriophage lambda gt11. The resulting clones were used to transform *E. coli* and individual colonies were pooled and screened for reaction with serum from a calf which had survived a *P. haemolytica* infection and that had been boosted with a concentrated culture supernatant of *P. haemolytica* to increase anti-leukotoxin antibody levels. Positive colonies were screened for their ability to produce leukotoxin by incubating cell lysates with bovine neutrophils and subsequently measuring release of lactate dehydrogenase from the latter.

Several positive colonies were identified and these recombinants were analyzed by restriction endonuclease mapping. One clone appeared to be identical to a leukotoxin gene cloned previously. See, Lo et al., *Infect. Immun.*, supra. To confirm this, smaller fragments were re-cloned and the restriction maps compared. It was determined that approximately 4 kilobase pairs of DNA had been cloned. Progressively larger clones were isolated by carrying out a chromosome walk (5' to 3' direction) in order to isolate full-length recombinants which were approximately 8 kb in length. The final construct was termed pAA114. This construct contained the entire leukotoxin gene sequence.

lktA, a MaeI restriction endonuclease fragment from pAA114 which contained the entire leukotoxin gene, was treated with the Klenow fragment of DNA polymerase I plus nucleotide triphosphates and ligated into the SmaI site of the cloning vector pUC13. This plasmid was named pAA179. From this, two expression constructs were made in the ptac-based vector pGH432:lacI digested with SmaI. One, pAA342, consisted of the 5'-AhaIII fragment of the lktA gene while the other, pAA345, contained the entire MaeI fragment described above. The clone pAA342 expressed a truncated leukotoxin peptide at high levels while pAA345 expressed full length leukotoxin at very low levels. Therefore, the 3' end of the lktA gene (StyI BamHI fragment from pAA345) was ligated to StyI BamHI-digested pAA342, yielding the plasmid pAA352. The structure of pAA352 is shown in FIG. 2 and the nucleotide sequence and predicted amino acid sequence of *P. haemolytica* leukotoxin produced from the pAA352 construct (hereinafter LKT 352) is shown in FIGS. 3A–3I SEQ. ID NOS:5–6

EXAMPLE 2

Construction of LKT-GnRH Fusions

Representative LKT-GnRH fusions were constructed as follows. Oligonucleotides containing sequences corresponding to single copy GnRH and GnRH as four multiple repeats were constructed on a Pharmacia Gene Assembler using standard phosphoramidite chemistry. The sequences of these oligonucleotides are shown in FIGS. 1A SEQ ID NOS: 1–2 and 1B SEQ ID NOS:3–4. The subject oligonucleotides were annealed and ligated into the vector pAA352 (ATCC No. 68283, and described above), which had been digested with the restriction endonuclease BamH1. This vector contains the *P. haemolytica* leukotoxin gene. The ligated DNA was used to transform *E. coli* strain MH3000. Transformants containing the oligonucleotide inserts were identified by restriction endonuclease mapping.

An eight copy GnRH tandem repeat sequence was prepared by annealing the four copy GnRH oligonucleotides and ligating them into a vector which had been digested with the restriction endonuclease BamH1. The oligomers were designed to disable the upstream BamH1 site when inserted and to ensure that the insertion of additional copies of the oligomer would be oriented in the proper reading frame. The sequence of the subject oligonucleotide is shown in FIG. 1B SEQ ID NOS:3–4. Plasmid DNA from the *E. coli* MH3000 strain was then isolated and used to transform the strain JM105. The recombinant plasmids were designated pCB113 (LKT 352:4 copy GnRH, ATCC Accession No. 69749) and pCB112 (LKT 352:8 copy GnRH). Recombinant plasmid pCB113 is shown in FIG. 4, plasmid pCB112 is identical to pCB113 except that the multiple copy GnRH sequence (corresponding to the oligomer of FIG. 1B SEQ ID NOS:3–4) was inserted twice as described above. The nucleotide sequence of the recombinant LKT-GnRH fusion of pCB113 is shown in FIGS. 5A–5H SEQ ID NOS:7–8. The nucleotide sequence of the recombinant LKT-GnRH fusion pCB112 is identical except that the multiple copy GnRH sequence was inserted twice.

EXAMPLE 3

Construction of Shortened LKT Carrier Peptide

A shortened version of the recombinant leukotoxin peptide was constructed from the recombinant gene present on the plasmid pAA352 (as described above). The shortened LKT gene was produced by deleting an internal DNA fragment of approximately 1300 bp in length from the recombinant LKT gene as follows.

The plasmid pCB113, (ATCC Accession No. 69749) which includes the LKT 352 polypeptide fused to four copies of the GnRH polypeptide, was digested with the restriction enzyme BstB1 (New England Biolabs). The resultant linearized plasmid was then digested with mungbean nuclease (Pharmacia) to remove the single stranded protruding termini produced by the BstB1 digestion. The blunted DNA was then digested with the restriction enzyme Nae1 (New England Biolabs), and the digested DNA was loaded onto a 1% agarose gel where the DNA fragments were separated by electrophoresis. A large DNA fragment of approximately 6190 bp was isolated and purified from the agarose gel using a Gene Clean kit (Bio 101), and the purified fragment was allowed to ligate to itself using bacteriophage T4 DNA ligase (Pharmacia). The resulting ligation mix was used to transform competent *E. coli* JM105 cells, and positive clones were identified by their ability to produce an aggregate protein having a molecular weight of approximately 57 KDa. The recombinant plasmid thus formed was designated pCB111, (ATCC Accession No. 69748), and produces a shortened leukotoxin polypeptide (hereinafter referred to as LKT 111) fused to four copies of GnRH polypeptide. The structure of pCB111 is shown in FIG. 6. Plasmid pCB114 is identical to pCB111 except that the multiple copy GnRH sequence (corresponding to the oligomer of FIG. 1B SEQ ID NOS:3–4) was inserted twice. The nucleotide sequence of the recombinant LKT-GnRH fusion of pCB111 is shown in. FIGS. 7A–7E SEQ ID NOS:9–10. The nucleotide sequence of the recombinant LKT-GnRH fusion of pCB114 is identical except that the multiple copy GnRH sequence was inserted twice.

The nucleotide sequence of the ligation fusion point of the subject clones has been confirmed by sequencing with a bacteriophage T7 polymerase sequencing kit (Pharmacia). The nucleotide sequences of these fusion points are shown in FIG. 8A–8B SEQ ID NOS:11–14.

EXAMPLE 4

Purification of LKT-antigen Fusions

The recombinant LKT-GnRH fusions from Examples 2 and 3 were purified using the following procedure. For each fusion, five to ten colonies of the transformed *E. coli* strains were inoculated into 10 ml of TB broth supplemented with 100 micrograms/ml of ampicillin and incubated at 37° C for 6 hours on a G10 shaker, 220 rpm. Four ml of this culture was diluted into each of two baffled Fernbach flasks containing 400 ml of TB broth+ampicillin and incubated overnight as described above. Cells were harvested by centrifugation for 10 minutes at 4,000 rpm in polypropylene bottles, 500 ml volume, using a Sorvall GS3 rotor. The pellet was resuspended in an equal volume of TB broth containing ampicillin which had been prewarmed to 37° C. (i.e., 2×400 ml), and the cells were incubated for 2 hours as described above.

3.2 ml of isopropyl-B,D-thiogalactopyranoside (IPTG, Gibco/BRL), 500 mM in water (final concentration=4 mM), was added to each culture in order to induce synthesis of the recombinant fusion proteins. Cultures were incubated for two hours. Cells were harvested by centrifugation as described above, resuspended in 30 ml of 50 mM Trishydrochloride, 25% (w/v) sucrose, pH 8.0, and frozen at −70° C. The frozen cells were thawed at room temperature after 60 minutes at −70° C., and 5 ml of lysozyme (Sigma, 20 mg/ml in 250 mM Tris-HCl, pH 8.0) was added. The mixture was vortexed at high speed for 10 seconds and then placed on ice for 15 minutes. The cells were then added to 500 ml of lysis buffer in a 1000 ml beaker and mixed by stirring with a 2 ml pipette. The beaker containing the lysed cell suspension was placed on ice and sonicated for a total of 2.5 minutes (5–30 second bursts with 1 minute cooling between each) with a Braun sonicator, large probe, set at 100 watts power. Equal volumes of the solution were placed in Teflon SS34 centrifuge tubes and centrifuged for 20 minutes at 10,000 rpm in a Sorvall SS34 rotor. The pellets were resuspended in a total of 100 ml of sterile double distilled water by vortexing at high speed, and the centrifugation step repeated. Supernatants were discarded and the pellets combined in 20 ml of 10 mM Tris-HCl, 150 mM NaCl, pH 8.0 (Tris-buffered saline) and the suspension frozen overnight at −20° C.

The recombinant suspension was thawed at room temperature and added to 100 ml of 8M Guanidine HCl (Sigma) in Tris-buffered saline and mixed vigorously. A magnetic stir bar was placed in the bottle and the solubilized sample was mixed at room temperature for 30 minutes. The solution was transferred to a 2000 ml Erlenmyer flask and 1200 ml of Tris-buffered saline was added quickly. This mixture was stirred at room temperature for an additional 2 hours. 500 ml aliquots were placed in dialysis bags (Spectrum, 63.7 mm diameter, 6,000–8,000 MW cutoff, #132670, from Fisher scientific) and these were placed in 4,000 ml beakers containing 3,500 ml of Tris-buffered saline +0.5M Guanidine HCl . The beakers were placed in a 4° C. room on a magnetic stirrer overnight after which dialysis buffer was replaced with Tris-buffered saline +0.1M Guanidine HCl and dialysis continued for 12 hours. The buffer was then replaced with Tris-buffered saline +0.05M Guanidine HCl and dialysis continued overnight. The buffer was replaced with Tris-buffered saline (no guanidine), and dialysis continued for 12 hours. This was repeated three more times. The final solution was poured into a 2000 ml plastic roller bottle (Corning) and 13 ml of 100 mM PMSF (in ethanol) was added to inhibit protease activity. The solution was stored at −20° C. in 100 ml aliquots.

To confirm that the fusion proteins had been isolated, aliquots of each preparation were diluted 20-fold in double distilled water, mixed with an equal volume of SDS-PAGE sample buffer, placed in a boiling water bath for five minutes and run through 12% polyacrylamide gels. Recombinant leukotoxin controls were also run.

All fusion proteins were expressed at high levels as inclusion bodies. The predicted molecular weights based on the DNA sequences of the fusion proteins were 104.869 (LKT 352::4 copy GnRH, from pCB113); 110,392 (LKT 352::8 copy GnRH, from pCB112); 57,542 (LKT 111::4 copy GnRH, from pCB111); and 63,241 (LKT 111::8 copy GnRH from pCB114). The predicted molecular weight of the recombinant LKT 352 molecule was 99,338, and the predicted molecular weight of the recombinant LKT 111 molecule was 51,843.

EXAMPLE 5

In Vivo Immunologic Activity of LKT-GnRH Fusions

To test for the ability of LKT-GnRH fusions to induce an anti-GnRH immunological response in vivo, and to compare this response to other GnRH carrier conjugates, the following vaccination trial was performed. Three groups of 8 male pigs, approximately 8 weeks of age (35–50 kg) were used which were Specific Pathogen Free. The animals were maintained in a minimal disease facility and were vaccinated on days 0 and 21 of the trial with the following formulations:

Group 1—placebo which consisted of saline formulated in Emulsigen Plus adjuvant containing 15 mg of dimethyldioctadecylammonium bromide (DDA) (2 ml);

Group 2—LKT 352-GnRH (250 µg LKT, prepared as described in the previous examples) formulated in the same adjuvant (2 ml);

Group 3—VP6-GnRH, 0.5 µg VP6 and 5 µg GnRH, formulated in the same adjuvant (2 ml). The VP6 preparation copy GnRH) gave a dramatic improvement in antibody production over single copy GnRH (as measured by binding to iodinated native GnRH). Further, the above results indicate that a fusion protein comprising a four copy GnRH tandem repeat ligated to LKT 352 represents an optimal immunogenic GnRH antigen form, although immunogenicity may be influenced by dose or subject species.

TABLE 1

| | Group 1 LKT 352::1 Copy GnRH | | | | Group 2 LKT 352::4 Copy GnRH | | | | Group 3 LKT 352::8 Copy GnRH | | | |
|---|---|---|---|---|---|---|---|---|---|---|---|---|
| | Sample No. responding | | mean response (%)* | | No. responding | | mean response (%)* | | No. responding | | mean response (%)* | |
| Day | 1:100 | 1:1000 | 1:100 | 1:1000 | 1:100 | 1:1000 | 1:100 | 1:1000 | 1:100 | 1:1000 | 1:100 | 1:1000 |
| 23 | 0 | 0 | — | — | 3 | 1 | 16 | 9 | 2 | 0 | 33 | — |
| 35 | 2 | 2 | 45 | 20 | 9 | 9 | 75 | 30 | 7 | 5 | 48 | 41 |
| 44 | 2 | 2 | 60 | 39 | 10 | 10 | 55 | 43 | 8 | 7 | 57 | 46 |

*mean response is the average binding of $I^{125}$-GnRH of only those animals with binding in excess of 5%.

was made as described in U.S. Pat. No. 5,071,651, using the binding peptide described therein.

Blood samples were taken on days 0, 21 and 35, allowed to clot, centrifuged at 1500 g, and the serum removed. The serum antibody titres against GnRH were measured using the RIA procedure of Silversides et al., *J. Reprod. Immunol.* (1985) 7:171–184.

The results of this trial indicated that only those animals immunized with the LKT 352-GnRH formulation produced significant titres against GnRH (titres >1:70). Neither the placebo nor the VP6-GnRH groups produced anti-GnRH titres. Previously, multiple vaccinations with doses of GnRH of more than 100 µg, conjugated to other carrier proteins, were required to induce anti-hormone titres. These results indicate that the LKT-GnRH carrier system provides a greatly improved immunogen over prior carrier systems.

EXAMPLE 6

In Vivo Immunologic Effect of Multiple Tandem GnRH Repeats Ligated to LKT

To test for the ability of recombinant LKT-GnRH fusion proteins containing multiple GnRH polypeptide repeats to induce an anti-GnRH immunological response in vivo, the following vaccination trial was performed. Cultures of *E. coli* containing plasmids pCB113 and pCB175 (having 4 and 8 copies of GnRH ligated to LKT 352, respectively) and a plasmid having 1 copy of GnRH ligated to LKT 352 were prepared as described above. Vaccines from each of the above cultures were formulated to contain the equivalent of 5 µg of GnRH in 0.2 ml of Emulsigen Plus. Three groups of 10 female mice were given two subcutaneous injections 23 days apart and blood samples were collected at days 23, 35 and 44 after the primary injection. Serum antibody titres against GnRH were measured at final dilutions of 1:100 and 1:1000 using a standard radioimmunoassay procedure. If less than 5% of the iodinated GnRH was bound, antibody was deemed to be undetectable. The antibody titres thus obtained are summarized in the Table 1.

The results of this study indicate that equal doses of GnRH presented as multiple tandem repeats (four or eight

EXAMPLE 7

In Vivo Immunologic Activity and Biologic Effect of LKT 352::GnRH and LKT 111::GnRH Fusions To test the ability of fusion proteins comprising multiple tandem repeats of GnRH (ligated to either LKT 352 or LKT 111) to elicit an anti-GnRH immunological response in vivo and to manifest a biologic effect in vivo, the following vaccination trial was preformed. Cultures of *E. coli* containing plasmids pCB113 and pCB111 (4 copy GnRH ligated to LKT 352 or LKT 111, respectively) were prepared as described above. Vaccines from each of the above cultures were formulated to contain the equivalent of 5 µg of GnRH in 0.2 ml of VSA-3 adjuvant, (a modified Emulsigen Plus adjuvant), with a control vaccine comprising 0.2 ml of the adjuvant also being prepared. Three groups of 5 male Swiss mice were given two subcutaneous injections 21 days apart, with the initial injections (day 0) given at 5–6 weeks of age. On day 49 the subjects were sacrificed.

Immunological activity of the subject GnRH-LKT fusions was assayed by measuring anti-GnRH antibody titres using a standard radioimmunoassay procedure at a 1:1000 serum dilution. Biological effect of the GnRH-LKT fusions was quantified by standard radioimmunoassay of serum testosterone levels with a sensitivity of 25 pg/ml, and testicular tissue was weighed and histologically examined. The results of this trial are summarized in Table 2.

In the trial, all animal subjects injected with GnRH:LKT antigens had readily detectable antibody levels; however, the LKT 111::GnRH fusion (from plasmid pCB111) showed superior immunogenicity as indicated by uniformity of response and titre. Serum testosterone (produced by the testicular Leydig cells) is secreted in a pulsatile manner, and accordingly, low values and extreme variability of serum levels are expected in normal animal subjects. Under the trial, the control group (receiving the 0.2 ml adjuvant vaccine injections) had normal serum testosterone levels, while both groups of treated subjects had essentially undetectable serum testosterone.

Further under the trial, histological evaluation of testicular tissue revealed varying degrees of Leydig cell atrophy, reduced seminiferous tubule diameter and interruption of spermatogenesis in treated subjects; however, testicular weight remained close to normal in treated animals—even in the presence of high anti-GnRH antibody titres—although there was clear evidence of testicular regression in 2 of 5 subjects receiving the LKT 111::4 copy GnRH fusions.

Accordingly, these results show that multiple copies of GnRH ligated to either LKT 352 or LKT 111 comprise potent immunogens; and further, it is indicated that vaccination with the subject fusion proteins triggers production of antibodies which are able to neutralize endogenous GnRH in vivo, and that a concomitant in vivo biological effect is discernable in animal subjects receiving such vaccinations.

old (at day 0), were injected at day 0 and reinjected at day 21 of the trial. Blood samples were collected at days 0, 21 and 35, with anti-GnRH antibody titres being measured at a final dilution of 1:1000 using a standard radioimmunoassay procedure. The assay results are summarized in Table 3.

Under the trial, anti-GnRH antibodies could not be detected in any subjects prior to immunization, but were readily detected in most subjects by day 35 (one subject in treatment group 4 died due to an infection unrelated to treatment). The results in this trial indicate that fusion proteins comprising multiple GnRH repeats ligated to either

TABLE 2

| Animal | Group 1 Control | | | Group 2 5 μg LKT 352::4 Copy GnRH | | | Group 3 5 μg LKT 111::4 Copy GnRH | | |
|---|---|---|---|---|---|---|---|---|---|
| | Antibody Titre* | Testicular Wt. (mg) | Serum Testosterone† | Antibody Titre* | Testicular Wt. (mg) | Serum Testosterone† | Antibody Titre* | Testicular Wt. (mg) | Serum Testosterone† |
| 1 | 7.0 | 252 | .04 | 73.0 | 282 | .13 | 75.0 | 163 | .00 |
| 2 | 4.0 | 327 | .18 | 14.0 | 334 | .10 | 59.0 | 296 | .07 |
| 3 | 0.0 | 276 | 2.73 | 18.0 | 254 | .03 | 54.0 | 260 | .24 |
| 4 | 0.0 | 220 | .36 | 55.0 | 222 | .05 | 66.0 | 265 | .03 |
| 5 | 1.0 | 232 | 1.44 | 61.0 | 226 | .19 | 64.0 | 50 | .00 |
| Mean | 2.4 | 261 | .95 | 44 | 263 | .10 | 64 | 206 | .07 |
| Std Error | 1.4 | 19 | .51 | 12 | 21 | .03 | 4 | 45 | .04 |

*% Binding of $I^{125}$-GnRH at a 1:1000 serum dilution
†ng/ml

EXAMPLE 8

In Vivo Immunologic Activity of LKT::GnRH Fusions in Porcine Subjects

To test the ability of fusion proteins comprising multiple tandem repeats of GnRH (ligated to either LKT 352 or LKT 111) to elicit anti-GnRH immunological response in vivo in porcine subjects, the following vaccination trial was preformed. Cultures of *E. coli* containing plasmids pCB113, pCB111, pCB175 and pCB114 (LKT 352::4 copy GnRH, LKT 111::4 copy GnRH, LKT 352::8 copy GnRH, and LKT 111::8 copy GnRH, respectively) were prepared as described above. Vaccines from each of the above cultures were formulated to contain the equivalent of 50 μg GnRH and were administered in VSA-3 adjuvant in a 2.0 ml volume. Four groups of 5 male and 5 female weanling pigs, 35 days a LKT 352 or LKT 111 carrier polypeptide form useful immunogens in porcine subjects. Based on the predicted molecular weights of the decapeptide GnRH (1,200), the LKT 111 polypeptide (52,000) and the LKT 352 polypeptide (100,000), the percentages of GnRH in the LKT-GnRH antigen fusions are as follows: 4.9% (LKT 352::4 copy GnRH); 8.5% (LKT 111::4 copy GnRH); 9.3% (LKT 352::8 copy GnRH) and 15.7% (LKT 111::8 copy GnRH). Accordingly, the practical result thus obtained indicates that by using LKT-GnRH fusions comprising the LKT 111 polypeptide carrier, the overall amount of antigen (LKT-GnRH) administered to the subject may be halved (as compared to vaccination compositions using the LKT 352 carrier polypeptide system) to obtain an equivalent anti-GnRH response.

TABLE 3

| Animal Number | Group 1 LKT 352::4 copy GnRH 50 μg day 35 1:1000 dilution | Group 2 LKT 111::4 copy GnRH 50 μg day 35 1:1000 dilution | Group 3 LKT 352::8 copy GnRH 50 μg day 35 1:1000 dilution | Group 4 LKT 111::8 copy GnRH 50 μg day 35 1:1000 dilution |
|---|---|---|---|---|
| 1 | ♂ 47.7 | ♀ 46.0 | ♂ 68.3 | ♂ 51.0 |
| 2 | ♀ 50.3 | ♂ 71.6 | ♂ 65.1 | ♂ 31.7 |
| 3 | ♀ 66.0 | ♀ 21.4 | ♀ 50.7 | ♀ 35.7 |
| 4 | ♀ 70.2 | ♂ 46.2 | ♂ 4.7 | ♀ 65.9 |
| 5 | ♂ 17.3 | ♀ 48.9 | ♀ 38.3 | ♀ |
| 6 | ♂ 18.3 | ♂ 69.4 | ♀ 17.4 | ♂ 11.3 |
| 7 | ♀ 14.7 | ♂ 47.9 | ♀ 51.4 | ♀ 28.3 |
| 8 | ♂ 37.0 | ♀ 44.4 | ♂ 18.0 | ♂ 43.0 |
| 9 | ♂ 26.0 | ♂ 70.8 | ♂ 83.5 | ♀ 78.7 |
| 10 | ♀ 2.7 | ♀ 37.8 | ♀ 24.2 | ♂ 55.9 |
| Mean | 35.0 | 50.4 | 42.2 | 44.6 |

TABLE 3-continued

|  | Group 1<br>LKT 352::4 copy<br>GnRH 50 µg<br>day 35 | Group 2<br>LKT 111::4 copy<br>GnRH 50 µg<br>day 35 | Group 3<br>LKT 352::8 copy<br>GnRH 50 µg<br>day 35 | Group 4<br>LKT 111::8 copy<br>GnRH 50 µg<br>day 35 |
|---|---|---|---|---|
| Animal Number | 1:1000 dilution | 1:1000 dilution | 1:1000 dilution | 1:1000 dilution |
| Standard Deviation | 7.3 | 5.1 | 8.1 | 6.9 |
| Responders | 9/10 | 10/10 | 9/10 | 9/9 |

EXAMPLE 9

Prediction of T-cell Epitopes in the Recombinant

LKT 352 and LKT 111 Molecules

In order to predict potential T-cell epitopes in the leukotoxin polypeptide sequences employed in the LKT-GnRH chimeras of the present invention, the method proposed by Margalit and co-workers (Margalit et al., *J. Immunol* (1987) 138:2213) was performed on the amino acid sequence corresponding to numbers 1 through 199 of the LKT molecule as depicted in Table 4. Under the subject method, the amino acid sequence of the leukotoxin polypeptide sequence was compared to other sequences known to induce a T-cell response and to patterns of types of amino acids which are believed to be required for a T-cell epitope. The results of the comparison are depicted in Table 4.

As can be seen by the predictive results thus obtained, there are several short sequences in the leukotoxin peptide which are identified as potential T-cell epitopes using the criteria suggested by Margalit et al (supra). More particularly, 9 sequences were identified as having a (Charged/Gly-Hydrophobic-Hydrophobic-Polar/Gly) sequence (indicated as pattern "1" in Table 4), and 3 sequences were identified as having a (Charged/Gly-Hydrophobic-Hydrophobic-Hydrophobic/Pro-Polar/Gly) sequence (indicated as pattern "2" in Table 4). By coupling these data with the in vivo anti-GnRH activity produced by both the LKT 352 and the LKT 111 carrier systems in Examples 7 and 8 above, it is indicated that critical T-cell epitopes are retained in the shortened LKT 111 molecule, and that those epitopes are likely contained within the N-terminal portion of the LKT 352 and LKT 111 molecules.

TABLE 4

| LKT Sequence Patterns Corresponding<br>To Potential T-cell Epitopes | |
|---|---|
| LKT Amino Acid Sequences Showing Pattern "1": | |
| GTID | (aa's 27–30 SEQ ID NO: 16) |
| GITG | (aa's 66–69 SEQ ID NO: 17) |
| GVIS | (aa's 69–72 SEQ ID NO: 18) |
| HVAN | (aa's 85–88 SEQ ID NO: 19) |
| KIVE | (aa's 93–96 SEQ ID NO: 20) |
| DLAG | (aa's 152–155 SEQ ID NO: 21) |
| KVLS | (aa's 162–165 SEQ ID NO: 22) |
| DAFE | (aa's 171–174 SEQ ID NO: 23) |
| KLVQ | (aa's 183–186 SEQ ID NO: 24) |
| GIID | (aa's 192–195 SEQ ID NO: 25) |
| LKT Amino Acid Sequence Showing Pattern "2": | |
| RYLAN | (aa's 114–118 SEQ ID NO: 26) |
| KFLLN | (aa's 124–128 SEQ ID NO: 27) |
| KAYVD | (aa's 167–171 SEQ ID NO: 28) |

D. Industrial Applicability

The leukotoxin-GnRH chimeras of the present invention are of use in providing immunogens that, when administered to a vertebrate host, serve to immunize the host against endogenous GnRH, which in turn acts to inhibit the reproductive function or capability of the host.

Notwithstanding the specific uses exemplified in this specification, the novel chimeric molecules disclosed herein suggest a means for providing fusion proteins comprising more than one GnRH peptide sequence, occurring in either multiple or tandem repeats, which are fused to immunogenic epitopes supplied by the leukotoxin polypeptide portion of the molecule (and in some cases by spacer peptide sequences occurring between selected GnRH sequences). The subject chimeric proteins constructed under the present invention provide enhanced immunogenicity to the fused GnRH peptide sequences, allowing an immunized vertebrate host to mount an effective immune response toward endogenous GnRH; effecting an interruption in the synthesis and release of the two gonadotropic hormones, luteinizing hormone (LH) and follicle stimulating hormone (FSH) and rendering the host temporarily sterile. In this manner, the novel leukotoxin-GnRH constructs may be employed in immunosterilization vaccines to provide an alternative to invasive sterilization procedures currently practiced in domestic and farm animal husbandry.

Other contemplated uses of the instant fusion molecules include population control, for example the interruption of reproduction capabilities in wild rodent populations. In this regard, the LKT-GnRH fusion molecules may be used as an alternative to population control measures currently practiced, such as poisoning and the like. The fusion products of the instant invention may also be administered in constructs having both slow and fast release components. In this manner, the need for multiple vaccinations may be avoided. Further, since the amino acid sequence of GnRH is highly conserved among species, a single leukotoxin-GnRH fusion vaccine product may be produced which will exhibit broad cross species effectiveness.

Thus, various chimeric proteins comprising leukotoxin fused to selected GnRH polypeptides have been disclosed. Although preferred embodiments of the subject invention have been described in some detail, it is understood that obvious variations can be made without departing from the spirit and the scope of the invention as defined by the appended claims.

Deposits of Strains Useful in Practicing the Invention

A deposit of biologically pure cultures of the following strains was made with the American Type Culture Collection (ATCC), 12301 Parklawn Drive, Rockville, Md. The accession number indicated was assigned after successful viability testing, and the requisite fees were paid. The deposits were made under the provisions of the Budapest Treaty on the International Recognition of the Deposit of Microorganisms for the Purpose of Patent Procedure and the Regulations thereunder (Budapest Treaty). This assures maintenance of viable cultures for a period of thirty (30) years from the date of deposit and at least five (5) years after the most recent request for the furnishing of a sample of the deposit by the depository. The organisms will be made available by the ATCC under the terms of the Budapest Treaty, which assures permanent and unrestricted availability of the cultures to one determined by the U.S. Commissioner of Patents and Trademarks to be entitled thereto according to 35 USC §122 and the Commissioner's rules pursuant thereto (including 37 CFR §1.12).

These deposits are provided merely as convenience to those of skill in the art, and are not an admission that a deposit is required under 35 USC §112. The nucleic acid sequences of these plasmids, as well as the amino acid sequences of the polypeptides encoded thereby, are incorporated herein by reference and are controlling in the event of any conflict with the description herein. A license may be required to make, use, or sell the deposited materials, and no such license is hereby granted.

| Strain | Deposit Date | ATCC No. |
| --- | --- | --- |
| *P. haemolytica* serotype 1 B122 | February 1, 1989 | 53863 |
| pAA352 in *E. coli* W1485 | March 30, 1990 | 68283 |
| pCB113 in *E. coli* JM105 | February 1, 1995 | 69749 |
| pCB111 in *E. coli* JM105 | February 1, 1995 | 69748 |

We claim:

1. A chimeric protein comprising a leukotoxin polypeptide fused to a multimer having more than one selected GnRH polypeptide, whereby said leukotoxin portion of said chimeric protein acts to increase the immunogenicity of said GnRH multimer.

2. The chimeric protein of claim 1 wherein said leukotoxin polypeptide lacks leukotoxic activity.

3. The chimeric protein of claim 2 wherein said leukotoxin is LKT 352.

4. The chimeric protein of claim 2 wherein said leukotoxin is LKT 111.

5. The chimeric protein of claim 1 wherein said GnRH multimer comprises a molecule according to the general formula GnRH-X-GnRH wherein X is selected from the group consisting of a peptide linkage, an amino acid spacer group, a leukotoxin polypeptide and $[GnRH]_n$ where n is greater than or equal to 1, and further wherein GnRH comprises any GnRH polypeptide.

6. The chimeric protein of claim 5 wherein X comprises an amino acid spacer group including at least one helper T-cell epitope.

7. The chimeric protein of claim 1 wherein said chimeric protein comprises the amino acid sequence depicted in FIGS. 5A–5h, SEQ ID NOS:7–8.

8. The chimeric protein of claim 1 wherein said chimeric protein comprises the amino acid sequence depicted in FIGS. 7A–7E, SEQ ID NOS:9–10.

9. A vaccine composition comprising the chimeric protein of claim 1 and a pharmaceutically acceptable vehicle.

10. A vaccine composition comprising the chimeric protein of claim 2 and a pharmaceutically acceptable vehicle.

11. A vaccine composition comprising the chimeric protein of claim 5 and a pharmaceutically acceptable vehicle.

12. A vaccine composition comprising the chimeric protein of claim 7 and a pharmaceutically acceptable vehicle.

13. A vaccine composition comprising the chimeric protein of claim 8 and a pharmaceutically acceptable vehicle.

14. A method for presenting a selected GnRH multimer to a subject comprising administering to said subject an effective amount of a vaccine composition according to claim 9.

15. A method for presenting a selected GnRH multimer to a subject comprising administering to said subject an effective amount of a vaccine composition according to claim 10.

16. A method for presenting a selected GnRH multimer to a subject comprising administering to said subject an effective amount of a vaccine composition according to claim 11.

17. A method for presenting a selected GnRH multimer to a subject comprising administering to said subject an effective amount of a vaccine composition according to claim 12.

18. A method for presenting a selected GnRH multimer to a subject comprising administering to said subject an effective amount of a vaccine composition according to claim 13.

19. A chimeric protein comprising a leukotoxin polypeptide fused to a multimer having eight selected GnRH polypeptides, wherein the C-terminus of the leukotoxin polypeptide is fused to the N-terminus of the multimer.

20. The chimeric protein of claim 19, wherein the leukotoxin polypeptide comprises the 52 kD LKT 111 carrier polypeptide.

21. A chimeric protein comprising a leukotoxin polypeptide fused to a multimer having eight selected GnRH polypeptides, wherein the C-terminus of the multimer is fused to the N-terminus of the leukotoxin polypeptide.

22. The chimeric protein of claim 21, wherein the leukotoxin polypeptide comprises the 52 kD LKT 111 carrier polypeptide.

23. A vaccine composition comprising the chimeric protein of claim 19 and a pharmaceutically acceptable vehicle.

24. A vaccine composition comprising the chimeric protein of claim 20 and a pharmaceutically acceptable vehicle.

25. A vaccine composition comprising the chimeric protein of claim 21 and a pharmaceutically acceptable vehicle.

26. A vaccine composition comprising the chimeric protein of claim 22 and a pharmaceutically acceptable vehicle.

\* \* \* \* \*

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..30

( x i ) SEQUENCE DESCRIPTION: SEQ ID NO:1:

```
CAG  CAT  TGG  AGC  TAC  GGC  CTG  CGC  CCT  GGC                          30
Gln  His  Trp  Ser  Tyr  Gly  Leu  Arg  Pro  Gly
 1             5                           10
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Gln  His  Trp  Ser  Tyr  Gly  Leu  Arg  Pro  Gly
 1             5                           10
```

( 2 ) INFORMATION FOR SEQ ID NO:3:

( i ) SEQUENCE CHARACTERISTICS:
        ( A ) LENGTH: 147 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..147

( x i ) SEQUENCE DESCRIPTION: SEQ ID NO:3:

```
CAG  CAT  TGG  AGC  TAC  GGC  CTG  CGC  CCT  GGC  AGC  GGT  TCT  CAA  GAT  TGG        48
Gln  His  Trp  Ser  Tyr  Gly  Leu  Arg  Pro  Gly  Ser  Gly  Ser  Gln  Asp  Trp
 1                    5                        10                        15

AGC  TAC  GGC  CTG  CGT  CCG  GGT  GGC  TCT  AGC  CAG  CAT  TGG  AGC  TAC  GGC        96
Ser  Tyr  Gly  Leu  Arg  Pro  Gly  Gly  Ser  Ser  Gln  His  Trp  Ser  Tyr  Gly
                20                        25                        30

CTG  CGC  CCT  GGC  AGC  GGT  AGC  CAA  GAT  TGG  AGC  TAC  GGC  CTG  CGT  CCG       144
Leu  Arg  Pro  Gly  Ser  Gly  Ser  Gln  Asp  Trp  Ser  Tyr  Gly  Leu  Arg  Pro
           35                        40                        45

GGT                                                                                   147
Gly
```

( 2 ) INFORMATION FOR SEQ ID NO:4:

( i ) SEQUENCE CHARACTERISTICS:
        ( A ) LENGTH: 49 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Gln  His  Trp  Ser  Tyr  Gly  Leu  Arg  Pro  Gly  Ser  Gly  Ser  Gln  Asp  Trp
 1                    5                        10                        15

Ser  Tyr  Gly  Leu  Arg  Pro  Gly  Gly  Ser  Ser  Gln  His  Trp  Ser  Tyr  Gly
                20                        25                        30

Leu  Arg  Pro  Gly  Ser  Gly  Ser  Gln  Asp  Trp  Ser  Tyr  Gly  Leu  Arg  Pro
           35                        40                        45

Gly
```

( 2 ) INFORMATION FOR SEQ ID NO:5:

( i ) SEQUENCE CHARACTERISTICS:
        ( A ) LENGTH: 2794 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..2778

( x i ) SEQUENCE DESCRIPTION: SEQ ID NO:5:

```
ATG  GCT  ACT  GTT  ATA  GAT  CTA  AGC  TTC  CCA  AAA  ACT  GGG  GCA  AAA  AAA        48
Met  Ala  Thr  Val  Ile  Asp  Leu  Ser  Phe  Pro  Lys  Thr  Gly  Ala  Lys  Lys
 1                    5                        10                        15

ATT  ATC  CTC  TAT  ATT  CCC  CAA  AAT  TAC  CAA  TAT  GAT  ACT  GAA  CAA  GGT        96
Ile  Ile  Leu  Tyr  Ile  Pro  Gln  Asn  Tyr  Gln  Tyr  Asp  Thr  Glu  Gln  Gly
                20                        25                        30

AAT  GGT  TTA  CAG  GAT  TTA  GTC  AAA  GCG  GCC  GAA  GAG  TTG  GGG  ATT  GAG       144
Asn  Gly  Leu  Gln  Asp  Leu  Val  Lys  Ala  Ala  Glu  Glu  Leu  Gly  Ile  Glu
           35                        40                        45

GTA  CAA  AGA  GAA  GAA  CGC  AAT  AAT  ATT  GCA  ACA  GCT  CAA  ACC  AGT  TTA       192
Val  Gln  Arg  Glu  Glu  Arg  Asn  Asn  Ile  Ala  Thr  Ala  Gln  Thr  Ser  Leu
      50                        55                        60

GGC  ACG  ATT  CAA  ACC  GCT  ATT  GGC  TTA  ACT  GAG  CGT  GGC  ATT  GTG  TTA       240
Gly  Thr  Ile  Gln  Thr  Ala  Ile  Gly  Leu  Thr  Glu  Arg  Gly  Ile  Val  Leu
 65                        70                        75                        80

TCC  GCT  CCA  CAA  ATT  GAT  AAA  TTG  CTA  CAG  AAA  ACT  AAA  GCA  GGC  CAA       288
Ser  Ala  Pro  Gln  Ile  Asp  Lys  Leu  Leu  Gln  Lys  Thr  Lys  Ala  Gly  Gln
                85                        90                        95
```

| | | | | | | | | | | | | | | | | |
|---|---|---|---|---|---|---|---|---|---|---|---|---|---|---|---|---|
| GCA | TTA | GGT | TCT | GCC | GAA | AGC | ATT | GTA | CAA | AAT | GCA | AAT | AAA | GCC | AAA | 336 |
| Ala | Leu | Gly | Ser | Ala | Glu | Ser | Ile | Val | Gln | Asn | Ala | Asn | Lys | Ala | Lys | |
| | | | 100 | | | | 105 | | | | | | 110 | | | |
| ACT | GTA | TTA | TCT | GGC | ATT | CAA | TCT | ATT | TTA | GGC | TCA | GTA | TTG | GCT | GGA | 384 |
| Thr | Val | Leu | Ser | Gly | Ile | Gln | Ser | Ile | Leu | Gly | Ser | Val | Leu | Ala | Gly | |
| | | 115 | | | | | 120 | | | | | 125 | | | | |
| ATG | GAT | TTA | GAT | GAG | GCC | TTA | CAG | AAT | AAC | AGC | AAC | CAA | CAT | GCT | CTT | 432 |
| Met | Asp | Leu | Asp | Glu | Ala | Leu | Gln | Asn | Asn | Ser | Asn | Gln | His | Ala | Leu | |
| | 130 | | | | | 135 | | | | | 140 | | | | | |
| GCT | AAA | GCT | GGC | TTG | GAG | CTA | ACA | AAT | TCA | TTA | ATT | GAA | AAT | ATT | GCT | 480 |
| Ala | Lys | Ala | Gly | Leu | Glu | Leu | Thr | Asn | Ser | Leu | Ile | Glu | Asn | Ile | Ala | |
| 145 | | | | | 150 | | | | | 155 | | | | | 160 | |
| AAT | TCA | GTA | AAA | ACA | CTT | GAC | GAA | TTT | GGT | GAG | CAA | ATT | AGT | CAA | TTT | 528 |
| Asn | Ser | Val | Lys | Thr | Leu | Asp | Glu | Phe | Gly | Glu | Gln | Ile | Ser | Gln | Phe | |
| | | | | 165 | | | | | 170 | | | | | 175 | | |
| GGT | TCA | AAA | CTA | CAA | AAT | ATC | AAA | GGC | TTA | GGG | ACT | TTA | GGA | GAC | AAA | 576 |
| Gly | Ser | Lys | Leu | Gln | Asn | Ile | Lys | Gly | Leu | Gly | Thr | Leu | Gly | Asp | Lys | |
| | | | 180 | | | | | 185 | | | | | 190 | | | |
| CTC | AAA | AAT | ATC | GGT | GGA | CTT | GAT | AAA | GCT | GGC | CTT | GGT | TTA | GAT | GTT | 624 |
| Leu | Lys | Asn | Ile | Gly | Gly | Leu | Asp | Lys | Ala | Gly | Leu | Gly | Leu | Asp | Val | |
| | | 195 | | | | | 200 | | | | | 205 | | | | |
| ATC | TCA | GGG | CTA | TTA | TCG | GGC | GCA | ACA | GCT | GCA | CTT | GTA | CTT | GCA | GAT | 672 |
| Ile | Ser | Gly | Leu | Leu | Ser | Gly | Ala | Thr | Ala | Ala | Leu | Val | Leu | Ala | Asp | |
| | 210 | | | | | 215 | | | | | 220 | | | | | |
| AAA | AAT | GCT | TCA | ACA | GCT | AAA | AAA | GTG | GGT | GCG | GGT | TTT | GAA | TTG | GCA | 720 |
| Lys | Asn | Ala | Ser | Thr | Ala | Lys | Lys | Val | Gly | Ala | Gly | Phe | Glu | Leu | Ala | |
| 225 | | | | | 230 | | | | | 235 | | | | | 240 | |
| AAC | CAA | GTT | GTT | GGT | AAT | ATT | ACC | AAA | GCC | GTT | TCT | TCT | TAC | ATT | TTA | 768 |
| Asn | Gln | Val | Val | Gly | Asn | Ile | Thr | Lys | Ala | Val | Ser | Ser | Tyr | Ile | Leu | |
| | | | | 245 | | | | | 250 | | | | | 255 | | |
| GCC | CAA | CGT | GTT | GCA | GCA | GGT | TTA | TCT | TCA | ACT | GGG | CCT | GTG | GCT | GCT | 816 |
| Ala | Gln | Arg | Val | Ala | Ala | Gly | Leu | Ser | Ser | Thr | Gly | Pro | Val | Ala | Ala | |
| | | 260 | | | | | 265 | | | | | 270 | | | | |
| TTA | ATT | GCT | TCT | ACT | GTT | TCT | CTT | GCG | ATT | AGC | CCA | TTA | GCA | TTT | GCC | 864 |
| Leu | Ile | Ala | Ser | Thr | Val | Ser | Leu | Ala | Ile | Ser | Pro | Leu | Ala | Phe | Ala | |
| | | 275 | | | | | 280 | | | | | 285 | | | | |
| GGT | ATT | GCC | GAT | AAA | TTT | AAT | CAT | GCA | AAA | AGT | TTA | GAG | AGT | TAT | GCC | 912 |
| Gly | Ile | Ala | Asp | Lys | Phe | Asn | His | Ala | Lys | Ser | Leu | Glu | Ser | Tyr | Ala | |
| | 290 | | | | | 295 | | | | | 300 | | | | | |
| GAA | CGC | TTT | AAA | AAA | TTA | GGC | TAT | GAC | GGA | GAT | AAT | TTA | TTA | GCA | GAA | 960 |
| Glu | Arg | Phe | Lys | Lys | Leu | Gly | Tyr | Asp | Gly | Asp | Asn | Leu | Leu | Ala | Glu | |
| 305 | | | | | 310 | | | | | 315 | | | | | 320 | |
| TAT | CAG | CGG | GGA | ACA | GGG | ACT | ATT | GAT | GCA | TCG | GTT | ACT | GCA | ATT | AAT | 1008 |
| Tyr | Gln | Arg | Gly | Thr | Gly | Thr | Ile | Asp | Ala | Ser | Val | Thr | Ala | Ile | Asn | |
| | | | 325 | | | | | 330 | | | | | 335 | | | |
| ACC | GCA | TTG | GCC | GCT | ATT | GCT | GGT | GGT | GTG | TCT | GCT | GCT | GCA | GCC | GGC | 1056 |
| Thr | Ala | Leu | Ala | Ala | Ile | Ala | Gly | Gly | Val | Ser | Ala | Ala | Ala | Ala | Gly | |
| | | | 340 | | | | | 345 | | | | | 350 | | | |
| TCG | GTT | ATT | GCT | TCA | CCG | ATT | GCC | TTA | TTA | GTA | TCT | GGG | ATT | ACC | GGT | 1104 |
| Ser | Val | Ile | Ala | Ser | Pro | Ile | Ala | Leu | Leu | Val | Ser | Gly | Ile | Thr | Gly | |
| | | 355 | | | | | 360 | | | | | 365 | | | | |
| GTA | ATT | TCT | ACG | ATT | CTG | CAA | TAT | TCT | AAA | CAA | GCA | ATG | TTT | GAG | CAC | 1152 |
| Val | Ile | Ser | Thr | Ile | Leu | Gln | Tyr | Ser | Lys | Gln | Ala | Met | Phe | Glu | His | |
| | | 370 | | | | | 375 | | | | | 380 | | | | |
| GTT | GCA | AAT | AAA | ATT | CAT | AAC | AAA | ATT | GTA | GAA | TGG | GAA | AAA | AAT | AAT | 1200 |
| Val | Ala | Asn | Lys | Ile | His | Asn | Lys | Ile | Val | Glu | Trp | Glu | Lys | Asn | Asn | |
| 385 | | | | | 390 | | | | | 395 | | | | | 400 | |
| CAC | GGT | AAG | AAC | TAC | TTT | GAA | AAT | GGT | TAC | GAT | GCC | CGT | TAT | CTT | GCG | 1248 |
| His | Gly | Lys | Asn | Tyr | Phe | Glu | Asn | Gly | Tyr | Asp | Ala | Arg | Tyr | Leu | Ala | |
| | | | | 405 | | | | | 410 | | | | | 415 | | |

| | | | | | | | | | | | | | | | | |
|---|---|---|---|---|---|---|---|---|---|---|---|---|---|---|---|---|
| AAT | TTA | CAA | GAT | AAT | ATG | AAA | TTC | TTA | CTG | AAC | TTA | AAC | AAA | GAG | TTA | 1296 |
| Asn | Leu | Gln | Asp | Asn | Met | Lys | Phe | Leu | Leu | Asn | Leu | Asn | Lys | Glu | Leu | |
| | | | 420 | | | | 425 | | | | | | 430 | | | |
| CAG | GCA | GAA | CGT | GTC | ATC | GCT | ATT | ACT | CAG | CAG | CAA | TGG | GAT | AAC | AAC | 1344 |
| Gln | Ala | Glu | Arg | Val | Ile | Ala | Ile | Thr | Gln | Gln | Gln | Trp | Asp | Asn | Asn | |
| | | 435 | | | | | 440 | | | | | 445 | | | | |
| ATT | GGT | GAT | TTA | GCT | GGT | ATT | AGC | CGT | TTA | GGT | GAA | AAA | GTC | CTT | AGT | 1392 |
| Ile | Gly | Asp | Leu | Ala | Gly | Ile | Ser | Arg | Leu | Gly | Glu | Lys | Val | Leu | Ser | |
| | | 450 | | | | | 455 | | | | | 460 | | | | |
| GGT | AAA | GCC | TAT | GTG | GAT | GCG | TTT | GAA | GAA | GGC | AAA | CAC | ATT | AAA | GCC | 1440 |
| Gly | Lys | Ala | Tyr | Val | Asp | Ala | Phe | Glu | Glu | Gly | Lys | His | Ile | Lys | Ala | |
| 465 | | | | | 470 | | | | | 475 | | | | | 480 | |
| GAT | AAA | TTA | GTA | CAG | TTG | GAT | TCG | GCA | AAC | GGT | ATT | ATT | GAT | GTG | AGT | 1488 |
| Asp | Lys | Leu | Val | Gln | Leu | Asp | Ser | Ala | Asn | Gly | Ile | Ile | Asp | Val | Ser | |
| | | | | 485 | | | | | 490 | | | | | 495 | | |
| AAT | TCG | GGT | AAA | GCG | AAA | ACT | CAG | CAT | ATC | TTA | TTC | AGA | ACG | CCA | TTA | 1536 |
| Asn | Ser | Gly | Lys | Ala | Lys | Thr | Gln | His | Ile | Leu | Phe | Arg | Thr | Pro | Leu | |
| | | 500 | | | | | 505 | | | | | 510 | | | | |
| TTG | ACG | CCG | GGA | ACA | GAG | CAT | CGT | GAA | CGC | GTA | CAA | ACA | GGT | AAA | TAT | 1584 |
| Leu | Thr | Pro | Gly | Thr | Glu | His | Arg | Glu | Arg | Val | Gln | Thr | Gly | Lys | Tyr | |
| | | 515 | | | | | 520 | | | | | 525 | | | | |
| GAA | TAT | ATT | ACC | AAG | CTC | AAT | ATT | AAC | CGT | GTA | GAT | AGC | TGG | AAA | ATT | 1632 |
| Glu | Tyr | Ile | Thr | Lys | Leu | Asn | Ile | Asn | Arg | Val | Asp | Ser | Trp | Lys | Ile | |
| | 530 | | | | | 535 | | | | | 540 | | | | | |
| ACA | GAT | GGT | GCA | GCA | AGT | TCT | ACC | TTT | GAT | TTA | ACT | AAC | GTT | GTT | CAG | 1680 |
| Thr | Asp | Gly | Ala | Ala | Ser | Ser | Thr | Phe | Asp | Leu | Thr | Asn | Val | Val | Gln | |
| 545 | | | | | 550 | | | | | 555 | | | | | 560 | |
| CGT | ATT | GGT | ATT | GAA | TTA | GAC | AAT | GCT | GGA | AAT | GTA | ACT | AAA | ACC | AAA | 1728 |
| Arg | Ile | Gly | Ile | Glu | Leu | Asp | Asn | Ala | Gly | Asn | Val | Thr | Lys | Thr | Lys | |
| | | | | 565 | | | | | 570 | | | | | 575 | | |
| GAA | ACA | AAA | ATT | ATT | GCC | AAA | CTT | GGT | GAA | GGT | GAT | GAC | AAC | GTA | TTT | 1776 |
| Glu | Thr | Lys | Ile | Ile | Ala | Lys | Leu | Gly | Glu | Gly | Asp | Asp | Asn | Val | Phe | |
| | | | 580 | | | | | 585 | | | | | 590 | | | |
| GTT | GGT | TCT | GGT | ACG | ACG | GAA | ATT | GAT | GGC | GGT | GAA | GGT | TAC | GAC | CGA | 1824 |
| Val | Gly | Ser | Gly | Thr | Thr | Glu | Ile | Asp | Gly | Gly | Glu | Gly | Tyr | Asp | Arg | |
| | | 595 | | | | | 600 | | | | | 605 | | | | |
| GTT | CAC | TAT | AGC | CGT | GGA | AAC | TAT | GGT | GCT | TTA | ACT | ATT | GAT | GCA | ACC | 1872 |
| Val | His | Tyr | Ser | Arg | Gly | Asn | Tyr | Gly | Ala | Leu | Thr | Ile | Asp | Ala | Thr | |
| | | 610 | | | | | 615 | | | | | 620 | | | | |
| AAA | GAG | ACC | GAG | CAA | GGT | AGT | TAT | ACC | GTA | AAT | CGT | TTC | GTA | GAA | ACC | 1920 |
| Lys | Glu | Thr | Glu | Gln | Gly | Ser | Tyr | Thr | Val | Asn | Arg | Phe | Val | Glu | Thr | |
| 625 | | | | | 630 | | | | | 635 | | | | | 640 | |
| GGT | AAA | GCA | CTA | CAC | GAA | GTG | ACT | TCA | ACC | CAT | ACC | GCA | TTA | GTG | GGC | 1968 |
| Gly | Lys | Ala | Leu | His | Glu | Val | Thr | Ser | Thr | His | Thr | Ala | Leu | Val | Gly | |
| | | | | 645 | | | | | 650 | | | | | 655 | | |
| AAC | CGT | GAA | GAA | AAA | ATA | GAA | TAT | CGT | CAT | AGC | AAT | AAC | CAG | CAC | CAT | 2016 |
| Asn | Arg | Glu | Glu | Lys | Ile | Glu | Tyr | Arg | His | Ser | Asn | Asn | Gln | His | His | |
| | | | 660 | | | | | 665 | | | | | 670 | | | |
| GCC | GGT | TAT | TAC | ACC | AAA | GAT | ACC | TTG | AAA | GCT | GTT | GAA | GAA | ATT | ATC | 2064 |
| Ala | Gly | Tyr | Tyr | Thr | Lys | Asp | Thr | Leu | Lys | Ala | Val | Glu | Glu | Ile | Ile | |
| | | 675 | | | | | 680 | | | | | 685 | | | | |
| GGT | ACA | TCA | CAT | AAC | GAT | ATC | TTT | AAA | GGT | AGT | AAG | TTC | AAT | GAT | GCC | 2112 |
| Gly | Thr | Ser | His | Asn | Asp | Ile | Phe | Lys | Gly | Ser | Lys | Phe | Asn | Asp | Ala | |
| | 690 | | | | | 695 | | | | | 700 | | | | | |
| TTT | AAC | GGT | GGT | GAT | GGT | GTC | GAT | ACT | ATT | GAC | GGT | AAC | GAC | GGC | AAT | 2160 |
| Phe | Asn | Gly | Gly | Asp | Gly | Val | Asp | Thr | Ile | Asp | Gly | Asn | Asp | Gly | Asn | |
| 705 | | | | | 710 | | | | | 715 | | | | | 720 | |
| GAC | CGC | TTA | TTT | GGT | GGT | AAA | GGC | GAT | GAT | ATT | CTC | GAT | GGT | GGA | AAT | 2208 |
| Asp | Arg | Leu | Phe | Gly | Gly | Lys | Gly | Asp | Asp | Ile | Leu | Asp | Gly | Gly | Asn | |
| | | | | 725 | | | | | 730 | | | | | 735 | | |

| | | | | | | | | | | | | | | | | |
|---|---|---|---|---|---|---|---|---|---|---|---|---|---|---|---|---|
| GGT | GAT | GAT | TTT | ATC | GAT | GGC | GGT | AAA | GGC | AAC | GAC | CTA | TTA | CAC | GGT | 2256 |
| Gly | Asp | Asp | Phe<br>740 | Ile | Asp | Gly | Gly | Lys<br>745 | Gly | Asn | Asp | Leu | Leu<br>750 | His | Gly | |
| GGC | AAG | GGC | GAT | GAT | ATT | TTC | GTT | CAC | CGT | AAA | GGC | GAT | GGT | AAT | GAT | 2304 |
| Gly | Lys | Gly<br>755 | Asp | Asp | Ile | Phe | Val<br>760 | His | Arg | Lys | Gly | Asp<br>765 | Gly | Asn | Asp | |
| ATT | ATT | ACC | GAT | TCT | GAC | GGC | AAT | GAT | AAA | TTA | TCA | TTC | TCT | GAT | TCG | 2352 |
| Ile | Ile<br>770 | Thr | Asp | Ser | Asp | Gly | Asn<br>775 | Asp | Lys | Leu | Ser | Phe<br>780 | Ser | Asp | Ser | |
| AAC | TTA | AAA | GAT | TTA | ACA | TTT | GAA | AAA | GTT | AAA | CAT | AAT | CTT | GTC | ATC | 2400 |
| Asn<br>785 | Leu | Lys | Asp | Leu | Thr<br>790 | Phe | Glu | Lys | Val | Lys<br>795 | His | Asn | Leu | Val | Ile<br>800 | |
| ACG | AAT | AGC | AAA | AAA | GAG | AAA | GTG | ACC | ATT | CAA | AAC | TGG | TTC | CGA | GAG | 2448 |
| Thr | Asn | Ser | Lys | Lys<br>805 | Glu | Lys | Val | Thr | Ile<br>810 | Gln | Asn | Trp | Phe | Arg<br>815 | Glu | |
| GCT | GAT | TTT | GCT | AAA | GAA | GTG | CCT | AAT | TAT | AAA | GCA | ACT | AAA | GAT | GAG | 2496 |
| Ala | Asp | Phe | Ala<br>820 | Lys | Glu | Val | Pro | Asn<br>825 | Tyr | Lys | Ala | Thr | Lys<br>830 | Asp | Glu | |
| AAA | ATC | GAA | GAA | ATC | ATC | GGT | CAA | AAT | GGC | GAG | CGG | ATC | ACC | TCA | AAG | 2544 |
| Lys | Ile | Glu<br>835 | Glu | Ile | Ile | Gly | Gln<br>840 | Asn | Gly | Glu | Arg | Ile<br>845 | Thr | Ser | Lys | |
| CAA | GTT | GAT | GAT | CTT | ATC | GCA | AAA | GGT | AAC | GGC | AAA | ATT | ACC | CAA | GAT | 2592 |
| Gln | Val<br>850 | Asp | Asp | Leu | Ile | Ala<br>855 | Lys | Gly | Asn | Gly | Lys<br>860 | Ile | Thr | Gln | Asp | |
| GAG | CTA | TCA | AAA | GTT | GTT | GAT | AAC | TAT | GAA | TTG | CTC | AAA | CAT | AGC | AAA | 2640 |
| Glu<br>865 | Leu | Ser | Lys | Val | Val<br>870 | Asp | Asn | Tyr | Glu | Leu<br>875 | Leu | Lys | His | Ser | Lys<br>880 | |
| AAT | GTG | ACA | AAC | AGC | TTA | GAT | AAG | TTA | ATC | TCA | TCT | GTA | AGT | GCA | TTT | 2688 |
| Asn | Val | Thr | Asn | Ser<br>885 | Leu | Asp | Lys | Leu | Ile<br>890 | Ser | Ser | Val | Ser | Ala<br>895 | Phe | |
| ACC | TCG | TCT | AAT | GAT | TCG | AGA | AAT | GTA | TTA | GTG | GCT | CCA | ACT | TCA | ATG | 2736 |
| Thr | Ser | Ser | Asn<br>900 | Asp | Ser | Arg | Asn | Val<br>905 | Leu | Val | Ala | Pro | Thr<br>910 | Ser | Met | |
| TTG | GAT | CAA | AGT | TTA | TCT | TCT | CTT | CAA | TTT | GCT | AGG | GGA | TCC | | | 2778 |
| Leu | Asp | Gln<br>915 | Ser | Leu | Ser | Ser | Leu<br>920 | Gln | Phe | Ala | Arg | Gly<br>925 | Ser | | | |

TAGCTAGCTA GCCATG 2794

( 2 ) INFORMATION FOR SEQ ID NO:6:

( i ) SEQUENCE CHARACTERISTICS:
        ( A ) LENGTH: 926 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Met<br>1 | Ala | Thr | Val | Ile<br>5 | Asp | Leu | Ser | Phe | Pro<br>10 | Lys | Thr | Gly | Ala | Lys<br>15 | Lys |
| Ile | Ile | Leu | Tyr<br>20 | Ile | Pro | Gln | Asn | Tyr<br>25 | Gln | Tyr | Asp | Thr | Glu<br>30 | Gln | Gly |
| Asn | Gly | Leu<br>35 | Gln | Asp | Leu | Val | Lys<br>40 | Ala | Ala | Glu | Glu | Leu<br>45 | Gly | Ile | Glu |
| Val | Gln<br>50 | Arg | Glu | Glu | Arg | Asn<br>55 | Asn | Ile | Ala | Thr | Ala<br>60 | Gln | Thr | Ser | Leu |
| Gly<br>65 | Thr | Ile | Gln | Thr | Ala<br>70 | Ile | Gly | Leu | Thr | Glu<br>75 | Arg | Gly | Ile | Val | Leu<br>80 |
| | Ser | Ala | Pro | Gln | Ile<br>85 | Asp | Lys | Leu | Leu | Gln<br>90 | Lys | Thr | Lys | Ala | Gly | Gln<br>95 |

| | | | | | | | | | | | | |
|---|---|---|---|---|---|---|---|---|---|---|---|---|
| Ala | Leu | Gly | Ser | Ala | Glu | Ser | Ile | Val | Gln | Asn | Ala | Asn | Lys | Ala | Lys |
| | | | 100 | | | | 105 | | | | 110 | |
| Thr | Val | Leu | Ser | Gly | Ile | Gln | Ser | Ile | Leu | Gly | Ser | Val | Leu | Ala | Gly |
| | | | 115 | | | | 120 | | | | 125 | |
| Met | Asp | Leu | Asp | Glu | Ala | Leu | Gln | Asn | Asn | Ser | Asn | Gln | His | Ala | Leu |
| | 130 | | | | 135 | | | | 140 | | | |
| Ala | Lys | Ala | Gly | Leu | Glu | Leu | Thr | Asn | Ser | Leu | Ile | Glu | Asn | Ile | Ala |
| 145 | | | | | 150 | | | | 155 | | | | | 160 |
| Asn | Ser | Val | Lys | Thr | Leu | Asp | Glu | Phe | Gly | Glu | Gln | Ile | Ser | Gln | Phe |
| | | | | 165 | | | | | 170 | | | | 175 | |
| Gly | Ser | Lys | Leu | Gln | Asn | Ile | Lys | Gly | Leu | Gly | Thr | Leu | Gly | Asp | Lys |
| | | | 180 | | | | 185 | | | | 190 | |
| Leu | Lys | Asn | Ile | Gly | Gly | Leu | Asp | Lys | Ala | Gly | Leu | Gly | Leu | Asp | Val |
| | | 195 | | | | 200 | | | | 205 | | |
| Ile | Ser | Gly | Leu | Leu | Ser | Gly | Ala | Thr | Ala | Ala | Leu | Val | Leu | Ala | Asp |
| | 210 | | | | | 215 | | | | 220 | | | |
| Lys | Asn | Ala | Ser | Thr | Ala | Lys | Lys | Val | Gly | Ala | Gly | Phe | Glu | Leu | Ala |
| 225 | | | | | 230 | | | | 235 | | | | | 240 |
| Asn | Gln | Val | Val | Gly | Asn | Ile | Thr | Lys | Ala | Val | Ser | Ser | Tyr | Ile | Leu |
| | | | | 245 | | | | 250 | | | | | 255 | |
| Ala | Gln | Arg | Val | Ala | Ala | Gly | Leu | Ser | Ser | Thr | Gly | Pro | Val | Ala | Ala |
| | | | 260 | | | | | 265 | | | | 270 | |
| Leu | Ile | Ala | Ser | Thr | Val | Ser | Leu | Ala | Ile | Ser | Pro | Leu | Ala | Phe | Ala |
| | | 275 | | | | | 280 | | | | 285 | | |
| Gly | Ile | Ala | Asp | Lys | Phe | Asn | His | Ala | Lys | Ser | Leu | Glu | Ser | Tyr | Ala |
| | 290 | | | | | 295 | | | | 300 | | | |
| Glu | Arg | Phe | Lys | Lys | Leu | Gly | Tyr | Asp | Gly | Asp | Asn | Leu | Leu | Ala | Glu |
| 305 | | | | | 310 | | | | 315 | | | | | 320 |
| Tyr | Gln | Arg | Gly | Thr | Gly | Thr | Ile | Asp | Ala | Ser | Val | Thr | Ala | Ile | Asn |
| | | | | 325 | | | | 330 | | | | | 335 | |
| Thr | Ala | Leu | Ala | Ala | Ile | Ala | Gly | Gly | Val | Ser | Ala | Ala | Ala | Ala | Gly |
| | | | 340 | | | | 345 | | | | | 350 | |
| Ser | Val | Ile | Ala | Ser | Pro | Ile | Ala | Leu | Leu | Val | Ser | Gly | Ile | Thr | Gly |
| | | | 355 | | | | 360 | | | | 365 | | |
| Val | Ile | Ser | Thr | Ile | Leu | Gln | Tyr | Ser | Lys | Gln | Ala | Met | Phe | Glu | His |
| | 370 | | | | | 375 | | | | 380 | | | |
| Val | Ala | Asn | Lys | Ile | His | Asn | Lys | Ile | Val | Glu | Trp | Glu | Lys | Asn | Asn |
| 385 | | | | | 390 | | | | 395 | | | | | 400 |
| His | Gly | Lys | Asn | Tyr | Phe | Glu | Asn | Gly | Tyr | Asp | Ala | Arg | Tyr | Leu | Ala |
| | | | | 405 | | | | 410 | | | | | 415 | |
| Asn | Leu | Gln | Asp | Asn | Met | Lys | Phe | Leu | Leu | Asn | Leu | Asn | Lys | Glu | Leu |
| | | | 420 | | | | 425 | | | | 430 | |
| Gln | Ala | Glu | Arg | Val | Ile | Ala | Ile | Thr | Gln | Gln | Gln | Trp | Asp | Asn | Asn |
| | | 435 | | | | 440 | | | | 445 | | |
| Ile | Gly | Asp | Leu | Ala | Gly | Ile | Ser | Arg | Leu | Gly | Glu | Lys | Val | Leu | Ser |
| | 450 | | | | 455 | | | | 460 | | | |
| Gly | Lys | Ala | Tyr | Val | Asp | Ala | Phe | Glu | Glu | Gly | Lys | His | Ile | Lys | Ala |
| 465 | | | | | 470 | | | | 475 | | | | | 480 |
| Asp | Lys | Leu | Val | Gln | Leu | Asp | Ser | Ala | Asn | Gly | Ile | Ile | Asp | Val | Ser |
| | | | | 485 | | | | 490 | | | | | 495 | |
| Asn | Ser | Gly | Lys | Ala | Lys | Thr | Gln | His | Ile | Leu | Phe | Arg | Thr | Pro | Leu |
| | | | 500 | | | | 505 | | | | 510 | |
| Leu | Thr | Pro | Gly | Thr | Glu | His | Arg | Glu | Arg | Val | Gln | Thr | Gly | Lys | Tyr |
| | | 515 | | | | 520 | | | | 525 | | |

-continued

```
Glu  Tyr  Ile  Thr  Lys  Leu  Asn  Ile  Asn  Arg  Val  Asp  Ser  Trp  Lys  Ile
     530                     535                    540

Thr  Asp  Gly  Ala  Ala  Ser  Ser  Thr  Phe  Asp  Leu  Thr  Asn  Val  Val  Gln
545                      550                    555                          560

Arg  Ile  Gly  Ile  Glu  Leu  Asp  Asn  Ala  Gly  Asn  Val  Thr  Lys  Thr  Lys
               565                         570                    575

Glu  Thr  Lys  Ile  Ile  Ala  Lys  Leu  Gly  Glu  Gly  Asp  Asp  Asn  Val  Phe
               580                     585                    590

Val  Gly  Ser  Gly  Thr  Thr  Glu  Ile  Asp  Gly  Gly  Glu  Gly  Tyr  Asp  Arg
          595                          600                    605

Val  His  Tyr  Ser  Arg  Gly  Asn  Tyr  Gly  Ala  Leu  Thr  Ile  Asp  Ala  Thr
     610                          615                    620

Lys  Glu  Thr  Glu  Gln  Gly  Ser  Tyr  Thr  Val  Asn  Arg  Phe  Val  Glu  Thr
625                      630                         635                          640

Gly  Lys  Ala  Leu  His  Glu  Val  Thr  Ser  Thr  His  Thr  Ala  Leu  Val  Gly
               645                          650                    655

Asn  Arg  Glu  Glu  Lys  Ile  Glu  Tyr  Arg  His  Ser  Asn  Asn  Gln  His  His
               660                          665                    670

Ala  Gly  Tyr  Tyr  Thr  Lys  Asp  Thr  Leu  Lys  Ala  Val  Glu  Glu  Ile  Ile
               675                          680                    685

Gly  Thr  Ser  His  Asn  Asp  Ile  Phe  Lys  Gly  Ser  Lys  Phe  Asn  Asp  Ala
690                               695                    700

Phe  Asn  Gly  Gly  Asp  Gly  Val  Asp  Thr  Ile  Asp  Gly  Asn  Asp  Gly  Asn
705                          710                    715                          720

Asp  Arg  Leu  Phe  Gly  Gly  Lys  Gly  Asp  Asp  Ile  Leu  Asp  Gly  Gly  Asn
               725                          730                    735

Gly  Asp  Asp  Phe  Ile  Asp  Gly  Gly  Lys  Gly  Asn  Asp  Leu  Leu  His  Gly
               740                          745                    750

Gly  Lys  Gly  Asp  Asp  Ile  Phe  Val  His  Arg  Lys  Gly  Asp  Gly  Asn  Asp
               755                          760                    765

Ile  Ile  Thr  Asp  Ser  Asp  Gly  Asn  Asp  Lys  Leu  Ser  Phe  Ser  Asp  Ser
770                               775                    780

Asn  Leu  Lys  Asp  Leu  Thr  Phe  Glu  Lys  Val  Lys  His  Asn  Leu  Val  Ile
785                      790                         795                          800

Thr  Asn  Ser  Lys  Lys  Glu  Lys  Val  Thr  Ile  Gln  Asn  Trp  Phe  Arg  Glu
                    805                    810                         815

Ala  Asp  Phe  Ala  Lys  Glu  Val  Pro  Asn  Tyr  Lys  Ala  Thr  Lys  Asp  Glu
               820                    825                         830

Lys  Ile  Glu  Glu  Ile  Ile  Gly  Gln  Asn  Gly  Glu  Arg  Ile  Thr  Ser  Lys
          835                          840                    845

Gln  Val  Asp  Asp  Leu  Ile  Ala  Lys  Gly  Asn  Gly  Lys  Ile  Thr  Gln  Asp
     850                          855                    860

Glu  Leu  Ser  Lys  Val  Val  Asp  Asn  Tyr  Glu  Leu  Leu  Lys  His  Ser  Lys
865                           870                         875                          880

Asn  Val  Thr  Asn  Ser  Leu  Asp  Lys  Leu  Ile  Ser  Ser  Val  Ser  Ala  Phe
                    885                         890                          895

Thr  Ser  Ser  Asn  Asp  Ser  Arg  Asn  Val  Leu  Val  Ala  Pro  Thr  Ser  Met
               900                    905                         910

Leu  Asp  Gln  Ser  Leu  Ser  Ser  Leu  Gln  Phe  Ala  Arg  Gly  Ser
               915                    920                    925
```

( 2 ) INFORMATION FOR SEQ ID NO:7:

( i ) SEQUENCE CHARACTERISTICS:

5,723,129

41

42

-continued ( A ) LENGTH: 2934 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..2931

( x i ) SEQUENCE DESCRIPTION: SEQ ID NO:7:

| ATG | GCT | ACT | GTT | ATA | GAT | CTA | AGC | TTC | CCA | AAA | ACT | GGG | GCA | AAA | AAA | 48 |
| Met | Ala | Thr | Val | Ile | Asp | Leu | Ser | Phe | Pro | Lys | Thr | Gly | Ala | Lys | Lys | |
| 1 | | | | 5 | | | | | 10 | | | | | 15 | | |

| ATT | ATC | CTC | TAT | ATT | CCC | CAA | AAT | TAC | CAA | TAT | GAT | ACT | GAA | CAA | GGT | 96 |
| Ile | Ile | Leu | Tyr | Ile | Pro | Gln | Asn | Tyr | Gln | Tyr | Asp | Thr | Glu | Gln | Gly | |
| | | | 20 | | | | | 25 | | | | | 30 | | | |

| AAT | GGT | TTA | CAG | GAT | TTA | GTC | AAA | GCG | GCC | GAA | GAG | TTG | GGG | ATT | GAG | 144 |
| Asn | Gly | Leu | Gln | Asp | Leu | Val | Lys | Ala | Ala | Glu | Glu | Leu | Gly | Ile | Glu | |
| | | | 35 | | | | 40 | | | | | 45 | | | | |

| GTA | CAA | AGA | GAA | GAA | CGC | AAT | AAT | ATT | GCA | ACA | GCT | CAA | ACC | AGT | TTA | 192 |
| Val | Gln | Arg | Glu | Glu | Arg | Asn | Asn | Ile | Ala | Thr | Ala | Gln | Thr | Ser | Leu | |
| | 50 | | | | | 55 | | | | | 60 | | | | | |

| GGC | ACG | ATT | CAA | ACC | GCT | ATT | GGC | TTA | ACT | GAG | CGT | GGC | ATT | GTG | TTA | 240 |
| Gly | Thr | Ile | Gln | Thr | Ala | Ile | Gly | Leu | Thr | Glu | Arg | Gly | Ile | Val | Leu | |
| 65 | | | | | 70 | | | | | 75 | | | | | 80 | |

| TCC | GCT | CCA | CAA | ATT | GAT | AAA | TTG | CTA | CAG | AAA | ACT | AAA | GCA | GGC | CAA | 288 |
| Ser | Ala | Pro | Gln | Ile | Asp | Lys | Leu | Leu | Gln | Lys | Thr | Lys | Ala | Gly | Gln | |
| | | | | 85 | | | | | 90 | | | | | 95 | | |

| GCA | TTA | GGT | TCT | GCC | GAA | AGC | ATT | GTA | CAA | AAT | GCA | AAT | AAA | GCC | AAA | 336 |
| Ala | Leu | Gly | Ser | Ala | Glu | Ser | Ile | Val | Gln | Asn | Ala | Asn | Lys | Ala | Lys | |
| | | | 100 | | | | | 105 | | | | | 110 | | | |

| ACT | GTA | TTA | TCT | GGC | ATT | CAA | TCT | ATT | TTA | GGC | TCA | GTA | TTG | GCT | GGA | 384 |
| Thr | Val | Leu | Ser | Gly | Ile | Gln | Ser | Ile | Leu | Gly | Ser | Val | Leu | Ala | Gly | |
| | | 115 | | | | | 120 | | | | | 125 | | | | |

| ATG | GAT | TTA | GAT | GAG | GCC | TTA | CAG | AAT | AAC | AGC | AAC | CAA | CAT | GCT | CTT | 432 |
| Met | Asp | Leu | Asp | Glu | Ala | Leu | Gln | Asn | Asn | Ser | Asn | Gln | His | Ala | Leu | |
| | 130 | | | | | 135 | | | | | 140 | | | | | |

| GCT | AAA | GCT | GGC | TTG | GAG | CTA | ACA | AAT | TCA | TTA | ATT | GAA | AAT | ATT | GCT | 480 |
| Ala | Lys | Ala | Gly | Leu | Glu | Leu | Thr | Asn | Ser | Leu | Ile | Glu | Asn | Ile | Ala | |
| 145 | | | | | 150 | | | | | 155 | | | | | 160 | |

| AAT | TCA | GTA | AAA | ACA | CTT | GAC | GAA | TTT | GGT | GAG | CAA | ATT | AGT | CAA | TTT | 528 |
| Asn | Ser | Val | Lys | Thr | Leu | Asp | Glu | Phe | Gly | Glu | Gln | Ile | Ser | Gln | Phe | |
| | | | | 165 | | | | | 170 | | | | | 175 | | |

| GGT | TCA | AAA | CTA | CAA | AAT | ATC | AAA | GGC | TTA | GGG | ACT | TTA | GGA | GAC | AAA | 576 |
| Gly | Ser | Lys | Leu | Gln | Asn | Ile | Lys | Gly | Leu | Gly | Thr | Leu | Gly | Asp | Lys | |
| | | | 180 | | | | | 185 | | | | | 190 | | | |

| CTC | AAA | AAT | ATC | GGT | GGA | CTT | GAT | AAA | GCT | GGC | CTT | GGT | TTA | GAT | GTT | 624 |
| Leu | Lys | Asn | Ile | Gly | Gly | Leu | Asp | Lys | Ala | Gly | Leu | Gly | Leu | Asp | Val | |
| | | 195 | | | | | 200 | | | | | 205 | | | | |

| ATC | TCA | GGG | CTA | TTA | TCG | GGC | GCA | ACA | GCT | GCA | CTT | GTA | CTT | GCA | GAT | 672 |
| Ile | Ser | Gly | Leu | Leu | Ser | Gly | Ala | Thr | Ala | Ala | Leu | Val | Leu | Ala | Asp | |
| | 210 | | | | | 215 | | | | | 220 | | | | | |

| AAA | AAT | GCT | TCA | ACA | GCT | AAA | AAA | GTG | GGT | GCG | GGT | TTT | GAA | TTG | GCA | 720 |
| Lys | Asn | Ala | Ser | Thr | Ala | Lys | Lys | Val | Gly | Ala | Gly | Phe | Glu | Leu | Ala | |
| 225 | | | | | 230 | | | | | 235 | | | | | 240 | |

| AAC | CAA | GTT | GTT | GGT | AAT | ATT | ACC | AAA | GCC | GTT | TCT | TCT | TAC | ATT | TTA | 768 |
| Asn | Gln | Val | Val | Gly | Asn | Ile | Thr | Lys | Ala | Val | Ser | Ser | Tyr | Ile | Leu | |
| | | | | 245 | | | | | 250 | | | | | 255 | | |

| GCC | CAA | CGT | GTT | GCA | GCA | GGT | TTA | TCT | TCA | ACT | GGG | CCT | GTG | GCT | GCT | 816 |
| Ala | Gln | Arg | Val | Ala | Ala | Gly | Leu | Ser | Ser | Thr | Gly | Pro | Val | Ala | Ala | |
| | | | | | | | | | | | | | | | | |
| | | | | | | | | | | | | | | | | |
| | | | | | | | | | | | | | | | | |
| | | | 260 | | | | | 265 | | | | | 270 | | | |

| | | | | | | | | | | | | | | | | |
|---|---|---|---|---|---|---|---|---|---|---|---|---|---|---|---|---|
| TTA | ATT | GCT | TCT | ACT | GTT | TCT | CTT | GCG | ATT | AGC | CCA | TTA | GCA | TTT | GCC | 864 |
| Leu | Ile | Ala | Ser | Thr | Val | Ser | Leu | Ala | Ile | Ser | Pro | Leu | Ala | Phe | Ala | |
| | | 275 | | | | | 280 | | | | | 285 | | | | |
| GGT | ATT | GCC | GAT | AAA | TTT | AAT | CAT | GCA | AAA | AGT | TTA | GAG | AGT | TAT | GCC | 912 |
| Gly | Ile | Ala | Asp | Lys | Phe | Asn | His | Ala | Lys | Ser | Leu | Glu | Ser | Tyr | Ala | |
| | | 290 | | | | | 295 | | | | | 300 | | | | |
| GAA | CGC | TTT | AAA | AAA | TTA | GGC | TAT | GAC | GGA | GAT | AAT | TTA | TTA | GCA | GAA | 960 |
| Glu | Arg | Phe | Lys | Lys | Leu | Gly | Tyr | Asp | Gly | Asp | Asn | Leu | Leu | Ala | Glu | |
| 305 | | | | | 310 | | | | | 315 | | | | | 320 | |
| TAT | CAG | CGG | GGA | ACA | GGG | ACT | ATT | GAT | GCA | TCG | GTT | ACT | GCA | ATT | AAT | 1008 |
| Tyr | Gln | Arg | Gly | Thr | Gly | Thr | Ile | Asp | Ala | Ser | Val | Thr | Ala | Ile | Asn | |
| | | | | 325 | | | | | 330 | | | | | 335 | | |
| ACC | GCA | TTG | GCC | GCT | ATT | GCT | GGT | GGT | GTG | TCT | GCT | GCT | GCA | GCC | GGC | 1056 |
| Thr | Ala | Leu | Ala | Ala | Ile | Ala | Gly | Gly | Val | Ser | Ala | Ala | Ala | Ala | Gly | |
| | | | 340 | | | | | 345 | | | | | 350 | | | |
| TCG | GTT | ATT | GCT | TCA | CCG | ATT | GCC | TTA | TTA | GTA | TCT | GGG | ATT | ACC | GGT | 1104 |
| Ser | Val | Ile | Ala | Ser | Pro | Ile | Ala | Leu | Leu | Val | Ser | Gly | Ile | Thr | Gly | |
| | | 355 | | | | | 360 | | | | | 365 | | | | |
| GTA | ATT | TCT | ACG | ATT | CTG | CAA | TAT | TCT | AAA | CAA | GCA | ATG | TTT | GAG | CAC | 1152 |
| Val | Ile | Ser | Thr | Ile | Leu | Gln | Tyr | Ser | Lys | Gln | Ala | Met | Phe | Glu | His | |
| | | 370 | | | | | 375 | | | | | 380 | | | | |
| GTT | GCA | AAT | AAA | ATT | CAT | AAC | AAA | ATT | GTA | GAA | TGG | GAA | AAA | AAT | AAT | 1200 |
| Val | Ala | Asn | Lys | Ile | His | Asn | Lys | Ile | Val | Glu | Trp | Glu | Lys | Asn | Asn | |
| 385 | | | | | 390 | | | | | 395 | | | | | 400 | |
| CAC | GGT | AAG | AAC | TAC | TTT | GAA | AAT | GGT | TAC | GAT | GCC | CGT | TAT | CTT | GCG | 1248 |
| His | Gly | Lys | Asn | Tyr | Phe | Glu | Asn | Gly | Tyr | Asp | Ala | Arg | Tyr | Leu | Ala | |
| | | | | 405 | | | | | 410 | | | | | 415 | | |
| AAT | TTA | CAA | GAT | AAT | ATG | AAA | TTC | TTA | CTG | AAC | TTA | AAC | AAA | GAG | TTA | 1296 |
| Asn | Leu | Gln | Asp | Asn | Met | Lys | Phe | Leu | Leu | Asn | Leu | Asn | Lys | Glu | Leu | |
| | | | 420 | | | | | 425 | | | | | 430 | | | |
| CAG | GCA | GAA | CGT | GTC | ATC | GCT | ATT | ACT | CAG | CAG | CAA | TGG | GAT | AAC | AAC | 1344 |
| Gln | Ala | Glu | Arg | Val | Ile | Ala | Ile | Thr | Gln | Gln | Gln | Trp | Asp | Asn | Asn | |
| | | 435 | | | | | 440 | | | | | 445 | | | | |
| ATT | GGT | GAT | TTA | GCT | GGT | ATT | AGC | CGT | TTA | GGT | GAA | AAA | GTC | CTT | AGT | 1392 |
| Ile | Gly | Asp | Leu | Ala | Gly | Ile | Ser | Arg | Leu | Gly | Glu | Lys | Val | Leu | Ser | |
| | | 450 | | | | | 455 | | | | | 460 | | | | |
| GGT | AAA | GCC | TAT | GTG | GAT | GCG | TTT | GAA | GAA | GGC | AAA | CAC | ATT | AAA | GCC | 1440 |
| Gly | Lys | Ala | Tyr | Val | Asp | Ala | Phe | Glu | Glu | Gly | Lys | His | Ile | Lys | Ala | |
| 465 | | | | | 470 | | | | | 475 | | | | | 480 | |
| GAT | AAA | TTA | GTA | CAG | TTG | GAT | TCG | GCA | AAC | GGT | ATT | ATT | GAT | GTG | AGT | 1488 |
| Asp | Lys | Leu | Val | Gln | Leu | Asp | Ser | Ala | Asn | Gly | Ile | Ile | Asp | Val | Ser | |
| | | | | 485 | | | | | 490 | | | | | 495 | | |
| AAT | TCG | GGT | AAA | GCG | AAA | ACT | CAG | CAT | ATC | TTA | TTC | AGA | ACG | CCA | TTA | 1536 |
| Asn | Ser | Gly | Lys | Ala | Lys | Thr | Gln | His | Ile | Leu | Phe | Arg | Thr | Pro | Leu | |
| | | | 500 | | | | | 505 | | | | | 510 | | | |
| TTG | ACG | CCG | GGA | ACA | GAG | CAT | CGT | GAA | CGC | GTA | CAA | ACA | GGT | AAA | TAT | 1584 |
| Leu | Thr | Pro | Gly | Thr | Glu | His | Arg | Glu | Arg | Val | Gln | Thr | Gly | Lys | Tyr | |
| | | 515 | | | | | 520 | | | | | 525 | | | | |
| GAA | TAT | ATT | ACC | AAG | CTC | AAT | ATT | AAC | CGT | GTA | GAT | AGC | TGG | AAA | ATT | 1632 |
| Glu | Tyr | Ile | Thr | Lys | Leu | Asn | Ile | Asn | Arg | Val | Asp | Ser | Trp | Lys | Ile | |
| | | 530 | | | | | 535 | | | | | 540 | | | | |
| ACA | GAT | GGT | GCA | GCA | AGT | TCT | ACC | TTT | GAT | TTA | ACT | AAC | GTT | GTT | CAG | 1680 |
| Thr | Asp | Gly | Ala | Ala | Ser | Ser | Thr | Phe | Asp | Leu | Thr | Asn | Val | Val | Gln | |
| 545 | | | | | 550 | | | | | 555 | | | | | 560 | |
| CGT | ATT | GGT | ATT | GAA | TTA | GAC | AAT | GCT | GGA | AAT | GTA | ACT | AAA | ACC | AAA | 1728 |
| Arg | Ile | Gly | Ile | Glu | Leu | Asp | Asn | Ala | Gly | Asn | Val | Thr | Lys | Thr | Lys | |
| | | | | 565 | | | | | 570 | | | | | 575 | | |
| GAA | ACA | AAA | ATT | ATT | GCC | AAA | CTT | GGT | GAA | GGT | GAT | GAC | AAC | GTA | TTT | 1776 |
| Glu | Thr | Lys | Ile | Ile | Ala | Lys | Leu | Gly | Glu | Gly | Asp | Asp | Asn | Val | Phe | |
| | | | | | | | | | 585 | | | | | 590 | | |

```
GTT GGT TCT GGT ACG ACG GAA ATT GAT GGC GGT GAA GGT TAC GAC CGA    1824
Val Gly Ser Gly Thr Thr Glu Ile Asp Gly Gly Glu Gly Tyr Asp Arg
        595         600                 605

GTT CAC TAT AGC CGT GGA AAC TAT GGT GCT TTA ACT ATT GAT GCA ACC    1872
Val His Tyr Ser Arg Gly Asn Tyr Gly Ala Leu Thr Ile Asp Ala Thr
    610                 615             620

AAA GAG ACC GAG CAA GGT AGT TAT ACC GTA AAT CGT TTC GTA GAA ACC    1920
Lys Glu Thr Glu Gln Gly Ser Tyr Thr Val Asn Arg Phe Val Glu Thr
625                 630                 635                 640

GGT AAA GCA CTA CAC GAA GTG ACT TCA ACC CAT ACC GCA TTA GTG GGC    1968
Gly Lys Ala Leu His Glu Val Thr Ser Thr His Thr Ala Leu Val Gly
            645                 650                 655

AAC CGT GAA GAA AAA ATA GAA TAT CGT CAT AGC AAT AAC CAG CAC CAT    2016
Asn Arg Glu Glu Lys Ile Glu Tyr Arg His Ser Asn Asn Gln His His
                660                 665                 670

GCC GGT TAT TAC ACC AAA GAT ACC TTG AAA GCT GTT GAA GAA ATT ATC    2064
Ala Gly Tyr Tyr Thr Lys Asp Thr Leu Lys Ala Val Glu Glu Ile Ile
            675                 680                 685

GGT ACA TCA CAT AAC GAT ATC TTT AAA GGT AGT AAG TTC AAT GAT GCC    2112
Gly Thr Ser His Asn Asp Ile Phe Lys Gly Ser Lys Phe Asn Asp Ala
        690                 695                 700

TTT AAC GGT GGT GAT GGT GTC GAT ACT ATT GAC GGT AAC GAC GGC AAT    2160
Phe Asn Gly Gly Asp Gly Val Asp Thr Ile Asp Gly Asn Asp Gly Asn
705                 710                 715                 720

GAC CGC TTA TTT GGT GGT AAA GGC GAT GAT ATT CTC GAT GGT GGA AAT    2208
Asp Arg Leu Phe Gly Gly Lys Gly Asp Asp Ile Leu Asp Gly Gly Asn
            725                 730                 735

GGT GAT GAT TTT ATC GAT GGC GGT AAA GGC AAC GAC CTA TTA CAC GGT    2256
Gly Asp Asp Phe Ile Asp Gly Gly Lys Gly Asn Asp Leu Leu His Gly
        740                 745                 750

GGC AAG GGC GAT GAT ATT TTC GTT CAC CGT AAA GGC GAT GGT AAT GAT    2304
Gly Lys Gly Asp Asp Ile Phe Val His Arg Lys Gly Asp Gly Asn Asp
    755                 760                 765

ATT ATT ACC GAT TCT GAC GGC AAT GAT AAA TTA TCA TTC TCT GAT TCG    2352
Ile Ile Thr Asp Ser Asp Gly Asn Asp Lys Leu Ser Phe Ser Asp Ser
770                 775                 780

AAC TTA AAA GAT TTA ACA TTT GAA AAA GTT AAA CAT AAT CTT GTC ATC    2400
Asn Leu Lys Asp Leu Thr Phe Glu Lys Val Lys His Asn Leu Val Ile
785                 790                 795                 800

ACG AAT AGC AAA AAA GAG AAA GTG ACC ATT CAA AAC TGG TTC CGA GAG    2448
Thr Asn Ser Lys Lys Glu Lys Val Thr Ile Gln Asn Trp Phe Arg Glu
            805                 810                 815

GCT GAT TTT GCT AAA GAA GTG CCT AAT TAT AAA GCA ACT AAA GAT GAG    2496
Ala Asp Phe Ala Lys Glu Val Pro Asn Tyr Lys Ala Thr Lys Asp Glu
        820                 825                 830

AAA ATC GAA GAA ATC ATC GGT CAA AAT GGC GAG CGG ATC ACC TCA AAG    2544
Lys Ile Glu Glu Ile Ile Gly Gln Asn Gly Glu Arg Ile Thr Ser Lys
    835                 840                 845

CAA GTT GAT GAT CTT ATC GCA AAA GGT AAC GGC AAA ATT ACC CAA GAT    2592
Gln Val Asp Asp Leu Ile Ala Lys Gly Asn Gly Lys Ile Thr Gln Asp
850                 855                 860

GAG CTA TCA AAA GTT GTT GAT AAC TAT GAA TTG CTC AAA CAT AGC AAA    2640
Glu Leu Ser Lys Val Val Asp Asn Tyr Glu Leu Leu Lys His Ser Lys
865                 870                 875                 880

AAT GTG ACA AAC AGC TTA GAT AAG TTA ATC TCA TCT GTA AGT GCA TTT    2688
Asn Val Thr Asn Ser Leu Asp Lys Leu Ile Ser Ser Val Ser Ala Phe
            885                 890                 895

ACC TCG TCT AAT GAT TCG AGA AAT GTA TTA GTG GCT CCA ACT TCA ATG    2736
Thr Ser Ser Asn Asp Ser Arg Asn Val Leu Val Ala Pro Thr Ser Met
        900                 905                 910
```

```
TTG GAT CAA AGT TTA TCT TCT CTT CAA TTT GCT AGG GGA TCT CAG CAT    2784
Leu Asp Gln Ser Leu Ser Ser Leu Gln Phe Ala Arg Gly Ser Gln His
        915             920                 925

TGG AGC TAC GGC CTG CGC CCT GGC AGC GGT TCT CAA GAT TGG AGC TAC    2832
Trp Ser Tyr Gly Leu Arg Pro Gly Ser Gly Ser Gln Asp Trp Ser Tyr
930                     935                 940

GGC CTG CGT CCG GGT GGC TCT AGC CAG CAT TGG AGC TAC GGC CTG CGC    2880
Gly Leu Arg Pro Gly Gly Ser Ser Gln His Trp Ser Tyr Gly Leu Arg
945                 950                 955                 960

CCT GGC AGC GGT AGC CAA GAT TGG AGC TAC GGC CTG CGT CCG GGT GGA    2928
Pro Gly Ser Gly Ser Gln Asp Trp Ser Tyr Gly Leu Arg Pro Gly Gly
                965                 970                 975

TCC TAG                                                            2934
Ser
```

( 2 ) INFORMATION FOR SEQ ID NO:8:

( i ) SEQUENCE CHARACTERISTICS:
        ( A ) LENGTH: 977 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Ala Thr Val Ile Asp Leu Ser Phe Pro Lys Thr Gly Ala Lys Lys
1               5                   10                  15

Ile Ile Leu Tyr Ile Pro Gln Asn Tyr Gln Tyr Asp Thr Glu Gln Gly
                20                  25                  30

Asn Gly Leu Gln Asp Leu Val Lys Ala Ala Glu Glu Leu Gly Ile Glu
            35                  40                  45

Val Gln Arg Glu Glu Arg Asn Asn Ile Ala Thr Ala Gln Thr Ser Leu
        50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255
```

-continued

| | | | | | | | | | | | | | | |
|---|---|---|---|---|---|---|---|---|---|---|---|---|---|---|
| Ala | Gln | Arg | Val 260 | Ala | Ala | Gly | Leu 265 | Ser | Ser | Thr | Gly | Pro 270 | Val | Ala | Ala |
| Leu | Ile | Ala 275 | Ser | Thr | Val | Ser | Leu 280 | Ala | Ile | Ser | Pro 285 | Leu | Ala | Phe | Ala |
| Gly | Ile | Ala 290 | Asp | Lys | Phe | Asn 295 | His | Ala | Lys | Ser 300 | Leu | Glu | Ser | Tyr | Ala |
| Glu 305 | Arg | Phe | Lys | Lys | Leu 310 | Gly | Tyr | Asp | Gly 315 | Asp | Asn | Leu | Leu | Ala | Glu 320 |
| Tyr | Gln | Arg | Gly | Thr 325 | Gly | Thr | Ile | Asp | Ala 330 | Ser | Val | Thr | Ala | Ile 335 | Asn |
| Thr | Ala | Leu | Ala 340 | Ala | Ile | Ala | Gly | Gly 345 | Val | Ser | Ala | Ala | Ala 350 | Ala | Gly |
| Ser | Val | Ile 355 | Ala | Ser | Pro | Ile 360 | Ala | Leu | Leu | Val | Ser 365 | Gly | Ile | Thr | Gly |
| Val | Ile | Ser 370 | Thr | Ile | Leu | Gln 375 | Tyr | Ser | Lys | Gln 380 | Ala | Met | Phe | Glu | His |
| Val 385 | Ala | Asn | Lys | Ile | His 390 | Asn | Lys | Ile | Val 395 | Glu | Trp | Glu | Lys | Asn | Asn 400 |
| His | Gly | Lys | Asn 405 | Tyr | Phe | Glu | Asn | Gly 410 | Tyr | Asp | Ala | Arg | Tyr 415 | Leu | Ala |
| Asn | Leu | Gln | Asp 420 | Asn | Met | Lys | Phe | Leu 425 | Leu | Asn | Leu | Asn | Lys 430 | Glu | Leu |
| Gln | Ala | Glu 435 | Arg | Val | Ile | Ala | Ile 440 | Thr | Gln | Gln | Gln | Trp 445 | Asp | Asn | Asn |
| Ile | Gly 450 | Asp | Leu | Ala | Gly | Ile 455 | Ser | Arg | Leu | Gly | Glu 460 | Lys | Val | Leu | Ser |
| Gly 465 | Lys | Ala | Tyr | Val | Asp 470 | Ala | Phe | Glu | Glu 475 | Gly | Lys | His | Ile | Lys | Ala 480 |
| Asp | Lys | Leu | Val | Gln 485 | Leu | Asp | Ser | Ala | Asn 490 | Gly | Ile | Ile | Asp | Val 495 | Ser |
| Asn | Ser | Gly | Lys 500 | Ala | Lys | Thr | Gln | His 505 | Ile | Leu | Phe | Arg | Thr 510 | Pro | Leu |
| Leu | Thr | Pro 515 | Gly | Thr | Glu | His | Arg 520 | Glu | Arg | Val | Gln | Thr 525 | Gly | Lys | Tyr |
| Glu | Tyr 530 | Ile | Thr | Lys | Leu | Asn 535 | Ile | Asn | Arg | Val | Asp 540 | Ser | Trp | Lys | Ile |
| Thr 545 | Asp | Gly | Ala | Ala | Ser 550 | Ser | Thr | Phe | Asp | Leu 555 | Thr | Asn | Val | Val | Gln 560 |
| Arg | Ile | Gly | Ile | Glu 565 | Leu | Asp | Asn | Ala | Gly 570 | Asn | Val | Thr | Lys | Thr 575 | Lys |
| Glu | Thr | Lys | Ile 580 | Ile | Ala | Lys | Leu | Gly 585 | Glu | Gly | Asp | Asp | Asn 590 | Val | Phe |
| Val | Gly | Ser 595 | Gly | Thr | Thr | Glu | Ile 600 | Asp | Gly | Gly | Glu | Gly 605 | Tyr | Asp | Arg |
| Val | His 610 | Tyr | Ser | Arg | Gly | Asn 615 | Tyr | Gly | Ala | Leu | Thr 620 | Ile | Asp | Ala | Thr |
| Lys 625 | Glu | Thr | Glu | Gln | Gly 630 | Ser | Tyr | Thr | Val | Asn 635 | Arg | Phe | Val | Glu | Thr 640 |
| Gly | Lys | Ala | Leu | His 645 | Glu | Val | Thr | Ser | Thr 650 | His | Thr | Ala | Leu | Val 655 | Gly |
| Asn | Arg | Glu | Glu 660 | Lys | Ile | Glu | Tyr | Arg 665 | His | Ser | Asn | Asn | Gln 670 | His | His |
| Ala | Gly | Tyr 675 | Tyr | Thr | Lys | Asp | Thr 680 | Leu | Lys | Ala | Val | Glu 685 | Glu | Ile | Ile |

| Gly | Thr | Ser | His | Asn | Asp | Ile | Phe | Lys | Gly | Ser | Lys | Phe | Asn | Asp | Ala |
|---|---|---|---|---|---|---|---|---|---|---|---|---|---|---|---|
| | 690 | | | | | 695 | | | | 700 | | | | | |
| Phe | Asn | Gly | Gly | Asp | Gly | Val | Asp | Thr | Ile | Asp | Gly | Asn | Asp | Gly | Asn |
| 705 | | | | | 710 | | | | 715 | | | | | | 720 |
| Asp | Arg | Leu | Phe | Gly | Gly | Lys | Gly | Asp | Asp | Ile | Leu | Asp | Gly | Gly | Asn |
| | | | | 725 | | | | | 730 | | | | | 735 | |
| Gly | Asp | Asp | Phe | Ile | Asp | Gly | Gly | Lys | Gly | Asn | Asp | Leu | Leu | His | Gly |
| | | | 740 | | | | | 745 | | | | | 750 | | |
| Gly | Lys | Gly | Asp | Asp | Ile | Phe | Val | His | Arg | Lys | Gly | Asp | Gly | Asn | Asp |
| | | 755 | | | | | 760 | | | | | 765 | | | |
| Ile | Ile | Thr | Asp | Ser | Asp | Gly | Asn | Asp | Lys | Leu | Ser | Phe | Ser | Asp | Ser |
| | 770 | | | | | 775 | | | | | 780 | | | | |
| Asn | Leu | Lys | Asp | Leu | Thr | Phe | Glu | Lys | Val | Lys | His | Asn | Leu | Val | Ile |
| 785 | | | | | 790 | | | | | 795 | | | | | 800 |
| Thr | Asn | Ser | Lys | Lys | Glu | Lys | Val | Thr | Ile | Gln | Asn | Trp | Phe | Arg | Glu |
| | | | | 805 | | | | | 810 | | | | | 815 | |
| Ala | Asp | Phe | Ala | Lys | Glu | Val | Pro | Asn | Tyr | Lys | Ala | Thr | Lys | Asp | Glu |
| | | | 820 | | | | | 825 | | | | | 830 | | |
| Lys | Ile | Glu | Glu | Ile | Ile | Gly | Gln | Asn | Gly | Glu | Arg | Ile | Thr | Ser | Lys |
| | | 835 | | | | | 840 | | | | | 845 | | | |
| Gln | Val | Asp | Asp | Leu | Ile | Ala | Lys | Gly | Asn | Gly | Lys | Ile | Thr | Gln | Asp |
| | 850 | | | | | 855 | | | | | 860 | | | | |
| Glu | Leu | Ser | Lys | Val | Val | Asp | Asn | Tyr | Glu | Leu | Leu | Lys | His | Ser | Lys |
| 865 | | | | | 870 | | | | | 875 | | | | | 880 |
| Asn | Val | Thr | Asn | Ser | Leu | Asp | Lys | Leu | Ile | Ser | Ser | Val | Ser | Ala | Phe |
| | | | | 885 | | | | | 890 | | | | | 895 | |
| Thr | Ser | Ser | Asn | Asp | Ser | Arg | Asn | Val | Leu | Val | Ala | Pro | Thr | Ser | Met |
| | | | 900 | | | | | 905 | | | | | 910 | | |
| Leu | Asp | Gln | Ser | Leu | Ser | Ser | Leu | Gln | Phe | Ala | Arg | Gly | Ser | Gln | His |
| | | | 915 | | | | | 920 | | | | | 925 | | |
| Trp | Ser | Tyr | Gly | Leu | Arg | Pro | Gly | Ser | Gly | Ser | Gln | Asp | Trp | Ser | Tyr |
| | 930 | | | | | 935 | | | | | 940 | | | | |
| Gly | Leu | Arg | Pro | Gly | Gly | Ser | Ser | Gln | His | Trp | Ser | Tyr | Gly | Leu | Arg |
| 945 | | | | | 950 | | | | | 955 | | | | | 960 |
| Pro | Gly | Ser | Gly | Ser | Gln | Asp | Trp | Ser | Tyr | Gly | Leu | Arg | Pro | Gly | Gly |
| | | | | 965 | | | | | 970 | | | | | 975 | |
| Ser | | | | | | | | | | | | | | | |

( 2 ) INFORMATION FOR SEQ ID NO:9:

( i ) SEQUENCE CHARACTERISTICS:
    ( A ) LENGTH: 1635 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 1..1632

( x i ) SEQUENCE DESCRIPTION: SEQ ID NO:9:

| ATG | GCT | ACT | GTT | ATA | GAT | CTA | AGC | TTC | CCA | AAA | ACT | GGG | GCA | AAA | AAA | 48 |
|---|---|---|---|---|---|---|---|---|---|---|---|---|---|---|---|---|
| Met | Ala | Thr | Val | Ile | Asp | Leu | Ser | Phe | Pro | Lys | Thr | Gly | Ala | Lys | Lys | |
| 1 | | | | 5 | | | | | 10 | | | | | 15 | | |

| ATT | ATC | CTC | TAT | ATT | CCC | CAA | AAT | TAC | CAA | TAT | GAT | ACT | GAA | CAA | GGT | 96 |
|---|---|---|---|---|---|---|---|---|---|---|---|---|---|---|---|---|
| Ile | Ile | Leu | Tyr | Ile | Pro | Gln | Asn | Tyr | Gln | Tyr | Asp | Thr | Glu | Gln | Gly | |

|  |  |  |  |  |  |  |  |  |  |  |  |  |  |  |  |
|---|---|---|---|---|---|---|---|---|---|---|---|---|---|---|---|
|  |  |  |  |  | 20 |  |  |  |  | 25 |  |  |  |  | 30 |

```
AAT GGT TTA CAG GAT TTA GTC AAA GCG GCC GAA GAG TTG GGG ATT GAG        144
Asn Gly Leu Gln Asp Leu Val Lys Ala Ala Glu Glu Leu Gly Ile Glu
        35              40                  45

GTA CAA AGA GAA GAA CGC AAT AAT ATT GCA ACA GCT CAA ACC AGT TTA        192
Val Gln Arg Glu Glu Arg Asn Asn Ile Ala Thr Ala Gln Thr Ser Leu
 50                  55                  60

GGC ACG ATT CAA ACC GCT ATT GGC TTA ACT GAG CGT GGC ATT GTG TTA        240
Gly Thr Ile Gln Thr Ala Ile Gly Leu Thr Glu Arg Gly Ile Val Leu
 65              70                  75                   80

TCC GCT CCA CAA ATT GAT AAA TTG CTA CAG AAA ACT AAA GCA GGC CAA        288
Ser Ala Pro Gln Ile Asp Lys Leu Leu Gln Lys Thr Lys Ala Gly Gln
                 85                  90                  95

GCA TTA GGT TCT GCC GAA AGC ATT GTA CAA AAT GCA AAT AAA GCC AAA        336
Ala Leu Gly Ser Ala Glu Ser Ile Val Gln Asn Ala Asn Lys Ala Lys
            100                 105                 110

ACT GTA TTA TCT GGC ATT CAA TCT ATT TTA GGC TCA GTA TTG GCT GGA        384
Thr Val Leu Ser Gly Ile Gln Ser Ile Leu Gly Ser Val Leu Ala Gly
        115                 120                 125

ATG GAT TTA GAT GAG GCC TTA CAG AAT AAC AGC AAC CAA CAT GCT CTT        432
Met Asp Leu Asp Glu Ala Leu Gln Asn Asn Ser Asn Gln His Ala Leu
130                 135                 140

GCT AAA GCT GGC TTG GAG CTA ACA AAT TCA TTA ATT GAA AAT ATT GCT        480
Ala Lys Ala Gly Leu Glu Leu Thr Asn Ser Leu Ile Glu Asn Ile Ala
145                 150                 155                 160

AAT TCA GTA AAA ACA CTT GAC GAA TTT GGT GAG CAA ATT AGT CAA TTT        528
Asn Ser Val Lys Thr Leu Asp Glu Phe Gly Glu Gln Ile Ser Gln Phe
                165                 170                 175

GGT TCA AAA CTA CAA AAT ATC AAA GGC TTA GGG ACT TTA GGA GAC AAA        576
Gly Ser Lys Leu Gln Asn Ile Lys Gly Leu Gly Thr Leu Gly Asp Lys
            180                 185                 190

CTC AAA AAT ATC GGT GGA CTT GAT AAA GCT GGC CTT GGT TTA GAT GTT        624
Leu Lys Asn Ile Gly Gly Leu Asp Lys Ala Gly Leu Gly Leu Asp Val
        195                 200                 205

ATC TCA GGG CTA TTA TCG GGC GCA ACA GCT GCA CTT GTA CTT GCA GAT        672
Ile Ser Gly Leu Leu Ser Gly Ala Thr Ala Ala Leu Val Leu Ala Asp
210                 215                 220

AAA AAT GCT TCA ACA GCT AAA AAA GTG GGT GCG GGT TTT GAA TTG GCA        720
Lys Asn Ala Ser Thr Ala Lys Lys Val Gly Ala Gly Phe Glu Leu Ala
225                 230                 235                 240

AAC CAA GTT GTT GGT AAT ATT ACC AAA GCC GTT TCT TCT TAC ATT TTA        768
Asn Gln Val Val Gly Asn Ile Thr Lys Ala Val Ser Ser Tyr Ile Leu
                245                 250                 255

GCC CAA CGT GTT GCA GCA GGT TTA TCT TCA ACT GGG CCT GTG GCT GCT        816
Ala Gln Arg Val Ala Ala Gly Leu Ser Ser Thr Gly Pro Val Ala Ala
            260                 265                 270

TTA ATT GCT TCT ACT GTT TCT CTT GCG ATT AGC CCA TTA GCA TTT GCC        864
Leu Ile Ala Ser Thr Val Ser Leu Ala Ile Ser Pro Leu Ala Phe Ala
        275                 280                 285

GGT ATT GCC GAT AAA TTT AAT CAT GCA AAA AGT TTA GAG AGT TAT GCC        912
Gly Ile Ala Asp Lys Phe Asn His Ala Lys Ser Leu Glu Ser Tyr Ala
290                 295                 300

GAA CGC TTT AAA AAA TTA GGC TAT GAC GGA GAT AAT TTA TTA GCA GAA        960
Glu Arg Phe Lys Lys Leu Gly Tyr Asp Gly Asp Asn Leu Leu Ala Glu
305                 310                 315                 320

TAT CAG CGG GGA ACA GGG ACT ATT GAT GCA TCG GTT ACT GCA ATT AAT       1008
Tyr Gln Arg Gly Thr Gly Thr Ile Asp Ala Ser Val Thr Ala Ile Asn
                325                 330                 335

ACC GCA TTG GCC GCT ATT GCT GGT GGT GTG TCT GCT GCT GCA GCC AAC       1056
Thr Ala Leu Ala Ala Ile Ala Gly Gly Val Ser Ala Ala Ala Ala Asn
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 340 |     |     |     |     | 345 |     |     |     |     | 350 |     |      |
| TTA | AAA | GAT | TTA | ACA | TTT | GAA | AAA | GTT | AAA | CAT | AAT | CTT | GTC | ATC | ACG | 1104 |
| Leu | Lys | Asp | Leu | Thr | Phe | Glu | Lys | Val | Lys | His | Asn | Leu | Val | Ile | Thr |      |
|     |     | 355 |     |     |     |     | 360 |     |     |     |     | 365 |     |     |     |      |
| AAT | AGC | AAA | AAA | GAG | AAA | GTG | ACC | ATT | CAA | AAC | TGG | TTC | CGA | GAG | GCT | 1152 |
| Asn | Ser | Lys | Lys | Glu | Lys | Val | Thr | Ile | Gln | Asn | Trp | Phe | Arg | Glu | Ala |      |
|     | 370 |     |     |     |     | 375 |     |     |     |     | 380 |     |     |     |     |      |
| GAT | TTT | GCT | AAA | GAA | GTG | CCT | AAT | TAT | AAA | GCA | ACT | AAA | GAT | GAG | AAA | 1200 |
| Asp | Phe | Ala | Lys | Glu | Val | Pro | Asn | Tyr | Lys | Ala | Thr | Lys | Asp | Glu | Lys |      |
| 385 |     |     |     |     | 390 |     |     |     |     | 395 |     |     |     |     | 400 |      |
| ATC | GAA | GAA | ATC | ATC | GGT | CAA | AAT | GGC | GAG | CGG | ATC | ACC | TCA | AAG | CAA | 1248 |
| Ile | Glu | Glu | Ile | Ile | Gly | Gln | Asn | Gly | Glu | Arg | Ile | Thr | Ser | Lys | Gln |      |
|     |     |     |     | 405 |     |     |     |     | 410 |     |     |     |     | 415 |     |      |
| GTT | GAT | GAT | CTT | ATC | GCA | AAA | GGT | AAC | GGC | AAA | ATT | ACC | CAA | GAT | GAG | 1296 |
| Val | Asp | Asp | Leu | Ile | Ala | Lys | Gly | Asn | Gly | Lys | Ile | Thr | Gln | Asp | Glu |      |
|     |     |     | 420 |     |     |     |     | 425 |     |     |     |     | 430 |     |     |      |
| CTA | TCA | AAA | GTT | GTT | GAT | AAC | TAT | GAA | TTG | CTC | AAA | CAT | AGC | AAA | AAT | 1344 |
| Leu | Ser | Lys | Val | Val | Asp | Asn | Tyr | Glu | Leu | Leu | Lys | His | Ser | Lys | Asn |      |
|     |     | 435 |     |     |     |     | 440 |     |     |     |     | 445 |     |     |     |      |
| GTG | ACA | AAC | AGC | TTA | GAT | AAG | TTA | ATC | TCA | TCT | GTA | AGT | GCA | TTT | ACC | 1392 |
| Val | Thr | Asn | Ser | Leu | Asp | Lys | Leu | Ile | Ser | Ser | Val | Ser | Ala | Phe | Thr |      |
|     | 450 |     |     |     |     | 455 |     |     |     |     | 460 |     |     |     |     |      |
| TCG | TCT | AAT | GAT | TCG | AGA | AAT | GTA | TTA | GTG | GCT | CCA | ACT | TCA | ATG | TTG | 1440 |
| Ser | Ser | Asn | Asp | Ser | Arg | Asn | Val | Leu | Val | Ala | Pro | Thr | Ser | Met | Leu |      |
| 465 |     |     |     |     | 470 |     |     |     |     | 475 |     |     |     |     | 480 |      |
| GAT | CAA | AGT | TTA | TCT | TCT | CTT | CAA | TTT | GCT | AGG | GGA | TCT | CAG | CAT | TGG | 1488 |
| Asp | Gln | Ser | Leu | Ser | Ser | Leu | Gln | Phe | Ala | Arg | Gly | Ser | Gln | His | Trp |      |
|     |     |     |     | 485 |     |     |     |     | 490 |     |     |     |     | 495 |     |      |
| AGC | TAC | GGC | CTG | CGC | CCT | GGC | AGC | GGT | TCT | CAA | GAT | TGG | AGC | TAC | GGC | 1536 |
| Ser | Tyr | Gly | Leu | Arg | Pro | Gly | Ser | Gly | Ser | Gln | Asp | Trp | Ser | Tyr | Gly |      |
|     |     |     | 500 |     |     |     |     | 505 |     |     |     |     | 510 |     |     |      |
| CTG | CGT | CCG | GGT | GGC | TCT | AGC | CAG | CAT | TGG | AGC | TAC | GGC | CTG | CGC | CCT | 1584 |
| Leu | Arg | Pro | Gly | Gly | Ser | Ser | Gln | His | Trp | Ser | Tyr | Gly | Leu | Arg | Pro |      |
|     |     | 515 |     |     |     |     | 520 |     |     |     |     | 525 |     |     |     |      |
| GGC | AGC | GGT | AGC | CAA | GAT | TGG | AGC | TAC | GGC | CTG | CGT | CCG | GGT | GGA | TCC | 1632 |
| Gly | Ser | Gly | Ser | Gln | Asp | Trp | Ser | Tyr | Gly | Leu | Arg | Pro | Gly | Gly | Ser |      |
|     | 530 |     |     |     |     | 535 |     |     |     |     | 540 |     |     |     |     |      |
| TAG |     |     |     |     |     |     |     |     |     |     |     |     |     |     |     | 1635 |

( 2 ) INFORMATION FOR SEQ ID NO:10:

( i ) SEQUENCE CHARACTERISTICS:
( A ) LENGTH: 544 amino acids
( B ) TYPE: amino acid
( D ) TOPOLOGY: linear ( i i ) MOLECULE TYPE: protein ( x i ) SEQUENCE DESCRIPTION: SEQ ID NO:10:

|     |     |     |     |     |     |     |     |     |     |     |     |     |     |     |
| --- | --- | --- | --- | --- | --- | --- | --- | --- | --- | --- | --- | --- | --- | --- |
| Met | Ala | Thr | Val | Ile | Asp | Leu | Ser | Phe | Pro | Lys | Thr | Gly | Ala | Lys | Lys |
| 1   |     |     |     | 5   |     |     |     |     | 10  |     |     |     |     | 15  |     |
| Ile | Ile | Leu | Tyr | Ile | Pro | Gln | Asn | Tyr | Gln | Tyr | Asp | Thr | Glu | Gln | Gly |
|     |     |     | 20  |     |     |     |     | 25  |     |     |     |     | 30  |     |     |
| Asn | Gly | Leu | Gln | Asp | Leu | Val | Lys | Ala | Ala | Glu | Glu | Leu | Gly | Ile | Glu |
|     |     | 35  |     |     |     |     | 40  |     |     |     |     | 45  |     |     |     |
| Val | Gln | Arg | Glu | Glu | Arg | Asn | Asn | Ile | Ala | Thr | Ala | Gln | Thr | Ser | Leu |
|     | 50  |     |     |     |     | 55  |     |     |     |     | 60  |     |     |     |     |
| Gly | Thr | Ile | Gln | Thr | Ala | Ile | Gly | Leu | Thr | Glu | Arg | Gly | Ile | Val | Leu |
| 65  |     |     |     | 70  |     |     |     |     | 75  |     |     |     |     | 80  |     |
| Ser | Ala | Pro | Gln | Ile | Asp | Lys | Leu | Leu | Gln | Lys | Thr | Lys | Ala | Gly | Gln |

|     |     |     |     |     | 85  |     |     |     | 90  |     |     |     | 95  |     |
|-----|-----|-----|-----|-----|-----|-----|-----|-----|-----|-----|-----|-----|-----|-----|
| Ala | Leu | Gly | Ser | Ala | Glu | Ser | Ile | Val | Gln | Asn | Ala | Asn | Lys | Ala | Lys
|     |     |     | 100 |     |     |     |     | 105 |     |     |     | 110 |     |     |
| Thr | Val | Leu | Ser | Gly | Ile | Gln | Ser | Ile | Leu | Gly | Ser | Val | Leu | Ala | Gly
|     |     | 115 |     |     |     |     | 120 |     |     |     |     | 125 |     |     |
| Met | Asp | Leu | Asp | Glu | Ala | Leu | Gln | Asn | Asn | Ser | Asn | Gln | His | Ala | Leu
| 130 |     |     |     |     |     |     | 135 |     |     |     |     | 140 |     |     |
| Ala | Lys | Ala | Gly | Leu | Glu | Leu | Thr | Asn | Ser | Leu | Ile | Glu | Asn | Ile | Ala
| 145 |     |     |     |     | 150 |     |     |     |     | 155 |     |     |     |     | 160
| Asn | Ser | Val | Lys | Thr | Leu | Asp | Glu | Phe | Gly | Glu | Gln | Ile | Ser | Gln | Phe
|     |     |     |     | 165 |     |     |     |     | 170 |     |     |     |     | 175 |
| Gly | Ser | Lys | Leu | Gln | Asn | Ile | Lys | Gly | Leu | Gly | Thr | Leu | Gly | Asp | Lys
|     |     |     | 180 |     |     |     |     | 185 |     |     |     |     | 190 |     |
| Leu | Lys | Asn | Ile | Gly | Gly | Leu | Asp | Lys | Ala | Gly | Leu | Gly | Leu | Asp | Val
|     |     | 195 |     |     |     |     | 200 |     |     |     |     | 205 |     |     |
| Ile | Ser | Gly | Leu | Leu | Ser | Gly | Ala | Thr | Ala | Ala | Leu | Val | Leu | Ala | Asp
|     | 210 |     |     |     |     | 215 |     |     |     |     | 220 |     |     |     |
| Lys | Asn | Ala | Ser | Thr | Ala | Lys | Lys | Val | Gly | Ala | Gly | Phe | Glu | Leu | Ala
| 225 |     |     |     |     | 230 |     |     |     |     | 235 |     |     |     |     | 240
| Asn | Gln | Val | Val | Gly | Asn | Ile | Thr | Lys | Ala | Val | Ser | Ser | Tyr | Ile | Leu
|     |     |     |     | 245 |     |     |     |     | 250 |     |     |     |     | 255 |
| Ala | Gln | Arg | Val | Ala | Ala | Gly | Leu | Ser | Ser | Thr | Gly | Pro | Val | Ala | Ala
|     |     |     | 260 |     |     |     |     | 265 |     |     |     |     | 270 |     |
| Leu | Ile | Ala | Ser | Thr | Val | Ser | Leu | Ala | Ile | Ser | Pro | Leu | Ala | Phe | Ala
|     |     | 275 |     |     |     |     | 280 |     |     |     |     | 285 |     |     |
| Gly | Ile | Ala | Asp | Lys | Phe | Asn | His | Ala | Lys | Ser | Leu | Glu | Ser | Tyr | Ala
|     | 290 |     |     |     |     | 295 |     |     |     |     | 300 |     |     |     |
| Glu | Arg | Phe | Lys | Lys | Leu | Gly | Tyr | Asp | Gly | Asp | Asn | Leu | Leu | Ala | Glu
| 305 |     |     |     |     | 310 |     |     |     |     | 315 |     |     |     |     | 320
| Tyr | Gln | Arg | Gly | Thr | Gly | Thr | Ile | Asp | Ala | Ser | Val | Thr | Ala | Ile | Asn
|     |     |     |     | 325 |     |     |     |     | 330 |     |     |     |     | 335 |
| Thr | Ala | Leu | Ala | Ala | Ile | Ala | Gly | Gly | Val | Ser | Ala | Ala | Ala | Ala | Asn
|     |     |     | 340 |     |     |     |     | 345 |     |     |     |     | 350 |     |
| Leu | Lys | Asp | Leu | Thr | Phe | Glu | Lys | Val | Lys | His | Asn | Leu | Val | Ile | Thr
|     |     | 355 |     |     |     |     | 360 |     |     |     |     | 365 |     |     |
| Asn | Ser | Lys | Lys | Glu | Lys | Val | Thr | Ile | Gln | Asn | Trp | Phe | Arg | Glu | Ala
|     | 370 |     |     |     |     | 375 |     |     |     |     | 380 |     |     |     |
| Asp | Phe | Ala | Lys | Glu | Val | Pro | Asn | Tyr | Lys | Ala | Thr | Lys | Asp | Glu | Lys
| 385 |     |     |     |     | 390 |     |     |     |     | 395 |     |     |     |     | 400
| Ile | Glu | Glu | Ile | Ile | Gly | Gln | Asn | Gly | Glu | Arg | Ile | Thr | Ser | Lys | Gln
|     |     |     |     | 405 |     |     |     |     | 410 |     |     |     |     | 415 |
| Val | Asp | Asp | Leu | Ile | Ala | Lys | Gly | Asn | Gly | Lys | Ile | Thr | Gln | Asp | Glu
|     |     |     | 420 |     |     |     |     | 425 |     |     |     |     | 430 |     |
| Leu | Ser | Lys | Val | Val | Asp | Asn | Tyr | Glu | Leu | Leu | Lys | His | Ser | Lys | Asn
|     |     | 435 |     |     |     |     | 440 |     |     |     |     | 445 |     |     |
| Val | Thr | Asn | Ser | Leu | Asp | Lys | Leu | Ile | Ser | Ser | Val | Ser | Ala | Phe | Thr
|     | 450 |     |     |     |     | 455 |     |     |     |     | 460 |     |     |     |
| Ser | Ser | Asn | Asp | Ser | Arg | Asn | Val | Leu | Val | Ala | Pro | Thr | Ser | Met | Leu
| 465 |     |     |     |     | 470 |     |     |     |     | 475 |     |     |     |     | 480
| Asp | Gln | Ser | Leu | Ser | Ser | Leu | Gln | Phe | Ala | Arg | Gly | Ser | Gln | His | Trp
|     |     |     |     | 485 |     |     |     |     | 490 |     |     |     |     | 495 |
| Ser | Tyr | Gly | Leu | Arg | Pro | Gly | Ser | Gly | Ser | Gln | Asp | Trp | Ser | Tyr | Gly
|     |     |     | 500 |     |     |     |     | 505 |     |     |     |     | 510 |     |

```
Leu Arg Pro Gly Gly Ser Ser Gln His Trp Ser Tyr Gly Leu Arg Pro
        515                 520                 525

Gly Ser Gly Ser Gln Asp Trp Ser Tyr Gly Leu Arg Pro Gly Gly Ser
        530                 535                 540
```

(2) INFORMATION FOR SEQ ID NO:11:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..42

(xi) SEQUENCE DESCRIPTION: SEQ ID NO:11:

```
GCT GCA GCC GGC TCG GTT ATT TTC TCT GAT TCG AAC TTA AAA          42
Ala Ala Ala Gly Ser Val Ile Phe Ser Asp Ser Asn Leu Lys
 1           5                   10
```

(2) INFORMATION FOR SEQ ID NO:12:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:12:

```
Ala Ala Ala Gly Ser Val Ile Phe Ser Asp Ser Asn Leu Lys
 1           5                   10
```

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..18

(xi) SEQUENCE DESCRIPTION: SEQ ID NO:13:

```
GCT GCA GCC AAC TTA AAA                                          18
Ala Ala Ala Asn Leu Lys
 1           5
```

(2) INFORMATION FOR SEQ ID NO:14:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:14:

```
Ala Ala Ala Asn Leu Lys
 1           5
```

(2) INFORMATION FOR SEQ ID NO:15:

(i) SEQUENCE CHARACTERISTICS:
  (A) LENGTH: 6 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY: Modified-site
  (B) LOCATION: 3
  (D) OTHER INFORMATION: /note= "The amino acid at this location can be either Lys, Asp, Val or Asn."

(ix) FEATURE:
  (A) NAME/KEY: Modified-site
  (B) LOCATION: 5
  (D) OTHER INFORMATION: /note= "The amino acid at this location can be either Lys, Asp, Val or Asn."

(xi) SEQUENCE DESCRIPTION: SEQ ID NO:15:

Gly Gly Xaa Gly Xaa Asp
1               5

(2) INFORMATION FOR SEQ ID NO:16:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:16:

Gly Thr Ile Asp
1

(2) INFORMATION FOR SEQ ID NO:17:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:17:

Gly Ile Thr Gly
1

(2) INFORMATION FOR SEQ ID NO:18:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:18:

Gly Val Ile Ser
1

(2) INFORMATION FOR SEQ ID NO:19:

(i) SEQUENCE CHARACTERISTICS:
    (A) LENGTH: 4 amino acids
    (B) TYPE: amino acid ( C ) STRANDEDNESS: single
                    ( D ) TOPOLOGY: linear ( i i ) MOLECULE TYPE: peptide ( x i ) SEQUENCE DESCRIPTION: SEQ ID NO:19:

His  Val  Ala  Asn
        1

( 2 ) INFORMATION FOR SEQ ID NO:20:

( i ) SEQUENCE CHARACTERISTICS:
                    ( A ) LENGTH: 4 amino acids
                    ( B ) TYPE: amino acid
                    ( C ) STRANDEDNESS: single
                    ( D ) TOPOLOGY: linear ( i i ) MOLECULE TYPE: peptide ( x i ) SEQUENCE DESCRIPTION: SEQ ID NO:20:

Lys  Ile  Val  Glu
        1

( 2 ) INFORMATION FOR SEQ ID NO:21:

( i ) SEQUENCE CHARACTERISTICS:
                    ( A ) LENGTH: 4 amino acids
                    ( B ) TYPE: amino acid
                    ( C ) STRANDEDNESS: single
                    ( D ) TOPOLOGY: linear ( i i ) MOLECULE TYPE: peptide ( x i ) SEQUENCE DESCRIPTION: SEQ ID NO:21:

Asp  Leu  Ala  Gly
        1

( 2 ) INFORMATION FOR SEQ ID NO:22:

( i ) SEQUENCE CHARACTERISTICS:
                    ( A ) LENGTH: 4 amino acids
                    ( B ) TYPE: amino acid
                    ( C ) STRANDEDNESS: single
                    ( D ) TOPOLOGY: linear ( i i ) MOLECULE TYPE: peptide ( x i ) SEQUENCE DESCRIPTION: SEQ ID NO:22:

Lys  Val  Leu  Ser
        1

( 2 ) INFORMATION FOR SEQ ID NO:23:

( i ) SEQUENCE CHARACTERISTICS:
                    ( A ) LENGTH: 4 amino acids
                    ( B ) TYPE: amino acid
                    ( C ) STRANDEDNESS: single
                    ( D ) TOPOLOGY: linear ( i i ) MOLECULE TYPE: peptide ( x i ) SEQUENCE DESCRIPTION: SEQ ID NO:23:

Asp  Ala  Phe  Glu
        1

( 2 ) INFORMATION FOR SEQ ID NO:24:

( i ) SEQUENCE CHARACTERISTICS:
                    ( A ) LENGTH: 4 amino acids
                    ( B ) TYPE: amino acid -continued

```
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

Lys  Leu  Val  Gln
        1
```

( 2 ) INFORMATION FOR SEQ ID NO:25:

```
    ( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

Gly  Ile  Ile  Asp
        1
```

( 2 ) INFORMATION FOR SEQ ID NO:26:

```
    ( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

Arg  Tyr  Leu  Ala  Asn
        1                   5
```

( 2 ) INFORMATION FOR SEQ ID NO:27:

```
    ( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

Lys  Phe  Leu  Leu  Asn
        1                   5
```

( 2 ) INFORMATION FOR SEQ ID NO:28:

```
    ( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:28:

Lys  Ala  Tyr  Val  Asp
        1                   5
```